US010392604B2

(12) United States Patent
Egorov et al.

(10) Patent No.: US 10,392,604 B2
(45) Date of Patent: Aug. 27, 2019

(54) ATTENUATED INFLUENZA VECTORS FOR THE PREVENTION AND/OR TREATMENT OF INFECTIOUS DISEASES AND FOR THE TREATMENT OF ONCOLOGICAL DISEASES

(71) Applicant: PHARMENTERPRISES BIOTECH Limited Liability Company, Moscow (RU)

(72) Inventors: Andrei Yurievich Egorov, St. Petersburg (RU); Boris Ferko, Vienna (AT); Artem Alexandrovich Krokhin, The Crimea (RU); Yulia Romanovna Romanova, St. Petersburg (RU)

(73) Assignee: PHARMENTERPRISES BIOTECH Limited Liability Company, Moscow (RU)

( * ) Notice: Subject to any disclaimer, the term of this patent is extended or adjusted under 35 U.S.C. 154(b) by 0 days.

(21) Appl. No.: 15/566,202

(22) PCT Filed: Nov. 3, 2016

(86) PCT No.: PCT/RU2016/050066
§ 371 (c)(1),
(2) Date: Oct. 12, 2017

(87) PCT Pub. No.: WO2017/078577
PCT Pub. Date: May 11, 2017

(65) Prior Publication Data
US 2018/0245052 A1 Aug. 30, 2018

(30) Foreign Application Priority Data

Nov. 6, 2015 (RU) ................................ 2015147703
Mar. 30, 2016 (RU) ................................ 2016111907

(51) Int. Cl.

| | |
|---|---|
| *C12N 7/00* | (2006.01) |
| *A61K 35/76* | (2015.01) |
| *A61K 39/00* | (2006.01) |
| *A61K 39/12* | (2006.01) |
| *A61P 31/16* | (2006.01) |
| *C12N 15/86* | (2006.01) |
| *A61K 39/145* | (2006.01) |
| *C07K 14/005* | (2006.01) |

(52) U.S. Cl.

CPC ................ *C12N 7/00* (2013.01); *A61K 35/76* (2013.01); *A61K 39/12* (2013.01); *A61K 39/145* (2013.01); *A61P 31/16* (2018.01); *C07K 14/005* (2013.01); *C12N 15/86* (2013.01); *A61K 2039/5254* (2013.01); *C12N 2760/16121* (2013.01); *C12N 2760/16122* (2013.01); *C12N 2760/16143* (2013.01); *C12N 2760/16162* (2013.01); *C12N 2760/16171* (2013.01)

(58) Field of Classification Search
CPC ............ C12N 7/00; C12N 2760/16143; C12N 2760/16171; C12N 2760/16122; C12N 15/86; C12N 2760/16162; C12N 2760/16121; A61K 39/12; A61K 35/76; A61K 39/145; A61K 2039/5254; C07K 14/005; A61P 31/16
See application file for complete search history.

(56) References Cited

U.S. PATENT DOCUMENTS

| | | | | |
|---|---|---|---|---|
| 6,468,544 B1 * | 10/2002 | Egorov ................ | A61K 39/145 424/209.1 |
| 6,800,288 B2 | 10/2004 | Ferko et al. | |
| 7,037,707 B2 | 5/2006 | Webster et al. | |
| 8,592,196 B2 * | 11/2013 | Kittel .................. | A61K 39/145 424/184.1 |
| 2009/0053264 A1 | 2/2009 | Palese et al. | |
| 2010/0136052 A1 * | 6/2010 | Wolschek ........... | C07K 14/005 424/206.1 |
| 2012/0244183 A1 * | 9/2012 | Garcia-Sastre ...... | C07K 14/005 424/209.1 |

FOREIGN PATENT DOCUMENTS

WO WO-2014041082 A1 * 3/2014 ........... C07K 14/005

OTHER PUBLICATIONS

Vasin AV, Petrova AV, Egorov VV, Plotnikova MA, Klotchenko SA, Karpenko MN, Kiselev OI. The influenza A virus NS genome segment displays lineage-specific patterns in predicted RNA secondary structure. BMC Res Notes. May 20, 2016;9:279.*

Steel J, Lowen AC, Pena L, Angel M, Solórzano A, Albrecht R, Perez DR, García-Sastre A, Palese P. Live attenuated influenza viruses containing NS1 truncations as vaccine candidates against H5N1 highly pathogenic avian influenza. J Virol. Feb. 2009;83(4): 1742-53. doi: 10.1128/JVI.01920-08. Epub Dec. 10, 2008.*

Quinlivan M, Zamarin D, García-Sastre A, Cullinane A, Chambers T, Palese P. Attenuation of equine influenza viruses through truncations of the NS1 protein. J Virol. Jul. 2005;79(13):8431-9.*
Tabynov K, Yespembetov B, Sansyzbay A. Novel vector vaccine against *Brucella abortus* based on influenza A viruses expressing *Brucella* L7/L12 or Omp16 proteins: evaluation of protection in pregnant heifers. Vaccine. Oct. 14, 2014;32(45):5889-92. doi: 10.1016/j.vaccine.2014.08.073. Epub Sep. 13, 2014.*

Tabynov K, Kydyrbayev Z, Ryskeldinova S, et. al. Novel influenza virus vectors expressing *Brucella* L7/L12 or Omp16 proteins in cattle induced a strong T-cell immune response, as well as high protectiveness against *B. abortus* infection. Vaccine. Apr. 11, 2014;32(18):2034-41. Epub Mar. 2, 2014.*

(Continued)

*Primary Examiner* — Rachel B Gill

(74) *Attorney, Agent, or Firm* — Morrison & Foerster LLP

(57) ABSTRACT

The present invention relates to the field of medicine and virology. An attenuated influenza A virus, an influenza virus vector based thereon, and a pharmaceutical composition comprising thereof are provided, which can be used for the prevention and/or treatment of an infectious disease. In addition, the present invention relates to an attenuated influenza A virus, an influenza virus vector based thereon, and a pharmaceutical composition comprising thereof, which can be used for the treatment of oncological diseases.

39 Claims, 14 Drawing Sheets

Specification includes a Sequence Listing.

(56) References Cited

OTHER PUBLICATIONS

Tabynov K, Sansyzbay A, Kydyrbayev Z, Yespembetov B, Ryskeldinova S, Zinina N, Assanzhanova N, Sultankulova K, Sandybayev N, Khairullin B, Kuznetsova I, Ferko B, Egorov A. Influenza viral vectors expressing the *Brucella* OMP16 or L7/L12 proteins as vaccines against *B. abortus* infection. Virol J. Apr. 10, 2014;11:69.*

Wolschek M, Samm E, Seper H, Sturlan S, Kuznetsova I, Schwager C, Khassidov A, Kittel C, Muster T, Egorov A, Bergmann M. Establishment of a chimeric, replication-deficient influenza A virus vector by modulation of splicing efficiency. J Virol. Mar. 2011;85(5):2469-73. Epub Dec. 22, 2010.*

Sadikaliyeva SO, Sultankulova KT, Shorayeva KA, Strochkov VM, Chervyakova OV, Zaitsev VL, Tabynov KK, Sandybayev NT, Sansyzbay AR, Egorov AY. [Genetic stability of the HA, NA, and NS genes of the recombinant vector virus Flu-NS1-124-Omp16 (H5N1) expressing the brucellar gene]. Vopr Virusol. 2015;60(4):18-23.*

Min JY, Li S, Sen GC, Krug RM. A site on the influenza A virus NS1 protein mediates both inhibition of PKR activation and temporal regulation of viral RNA synthesis. Virology. Jun. 20, 2007;363(1):236-43. Epub Feb. 22, 2007.*

Winter G, Fields S, Gait MJ, Brownlee GG. Nonstructural protein 1 [Influenza A virus (A/Puerto Rico/8/1934(H1N1))]. NCBI Reference Sequence: NP_040984.1. Jun. 12, 2000.*

Ferko et al. (2001). "Hyperattenuated Recombinant Influenza A Virus Nonstructural-Protein-Encoding Vectors Induce Human Immunodeficiency Virus Type 1 Nef-Specific Systemic and Mucosal Immune Responses in Mice," Journal of Virology, vol. 75, No. 19, p. 8899-8908.

International Search Report dated May 4, 2017, for PCT/RU/2016/050066, 2 pages.

Efferson et al., "Prostate Tumor Cells Infected with a Recombinant Influenza Virus Expressing a Truncated NS1 Protein Activate Cytolytic CD8+ Cells to Recognize Noninfected Tumor Cells", Journal of Virology, vol. 80, No. 1, Jan. 2006, pp. 383-394.

Egorov et al., "Transfectant Influenza A Viruses with Long Deletions in the NS1 Protein Grow Efficiently in Vero Cells", Journal of Virology, vol. 72, No. 8, Aug. 1998, pp. 6437-6441.

Ferko et al., "Immunogenicity and Protection Efficacy of Replication-Deficient Influenza A Viruses with Altered NS1 Genes", Journal of Virology, vol. 78, No. 23, Dec. 2004, pp. 13037-13045.

Hoffmann et al., "A DNA Transfection System for Generation of Influenza A Virus from Eight Plasmids", PNAS, vol. 97, No. 11, May 23, 2000, pp. 6108-6113.

International Preliminary Report on Patentability received for PCT Patent Application No. PCT/RU2016/050066, dated Feb. 28, 2018, 9 pages (5 pages of English Translation and 4 pages of Official Copy).

International Written Opinion received for PCT Patent Application No. PCT/RU2016/050066, dated May 4, 2017, 4 pages (Official Copy Only) (See Communication under 37 CFR § 1.98(a) (3)).

Kittel et al., "Rescue of Influenza Virus Expressing GFP from the NS1 Reading Frame", Virology, vol. 324, 2004, pp. 67-73.

Ogbomo et al., "Tumor Cells Infected with Oncolytic Influenza A Virus Prime Natural Killer Cells for Lysis of Resistant Tumor Cells", Medical Microbiology and Immunology, vol. 199, 2010, pp. 93-101.

Rikxoort et al., "Oncolytic Effects of a Novel Influenza A Virus Expressing Interleukin-15 from the NS Reading Frame", Plos One, vol. 7, No. 5, May 2012, pp. 1-11.

Sereinig et al., "Influenza Virus NS Vectors Expressing the *Mycobacterium tuberculosis* ESAT-6 Protein Induce CD4+ Th1 Immune Response and Protect Animals against Tuberculosis Challenge", Clinical and Vaccine Immunology, vol. 13, No. 8, Aug. 2006, pp. 898-904.

Stukova et al., "Vaccine Potential of Influenza Vectors Expressing *Mycobacterium tuberculosis* ESAT-6 Protein", Tuberculosis, vol. 86, 2006, pp. 236-246.

Sturlan et al., "Endogenous Expression of Proteases in Colon Cancer Cells Facilitate Influenza A Viruses Mediated Oncolysis", Cancer Biology & Therapy, vol. 10, No. 6, Sep. 15, 2010, pp. 592-599.

* cited by examiner

FIG. 1
(A)
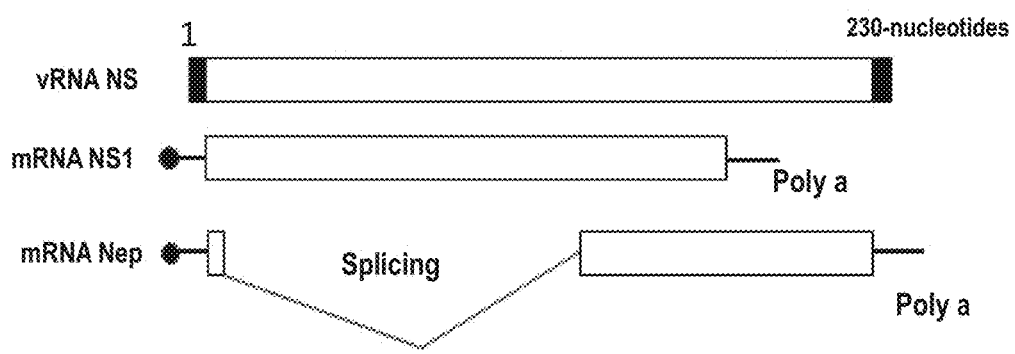
(B)
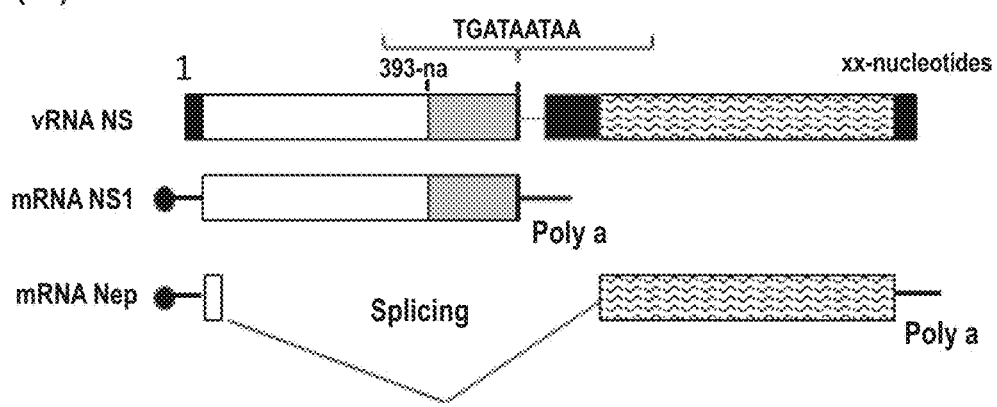
| | |
|---|---|
| ●— | Cap structure of mRNA |
| ■ | Untranslated region |
| ▨ | Variable region of an insertion |
| ⌇ | Nep heterologous sequence |
| Poly a | Polyadenylation site |
| TGATAATAA | Triple stop codon cassette |

AGCAAAAGCAGGGTGACAAAGACATAATGGATCCAAACACTGTGTCAAGCTTTCAGGTAGA
TTGCTTTCTTTGGCATGTCCGCAAACGAGTTGCAGACCAAGAACTAGGTGATGCCCCATTC
CTTGATCGGCTTCGCCGAGATCAGAAATCCCTAAGAGGAAGGGGCAGCACTCTTGGTCTG
GACATCGAGACAGCCACACGTGCTGGAAAGCAGATAGTGGAGCGGATTCTGAAAGAAGAA
TCCGATGAGGCACTTAAAATGACCATGGCCTCTGTACCTGCGTCGCGTTACCTAACCGACA
TGACTCTTGAGGAAATGTCAAGGGAATGGTCCATGCTCATACCCAAGCAGAAAGTGGCAG
GCCCTCTTTGTATCAGAATGGACCAGGCGATCATG<u>GATAAAAACATCATACTGAAAGCGA
ACTTC</u>AGTGTGATTTTTGACCGGCTGGAGACTCTAATATTGCTAAGGGCTTTCACCGAAGA
GGGAGCAATTGTTGGCGAAATTTCACCATTGCCTTCTCTTCCAG**GACATACTGCTGAGGAT
GTCAAAAATGCAGTTGGAGTCCTCATCGGAGGACTTGAATGGAATGATAACACAGTTCG
AGTCTCTGAAACTCTACAGAGATTCGCTTGGAGAAGCAGTAATGAGAATGGGAGACCTC
CACTCACTCCAAAACAGAAACGAGAAATGGCGGGAACAATTAGGTCAGAAGTTTGAAGA
AATAAGATGGTTGATTGAAGAAGTGAGACACAAACTGAAGGTAACAGAGAATAGTTTTG
AGCAAATAACATTTATGCAAGCCTTACATCTATTGCTTGAAGTGGAGCAAGAGATAAGAA
CTTTCTCATTTCAGCTTATTTAATAATAAAAAACACCCTTGTTTCTACT** (SEQ ID NO:1)

(B)

AGCAAAAGCAGGGTGACAAAGACATAATGGATCCAAACACTGTGTCAAGCTTTCAGGTAGA
TTGCTTTCTTTGGCATGTCCGCAAACGAGTTGCAGACCAAGAACTAGGTGATGCCCCATTC
CTTGATCGGCTTCGCCGAGATCAGAAATCCCTAAGAGGAAGGGGCAGCACTCTTGGTCTG
GACATCGAGACAGCCACACGTGCTGGAAAGCAGATAGTGGAGCGGATTCTGAAAGAAGAA
TCCGATGAGGCACTTAAAATGACCATGGCCTCTGTACCTGCGTCGCGTTACCTAACCGACA
TGACTCTTGAGGAAATGTCAAGGGAATGGTCCATGCTCATACCCAAGCAGAAAGTGGCAG
GCCCTCTTTGTATCAGAATGGACCAGGCGATCATG<u>TGATAATAA</u>AGTGTGATTTTTGACCG
GCTGGAGACTCTAATATTGCTAAGGGCTTTCACCGAAGAGGGAGCAATTGTTGGCGAAATT
TCACCATTGCCTTCTCTTCCAG**GACATACTAATGAGGATGTCAAAAATGCAATTGGGGTC
CTCATCGGAGGACTTGAATGGAATGATAACACAGTTCGAGTCTCTAAAACTCTACAGAGA
TTCGCTTGGTGAAACAGTAATGAGAATGGGAGACCTCCACTCACTCCAAAACAGAAACG
GAAAATGGCGAGAACAATTAGGTCAAAAGTTCGAAGAAATAAGATGGCTGATTGAAGAA
GTGAGACACAAATTGAAGATAACAGAGAATAGTTTTGAGCAAATAACATTTATGCAAGCC
TTACAGCTACTATTTGAAGTGGAACAAGAGATAAGAACTTTCTCGTTTCAGCTTATTTAAT
AATAAAAAACACCCTTGTTTCTACT** (SEQ ID NO:2)

(C)

AGCAAAAGCAGGGTGACAAAGACATAATGGATCCAAACACTGTGTCAAGCTTTCAGGTAGA
TTGCTTTCTTTGGCATGTCCGCAAACGAGTTGCAGACCAAGAACTAGGTGATGCCCCATTC
CTTGATCGGCTTCGCCGAGATCAGAAATCCCTAAGAGGAAGGGGCAGCACTCTTGGTCTG
GACATCGAGACAGCCACACGTGCTGGAAAGCAGATAGTGGAGCGGATTCTGAAAGAAGAA
TCCGATGAGGCACTTAAAATGACCATGGCCTCTGTACCTGCGTCGCGTTACCTAACCGACA
TGACTCTTGAGGAAATGTCAAGGGAATGGTCCATGCTCATACCCAAGCAGAAAGTGGCAG
GCCCTCTTTGTATCAGAATGGACCAGGCGATCATG<u>TGATAATAA</u>AGTGTGATTTTTGACCG
GCTGGAGACTCTAATATTGCTAAGGGCTTTCACCGAAGAGGGAGCAATTGTTGGCGAAATT
TCACCATTGCCTTCTCTTCCAG**GACATACTAATGAGGATGTCAAAAATGCAATTGGGGTC
CTCATCGGAGGACTTGAATGGAATGATAACACAGTTCGAGTCTCTAAAACTCTACAGAGA
TTCGCTTGGAGAAGCAGTAATGAGAATGGGAGACCTCCACTCACTCCAAAACAGAAACG
GAAAATGGCGAGAACAATTAGGTCAAAAGTTCGAAGAAATAAGATGGCTGATTGAAGAA
GTGAGACACAAATTGAAGATAACAGAGAATAGTTTTGAGCAAATAACATTTATACAAGCC
TTACAGCTACTATTTGAAGTGGAACAAGAGATAAGAACTTTCTCGTTTCAGCTTATTTAAT
AATAAAAAACACCCTTGTTTCTACT** (SEQ ID NO:3)

FIG. 3

NS124/Nep-Len

MDPNTVSSFQVDCFLWHVRKRVADQELGDAPFLDRLRRDQKSLRGRGSTLGLDIETATRAGKQIVERILKEESDEALKMTMASVPA
SRYLTDMTLEEMSREWSMLIPKQKVAGPLCIRMDQAIM (SEQ ID NO:4)

NS124-HA2(A)-185

MDPNTVSSFQVDCFLWHVRKRVADQELGDAPFLDRLRRDQKSLRGRGSTLGLDIETATRAGKQIVERILKEESDEALKMTMASVPA
SRYLTDMTLEEMSREWSMLIPKQKVAGPLCIRMDQAIM-GG-**GLFGAIAGFIEGGWTGMIDGWYGYHH
QNEQGSGYAADQKSTQNAINGITNKVNTVIEKMNIQFTAVGKEFNKLEKRMENLNKKVDDGFLDIWTYNAELLVLLENERTLDF
HDSNVKNLYEKVKSQLKNNAKEIGNGCFEFYHKCDNECMESVRNGTYDYPKYSEESKLNREKVDGVKLESMGIYQ** (SEQ ID
NO:5)

NS124-HA2(A)-65-222

MDPNTVSSFQVDCFLWHVRKRVADQELGDAPFLDRLRRDQKSLRGRGSTLGLDIETATRAGKQIVERILKEESDEALKMTMASVPA
SRYLTDMTLEEMSREWSMLIPKQKVAGPLCIRMDQAIM-*GG*-**AVGKEFNKLEKRMENLNKKVDDGFLDI
WTYNAELLVLLENERTLDFHDSNVKNLYEKVKSQLKNNAKEIGNGCFEFYHKCDNECMESVRNGTYDYPKYSEESKLNREKVDG
VKLESMGIYQILAIYSTVASSLVLLVSLGAISFWMCSNGSLQCRICI** (SEQ ID NO:6)

NS124-HA2(A)-23-185

MDPNTVSSFQVDCFLWHVRKRVADQELGDAPFLDRLRRDQKSLRGRGSTLGLDIETATRAGKQIVERILKEESDEALKMTMASVPA
SRYLTDMTLEEMSREWSMLIPKQKVAGPLCIRMDQAIM-*GG*-**GYHHQNEQGSGYAADQKSTQNAINGI
TNKVNTVIEKMNIQFTAVGKEFNKLEKRMENLNKKVDDGFLDIWTYNAELLVLLENERTLDFHDSNVKNLYEKVKSQLKNNAKEI
GNGCFEFYHKCDNECMESVRNGTYDYPKYSEESKLNREKVDGVKLESMGIYQ** (SEQ ID NO:7)

NS124-HA2(B)-186

MDPNTVSSFQVDCFLWHVRKRVADQELGDAPFLDRLRRDQKSLRGRGSTLGLDIETATRAGKQIVERILKEESDEALKMTMASVPA
SRYLTDMTLEEMSREWSMLIPKQKVAGPLCIRMDQAIM-*GG*- **GFFGAIAGFLEGGWEGMIAGWHGYT
SHGAHGVAVAADLKSTQEAINKITKNLNSLSELEVKNLQRLSGAMNGLHDEILELDEKVDDLRADTISSQIELAVLLSNEGIINSEDE
HLLALERKLKKMLGPSAVEIGNGCFETKHKCNQTCLDRIAAGTFNAGDFSLPTFD** (SEQ ID NO:8)

NS124-Fus(A)-NP

MDPNTVSSFQVDCFLWHVRKRVADQELGDAPFLDRLRRDQKSLRGRGSTLGLDIETATRAGKQIVERILKEESDEALKMTMASVPA
SRYLTDMTLEEMSREWSMLIPKQKVAGPLCIRMDQAIM-*GG*-GLFGAIAGFIEGGWTGMIDGW-*GG*-RESRNPGNA (SEQ ID
NO:9)

NS124-Fus(B)-NP

MDPNTVSSFQVDCFLWHVRKRVADQELGDAPFLDRLRRDQKSLRGRGSTLGLDIETATRAGKQIVERILKEESDEALKMTMASVPA
SRYLTDMTLEEMSREWSMLIPKQKVAGPLCIRMDQAIM-*GG*- GFFGAIAGFLEGGWEGMIAGW -*GG*-RESRNPGNA (SEQ ID
NO:10)

NS124-Esat6

MDPNTVSSFQVDCFLWHVRKRVADQELGDAPFLDRLRRDQKSLRGRGSTLGLDIETATRAGKQIVERILKEESDEALKMTMASVPA
SRYLTDMTLEEMSREWSMLIPKQKVAGPLCIRMDQAIM-*GG*-**MTEQQWNFAGIEAAASAIQGNV
TSIHSLLDEGKQSLTKLAAAWGGSGSEAYQGVQQKWDATATELNNALQNLARTISEAGQAMASTEGNVTGMFA** (SEQ ID
NO:11)

NS124-2A-Esat6

MDPNTVSSFQVDCFLWHVRKRVADQELGDAPFLDRLRRDQKSLRGRGSTLGLDIETATRAGKQIVERILKEESDEALKMTMASVPA
SRYLTDMTLEEMSREWSMLIPKQKVAGPLCIRMDQAIM-*GG*-NFDLLKLAGDVESNPGP-
MTEQQWNFAGIEAAASAIQGNVTSIHSLLDEGKQSLTKLAAAWGGSGSEAYQGVQQKWDATATELNNALQNLARTISEAGQA
MASTEGNVTGMFA (SEQ ID NO:12)

NS124-HSV-2ASY

MDPNTVSSFQVDCFLWHVRKRVADQELGDAPFLDRLRRDQKSLRGRGSTLGLDIETATRAGKQIVERILKEESDEALKMTMASVPA
SRYLTDMTLEEMSREWSMLIPKQKVAGPLCIRMDQAIM-AAA-NLLTTPKFT-AAA-RMLGDVMAV-AAA-NLLTTPKFT-AAA-
RMLGDVMAV (SEQ ID NO:13)

FIG. 4
(A)
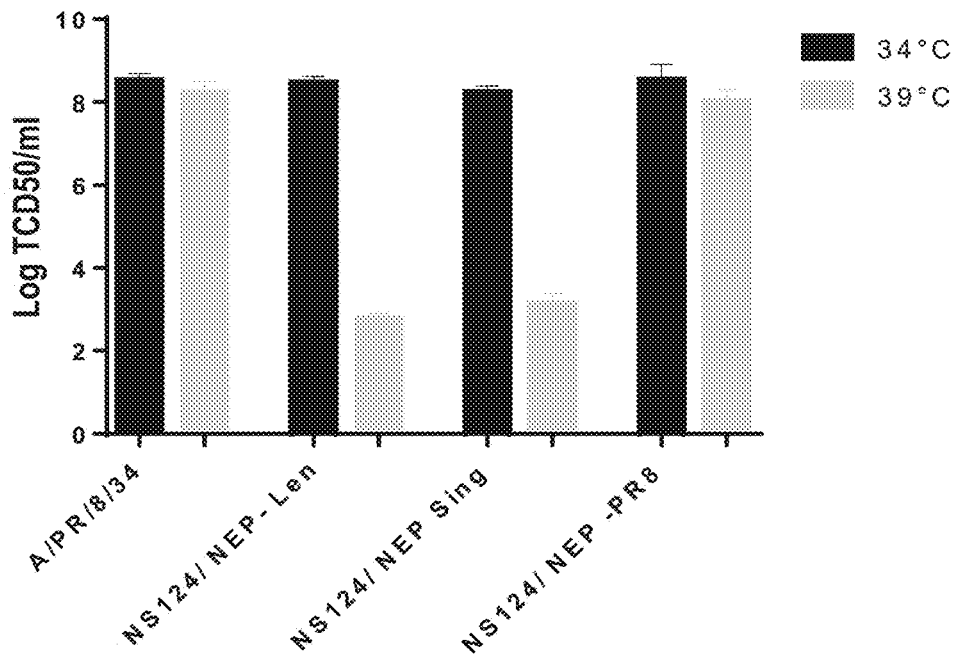
(B)
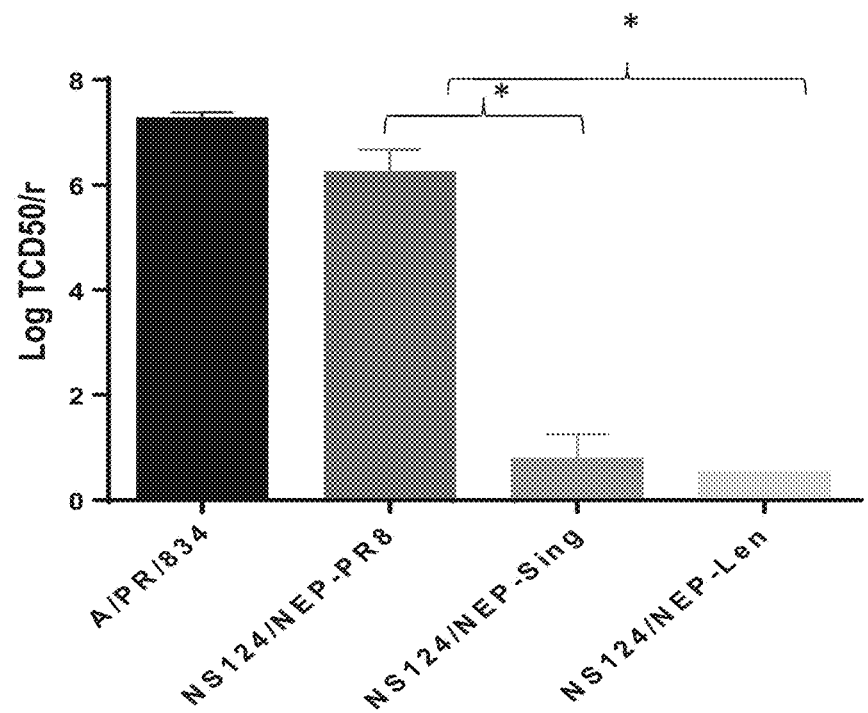

FIG. 5
(A)
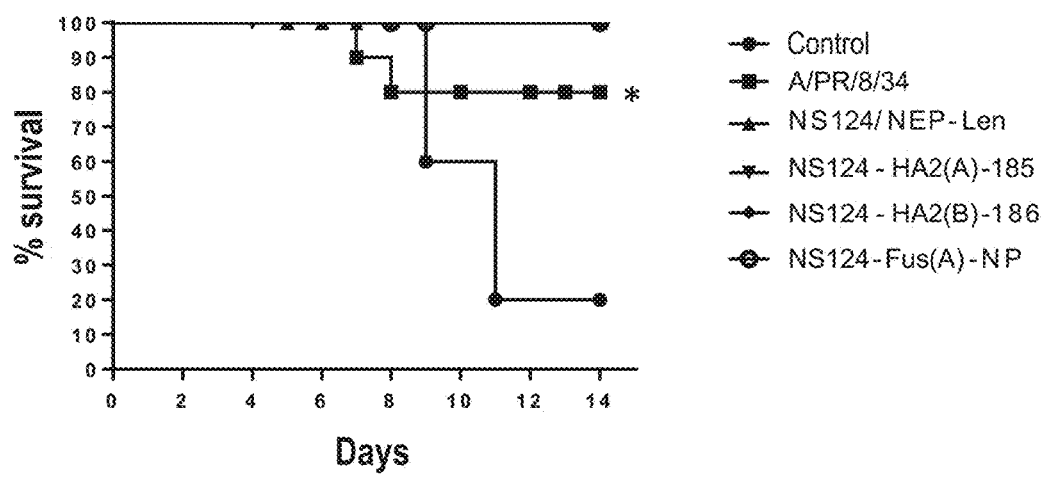
(B)
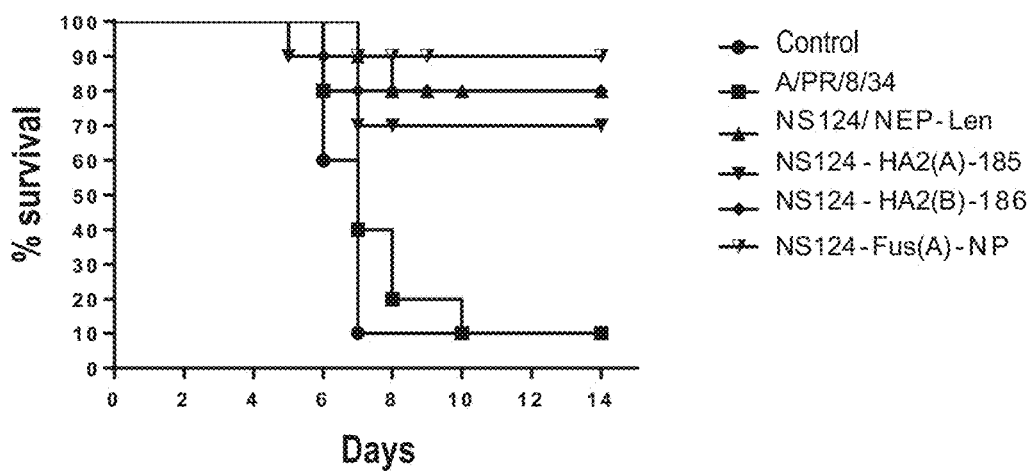

FIG. 6
(A)
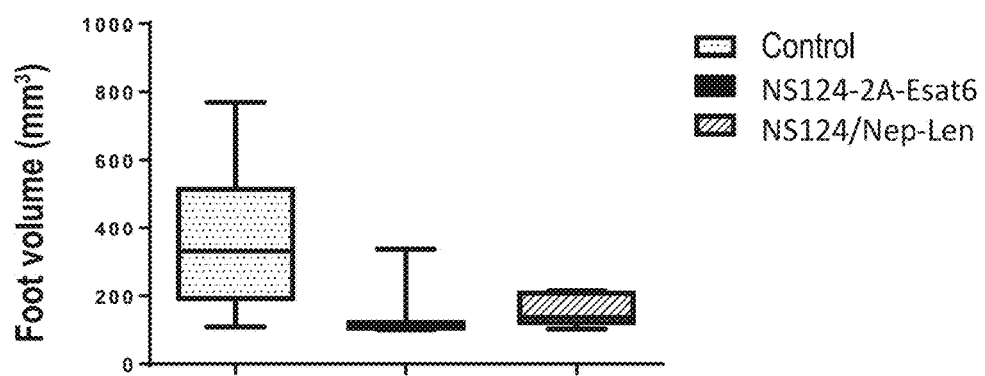
(B)
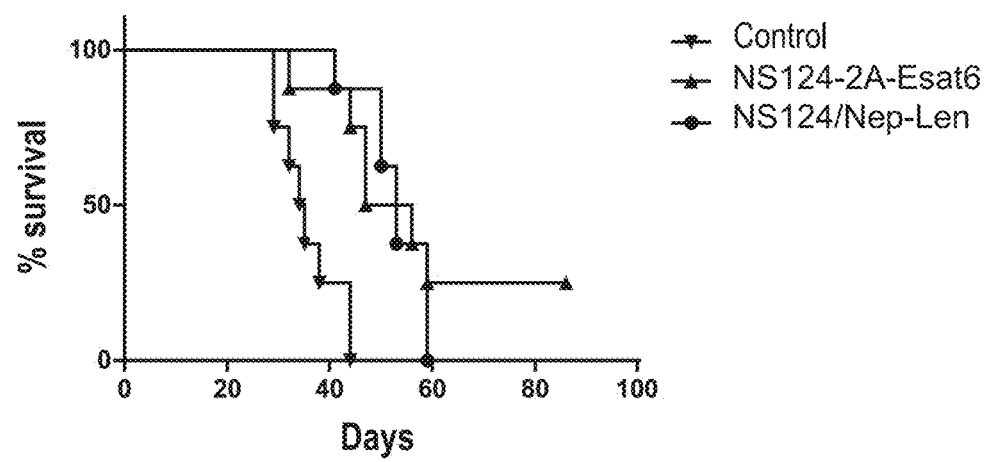

FIG. 7

Influenza virus vector genomic fragments

| | |
|---|---|
| PB2 | A/PR/8/34 |
| PB1 | A/PR/8/34 |
| PA | A/PR/8/34 |
| HA | A/California/7/09 (H1N1pdm) |
| NA | A/California/7/09 (H1N1pdm) |
| NP | A/PR/8/34 |
| M | A/PR/8/34 |
| chimeric NS | |

Origin of the genomic fragments from influenza virus strains

NS1 — 124 HA2 (B) +NP (A) — Truncated NS1 protein with an insertion

Nep — Nep protein from H2N2 heterologous strain

FIG. 8

PB2 agcgaaagcaggtcaattatattcaatatggaaagaataaaagaactacgaaatctaatgtcgcagtctcgcacccgcgagatact
cacaaaaaccaccgtgaccatatggccataatcaagaagtacacatcaggaagacaggagaagaacccagcacttaggatga
aatggatgatggcaatgaaatatccaattacagcagacaagaggataacggaaatgattcctgagagaaatgagcaaggacaaa
ctttatggagtaaaaatgaatgatgccggatcagaccgagtgatggtatcacctctggctgtgacatggtggaataggaatggacca
ataacaaatacagttcattatccaaaaatctacaaaacttattttgaaagagtcgaaaggctaaagcatggaaccttggccctgtc
cattttagaaaccaagtcaaaatacgtcggagagttgacataaatcctggtcatgcagatctcagtgccaaggaggcacaggatgt
aatcatggaagttgttttccctaacgaagtgggagccaggatactaacatcggaatcgcaactaacgataaccaaagagaagaaa
gaagaactccaggattgcaaaatttctcctttgatggttgcatacatgttggagagagaactggtccgcaaaacgagattcctccca
gtggctggtggaacaagcagtgtgtacattgaagtgttgcatttgactcaaggaacatgctgggaacagatgtatactccaggagg
ggaagtgaggaatgatgatgttgatcaaagcttgattattgctgctaggaacatagtgagaagagctgcagtatcagcagatccact
agcatctttattggagatgtgccacagcacacagattggtggaattaggatggtagacatccttaggcagaacccaacagaagagc
aagccgtggatatatgcaaggctgcaatgggactgagaattagctcatccttcagttttggtggattcacatttaagagaacaagcg
gatcatcagtcaagagagaggaagaggtgcttacgggcaatcttcaaacattgaagataagagtgcatgagggatatgaagagtt
cacaatggttgggagaagagcaacagccatactcagaaaaagcaaccaggagattgattcagctgatagtgagtgggagagacga
acagtcgattgccgaagcaataattgtggccatggtattttcacaagaggattgtatgataaaagcagtcagaggtgatctgaatttc
gtcaataggcgaatcaacgattgaatcctatgcatcaactttaagacatttcagaaggatgcgaaagtgctttttcaaaattggg
gagttgaacctatcgacaatgtgatgggaatgattgggatattgcccgacatgactccaagcatcgagatgtcaatgagaggagtg
agaatcagcaaaatgggtgtagatgagtactccagcacggagagggtagtggtgagcattgaccgttttttgagaatccgggacca
acgaggaaatgtactactgtctcccgaggaggtcagtgaaacacagggaacagagaaactgacaataacttactcatcgtcaatg
atgtgggagattaatggtcctgaatcagtgttggtcaatacctatcaatggatcatcagaaactgggaaactgttaaaattcagtggt
cccagaaccctacaatgctatacaataaaatggaatttgaaccatttcagtctcttagtacctaaggccattagaggccaatacagtg
ggtttgtaagaactctgttccaacaaatgagggatgtgcttgggacatttgataccgcacagataataaaacttcttcccttcgcagc
cgctccaccaaagcaaagtagaatgcagttctcctcatttactgtgaatgtgaggggatcaggaatgagaatacttgtaaggggca
attctcctgtattcaactataacaaggccacgaagagactcacagttctcggaaaggatgctggcactttaactgaagacccagatg
aaggcacagctggagtggagtccgctgttctgagggattcctcattctgggcaaagaagacaagagatatgggccagcactaag
catcaatgaactgagcaaccttgcgaaaggagagaaggctaatgtgctaattgggcaaggagacgtggtgttggtaatgaaacgg
aaacgggactctagcatacttactgacagccagacagcgaccaaaagaattcggatggccatcaattagtgtcgaatagtttaaaa
acgaccttgtttctact

SEQ ID NO: 14

PB1 agcgaaagcaggcaaaccatttgaatggatgtcaatccgaccttactttcttaaaagtgccagcacaaaatgctataagcacaactttcccttatact
ggagaccctccttacagccatgggacaggaacaggatacaccatggatactgtcaacaggacacatcagtactcagaaaagggaagatggacaac
aaaacaccgaaactggagcaccgcaactcaacccgattgatgggccactgccagaagacaatgaaccaagtggttatgcccaaacagattgtgtatt
ggaggcgatggctttccttgaggaatcccatcctggtattttgaaaactcgtgtattgaaacgatggaggttgttcagcaaacacgagtagacaagct
gacacaaggccgacagacctatgactggactctaaatagaaaccaacctgctgcaacagcattggccaacacaatagaagtgttcagatcaaatgg
cctcacggccaatgagtctggaaggctcatagacttcctaaggatgtaatggagtcaatgaacaaagaagaaatggggatcacaactcattttcag
agaaagagacgggtgagagacaatatgactaagaaaatgataacacagagaacaatgggtaaaagaagcagagattgaacaaaaggagttat
ctaattagagcattgaccctgaacacaatgaccaaagatgctgagagaggggaagctaaaacggagagcaattgcaaccccagggatgcaaataa
ggggtttgtatactttgtgagacactggcaaggagtatatgtgagaaacttgaacaatcaggggttgccagttggaggcaatgagaagaaagcaaa
gttggcaaatgttgtaaggaagatgatgaccaattctcaggacaccgaacttttctttcaccatcactggagataacaccaaatggaacgaaaatcag
aatcctcggatgtttttggccatgatcacatatatgaccagaaatcagcccgaatggttcagaaatgttctaagtattgctccaataatgttctcaaaca
aaatggcgagactggaaaagggtatatgtttgagagcaagagtatctagaactcaaatacctgcagaaatgctagcaagcatcgatttga
aatatttcaatgattcaacaagaaagaagattgaaaaaatccgaccgctcttaatagaggggactgcatcattgagccctgaatgatgatgggcat
gttcaatatgttaagcactgtattaggcgtctccatcctgaatcttggacaaaagagatacaccaagactacttactggtgggatggtcttcaatcctct
gacgattttgctctgattgtgaatgcacccaatcatgaagggattcaagccggagtcgacaggttttatcgaacctgtaagctacttggaatcaatatg
agcaagaaaaagtcttacataaacagaacaggtacatttgaattcacaagtttttctatcgttatgggttttgtgccaatttcagcatggagcttccca
gttttggggtgtctgggatcaacgagtcagcggacatgagtattggagttactgtcatcaaaaacaatatgataaacaatgatcttggtccagcaaca
gctcaaatggcccttcagttgttcatcaaagattacaggtacacgtaccgatgccatataggtgacacacaaatacaaacccgaagatcattgaaat
aaagaaactgtgggagcaaacccgttccaaagctggactgctggtctccgacggaggcccaaatttataaacattagaaatctccacattcctgaa
gtctgcctaaaatgggaattgatgatgaggattaccagggcgtttatgcaaccactgaaccccatttgtcagccataaagaaattgaatcaatgaa
caatgcagtgatgatgccagcacatgtccagccaaaaacatggagtatgatgcgttgcaacaacacactcctggatcccaaaagaaatcgatc
catcttgaatacaagtcaaagaggagtacttgaggatgaacaaatgtaccaaaggtgctgcaatttatttgaaaaattcttccccagcagttcataca
gaagaccagtcgggatatccagtatgtggaggctatgtttccagagcccgaattgatgcacggattgatttcgaatctggaaggataaagaaga
agagttcactgagatcatgaagatctgttccaccattgaagagctcagacgcaaaaatagtgaatttagcttgtcttcatgaaaaatgccttgttt
ctact

SEQ ID NO: 15

FIG. 8 (cont.)

PA agcgaaagcagggtactgatccaaaatggaagattttgtgcgacaatgcttcaatccgatgattgtcgagcttgcggaaaaaacaatgaaagagtat
ggggaggacctgaaaatcgaaacaaacaaaatttgcagcaatatgcactcacttggaagtatgcttcatgtattcagattttcacttcatcaatgagc
aaggcgagtcaataatcgtagaacttggtgatccaaatgcacttttgaagcacagatttgaaataatcgagggaagagatcgcacaatggcctgga
cagtagtaaacagtatttgcaacactacaggggctgagaaaccaaagtttctaccagatttgtatgattacaaggagaatagattcatcgaaattgg
agtaacaaggagagaagttcacatatactatctggaaaaggcaataaaattaaatctgagaaaacacacatccacattttctcgttcactgggga
agaaatggccacaaaggcagactacactctcgatgaagaaagcagggctaggatcaaaaccagactattcaccataagacaagaaatggccag
cagaggcctctgggattcctttcgtcagtccgagagaggagaagagacaattgaagaaaggtttgaaatcacaggaacaatgcgcaagcttgccg
accaaagtctcccgccgaacttctccagccttgaaaatttagagcctatgtggatggattcgaaccgaacggctacattgagggcaagctgtctca
aatgtccaaagaagtaaatgctagaattgaaccttttttgaaaacaacaccacgaccacttagacttccgaatgggcctccctgttctcagcggtcc
aaattcctgctgatggatgccttaaaattaagcattgaggacccaagtcatgaaggagagggaataccgctatatgatgcaatcaaatgcatgaga
acattcttggatgaaggaacccaatgttgttaaaccacacgaaaagggaataaaatccaaattatcttctgtcatgaagcaagtactggcagaa
ctgcaggacattgagaatgaggagaaaattccaaagactaaaaatatgaagaaaacaagtcagctaaagtgggcacttggtgagaacatggcac
cagaaaaggtagactttgacgactgtaaagatgtaggtgatttgaagcaatatgatagtgatgaaccagaattgaggtcgctagcaagttggattc
agaatgagtttaacaaggcatgcgaactgacagattcaagctggatagagctcgatgagattggagaagatgtggctccaattgaacacattgcaa
gcatgagaaggaattatttcacatcagagggtgtctcactgcagagccacagaatacataatgaaggggggtgtacatcaatactgccttgcttaatgc
atcttgtgcagcaatggatgatttccaattaattccaatgataagcaagtgtagaactaaggagggaaggcgaaagaccaacttgtatggtttcatc
ataaaaggaagatcccacttaaggaatgacaccgacgtggtaaactttgtgagcatggagttttctctcactgacccaagacttgaaccacataaat
gggagaagtactgtgttcttgagataggagatatgcttataagaagtgccataggccaggtttcaaggcccatgttcttgtatgtgagaacaaatgg
aacctcaaaaattaaaatgaaatggggaatggaaatgaggccgttgcctcctccagtcacttcaacaaaattgagagtatgattgaagctgagtcctct
gtcaaagagaaagacatgaccaaagagttctttgagaacaaatcagaaacatggcccattggagagtccccaaaggagtggaggaaagttcca
ttgggaaggtctgcaggactttattagcaaagtcggtattcaacagcttgtatgcatctccacaactagaaggattttcagctgaatcaagaaactg
ctcttatcgttcaggctctaggacaaccttgaacctggaccttttgatcttgggggggctatatgaagcaattgaggagtgcctgattaatgatccc
tgggttttgcttaatgcttcttggttcaactccttccttacacatgcattgagttagttggcagtgctactatttgctatccatactgtcaaaaaagta
ccttgtttctact

SEQ ID NO: 16

NP agcaaaagcagggtagataatcactcactgagtgacatcaaaatcatggcgtcccaaggcaccaaacggtcttacgaacagatgggagactgatg
gagaacgccagaatgccactgaaatcagagcatccgtcggaaaaatgattggtggaattggacgattctacatccaaatgtgcaccgaactcaaa
ctcagtgattatgagggacggttgatccaaaacagcttaacaatagagagaatggtgctctctgcttttgacgaaaggagaaataaatacctggaa
gaacatcccagtgcggggaaagatcctaagaaaactggaggacctatatacaggagagtaaacggaaagtggatgagagaactcatccttatg
acaaagaagaaataaggcgaatctggcgccaagctaataatggtgacgatgcaacggctggtctgactcacatgatgatctggcattccaatttga
atgatgcaacttatcagaggacaagagctcttgttcgcaccggaatggatcccaggatgtgctctctgatgcaaggttcaactctcccctaggaggtct
ggagccgcaggtgctgcagtcaaaggagttggaacaatggtgatggaattggtcaggatgatcaaacgtgggatcaatgatcggaacttctggag
gggtgagaatggacgaaaaacaagaattgcttatgaaagaatgtgcaacattctcaaagggaaatttcaaactgctgcacaaaaagcaatgatg
gatcaagtgagagagagcggaaacccagggaatgctgagttcgaagatctcactttttctagcacggtctgcactcatatattgagagggtcggttgctc
acaagtcctgcctgcctgcctgtgtgatggacctgccgtagccagtggggtacgactttgaaagagaggggatactctctagtcggaatagaccctttc
agactgccttcaaaacagccaagtgtacagcctaatcagaccaaatgagaatccagcacacaagagtcaactggtgtggatggcatgccattctgc
cgcatttgaagatctaagagtattaagcttcatcaaagggacgaaggtgctcccaagagggaagctttccactagaggagttcaaattgcttccaat
gaaaatatggagactatgaatcaagtacacttgaactgagaagcaggtactgggccataaggaccagaagtggaggaaacaccaatcaacag
agggcatctgcgggccaaatcagcatacaacctacgttctcagtacagagaaatctcccttttgacagaacaaccattatggcagcattcaatggg
aatacagagggaagaacatctgacatgagggaccgaaatcataaggatgatggaaagtgcaagaccagaagatgtgtctttccaggggcgggga
gtcttcgagctctcggacgaaaaggcagcgagcccgatcgtgccttcctttgacatgagtaatgaaggatcttatttcttcggagacaatgcagagg
agtacgacaattaaagaaaaataccccttgtttctact

SEQ ID NO: 17

FIG. 8 (cont.)

M agcgaaagcaggtagatattgaaagatgagtcttctaaccgaggtcgaaacgtacgtactctctatcatcccgtcaggcccctcaaagccgagat
cgcacagagacttgaagatgtctttgcagggaagaacactgatcttgaggttctcatggaatggctaaagacaagaccaatcctgtcacctctgact
aaggggattttaggatttgtgttcacgctcaccgtgcccagtgagcgaggactgcagcgtagacgctttgtccaaaatgcccttaatgggaacgggg
atccaaataacatggacaaagcagttaaactgtataggaagctcaagagggagataacattccatggggccaaagaaatctcactcagttattctg
ctggtgcacttgccagttgtatgggcctcatatacaacaggatggggctgtgaccactgaagtggcatttggcctggtatgtgcaacctgtgaaca
gattgctgactcccagcatcggtctcataggcaaatggtgacaacaaccaatccactaatcagacatgagaacagaatggttttagccagcactac
agctaaggctatggagcaaatggctggatcgagtgagcaagcagcagaggccatggaggttgctagtcaggctagacaaatggtgcaagcgatg
agaaccattgggactcatcctagctccagtgctggtctgaaaaatgatcttcttgaaaatttgcaggcctatcagaaacgaatgggggtgcagatgc
aacggttcaagtgatcctctcgctattgccgcaaatatcattgggatcttgcacttgatattgtggattcttgatcgtctttttttcaaatgcatttaccgt
cgctttaaatacggactgaaaggagggccttctacggaaggagtgccaaagtctatgagggaagaatatcgaaaggaacagcagagtgctgtgg
atgctgacgatggtcattttgtcagcatagagctggagtaaaaaactaccttgtttctact

SEQ ID NO: 18

HA

AGCAAAAGCAGGGGAAAATAAAAACAACCAAAatgaaggcaatactagtagttctgctatatacatttgcaaccg
caaatgcagacacattatgtataggttatcatgcaaacaattcaacagacacactgtagacacagtactagaaaagaatgtaacagt
aacacactctgttaaccttctagaagacaagcataacggggaaactatgcaaactaagaggggtagccccattgcatttgggtaa
atgtaacattgctggctggatcctgggaaatccagagtgtgaatcactctccacagcaagttcatggtcctacattgtggaaacat
ctagttcagacaatggaacgtgttacccaggagatttcatcaattatgaggagctaagagagcaattgagctcagtgtcatcatttg
aaaggtttgagatattccccaaaacaagttcatggcccaatcatgactcgaacaaaggtgtaacggcagcatgtcctcacgctgg
agcaaaaagcttctacaaaaatttaatatggctagttaaaaaaggaaattcatacccaaagctcagccaatcctacattaatgat
aaagggaaagaagtcctcgtgctgtgggcattcaccatccatctactactgctgaccaacaaagtctctatcagaatgcagatg
catatgttttgtggggacatcaagatacagcaagaagttcaagccggaaatagcaataagacccaaagtgagggatcaagaag
ggagaatgaactattactggacactagtagagccgggagacaaaataacattcgaagcaactggaaatctagtggtaccgagat
atgcattcacaatggaaagaaatgctggatctggtattatcatttcagatacaccagtccacgattgcaatacaacttgtcagaca
cccgagggtgctataaacaccagcctcccatttcagaatatacatccgatcacaattggaaaatgtccaaagtatgtaaaaagca
caaaattgagactggccacacaggattgaggaatgtcccgtctattcaatctagaggcctattcggggccattgccggcttcattgaa
ggggggtggacagggatggtagatggatggtacggttatcaccatcaaaatgagcaggggtcaggatatgcagccgacctgaa
gagcacacaaaatgccattgacaagattactaacaaagtaaactctgttattgaaaagatgaatacacagttcacagcagtgggt
aaagagttcaaccacctggaaaaaagaataagagaatttaaataaaaaagttgatgatggtttcctggacatttggacttacaatg
ccgaactgttggttctattggaaaatgaaagaacttttggactaccatgattcaaatgtgaagaacttgtatgaaaaggtaagaaa
ccagtaaaaaacaatgccaaggaaattggaaacggctgctttgaattttaccacaaatgcgataacacgtgcatggaaagtgtc
aaaaatgggacttatgactacccaaaatactcagaggaagcaaaattaaacagagaaaaaatagatggggtaaagctggaat
caacaaggatttaccagattttggcgatcattcaactgtcgccagttcattggtgctggtagtctcccggggggcaatcagcttctg
gatgtgctctaatgggtctctacagtgtagaatatgtatttaaGATTAGAATTTCAGAGATATGAGGAAAAACACCC
TTGTTTCTACT

SEQ ID NO: 19

FIG. 8 (cont.)

NA
AGCAAAAGCAGGGGAAAATAAAAACAACCAAAatgaaggcaatactagtagttctgctatatacatttgcaaccgcaaa
tgcagacacattatgtataggttatcatgcaaacaattcaacagacactgtagacacagtactagaaaagaatgtaacagtaacacact
ctgttaaccttctagaagacaagcataacgggaaactatgcaaactaagagggggtagccccattgcatttgggtaaatgtaacattgctg
gctggatcctgggaaatccagagtgtgaatcactctccacagcaagttcatggtcctacattgtggaaacatctagttcagacaatggaa
cgtgttacccaggagatttcatcaattatgaggagctaagagagcaattgagctcagtgtcatctttgaaaggtttgagatattccccaa
aacaagttcatggcccaatcatgactcgaacaaaggtgtaacggcagcatgtcctcacgctggagcaaaaagcttctacaaaaatttaa
tatggctagttaaaaaaggaaattcatacccaaagctcagccaatcctacattaatgataaagggaaagaagtcctcgtgctgtggggc
attcaccatccatctactactgctgaccaacaaagtctctatcagaatgcagatgcatatgttttgtggggacatcaagatacagcaaga
agttcaagccggaaatagcaataagacccaaagtgagggatcaagaagggagaatgaactattactggacactagtagagccgggag
acaaaataacattcgaagcaactggaaatctagtggtaccgagatatgcattcacaatggaaagaaatgctggatctggtattatcattt
cagatacaccagtccacgattgcaatacaacttgtcagacaccccgagggtgctataaacaccagcctcccatttcagaatatacatccga
tcacaattggaaaatgtccaaagtatgtaaaaagcacaaaattgagactggccacagagattgaggaatgtcccgtctattcaatctaga
ggcctattcggggccattgccggcttcattgaaggggggtggacagggatggtagatggatggtacggttatcaccatcaaaatgagca
ggggtcaggatatgcagccgacctgaagagcacacaaaatgccattgacaagattactaacaaagtaaactctgttattgaaaagatg
aatacacagttcacagcagtgggtaaagagttcaaccacctggaaaaaagaatagagaatttaaataaaaaagttgatgatgtttcct
ggacatttggacttacaatgccgaactgttggttctattggaaaatgaaagaactttggactaccatgattcaaatgtgaagaacttgtat
gaaaaggtaagaaaccagttaaaaaacaatgccaaggaaattggaaacggctgctttgaattttaccacaaatgcgataacacgtgca
tggaaagtgtcaaaaatggacttatgactacccaaaatactcagaggaagcaaaattaaacagagaaaaaatagatggggtaaagc
tggaatcaacaaggattttaccagattttggcgatcatttcaactgtcgccagttcattggtgctggtagtctccctggggggcaatcagcttc
tggatgtgctctaatgggtctctacagtgtagaatatgtatttaaGATTAGAATTTCAGAGATATGAGGAAAAACACCCTT
GTTTCTACT

SEQ ID NO: 20

NS
AGCAAAAGCAGGGTGACAAAGACATAATGGATCCAAACACTGTGTCAAGCTTTCAGGTAGATTGCTTTCTTTGG
CATGTCCGCAAACGAGTTGCAGACCAAGAACTAGGTGATGCCCCATTCCTTGATCGGCTTCGCCGAGATCAGAA
ATCCCTAAGAGGAAGGGGCAGCACTCTTGGTCTGGACATCGAGACAGCCACACGTGCTGGAAAGCAGATAGTG
GAGCGGATTCTGAAAGAAGAATCCGATGAGGCACTTAAAATGACCATGGCCTCTGTACCTGCGTCGCGTTACCTA
ACCGACATGACTCTTGAGGAAATGTCAAGGGAATGGTCCATGCTCATACCCAAGCAGAAAGTGGCAGGCCCTCT
TTGTATCAGAATGGACCAGGCGATCATGggaggaggtttcttcggagctattgctggtttcttggaaggaggatgggaaggaatgatt
gcaggttgggaggaagagagagccggaacccagggaatgcttgataataagcggccgcAGTGTGATTTTTGACCGGCTGGAGAC
TCTAATATTGCTAAGGGCTTTCACCGAAGAGGGAGCAATTGTTGGCGAAATTTCACCATTGCCTTCTCTTCCAGG
ACATACTGCTGAGGATGTCAAAAATGCAGTTGGAGTCCTCATCGGAGGACTTGAATGGAATGATAACACAGTTC
GAGTCTCTGAAACTCTACAGAGATTCGCTTGGAGAAGCAGTAATGAGAATGGGAGACCTCCACTCACTCCAAAA
CAGAAACGAGAAATGGCGGGAACAATTAGGTCAGAAGTTTGAAGAAATAAGATGGTTGATTGAAGAAGTGAG
ACACAAACTGAAGGTAACAGAGAATAGTTTTGAGCAAATAACATTTATGCAAGCCTTACATCTATTGCTTGAAGT
GGAGCAAGAGATAAGAACTTTCTCATTTCAGCTTATTTAATAATAAAAAACACCCTTGTTTCTACT

SEQ ID NO: 21

FIG. 9
(A) A/California/07/09pdm
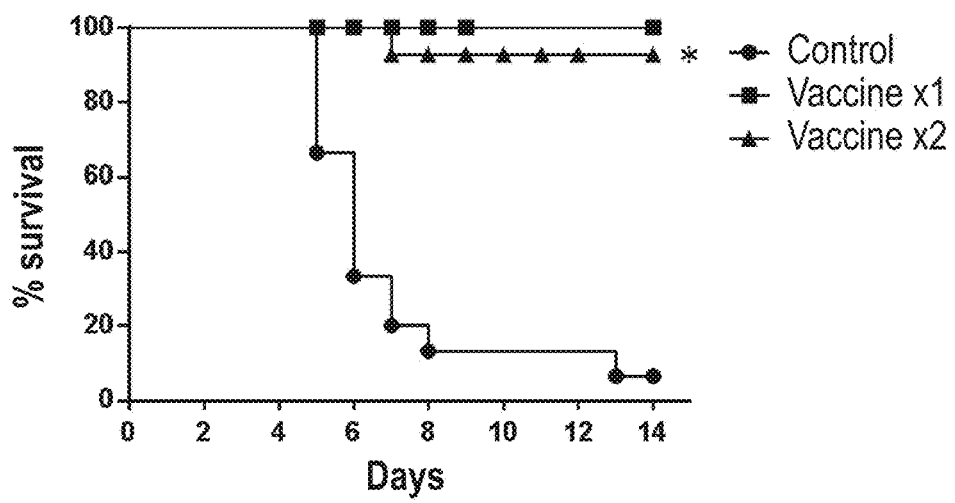
(B) A/Aichi/2/68 (H3N2)
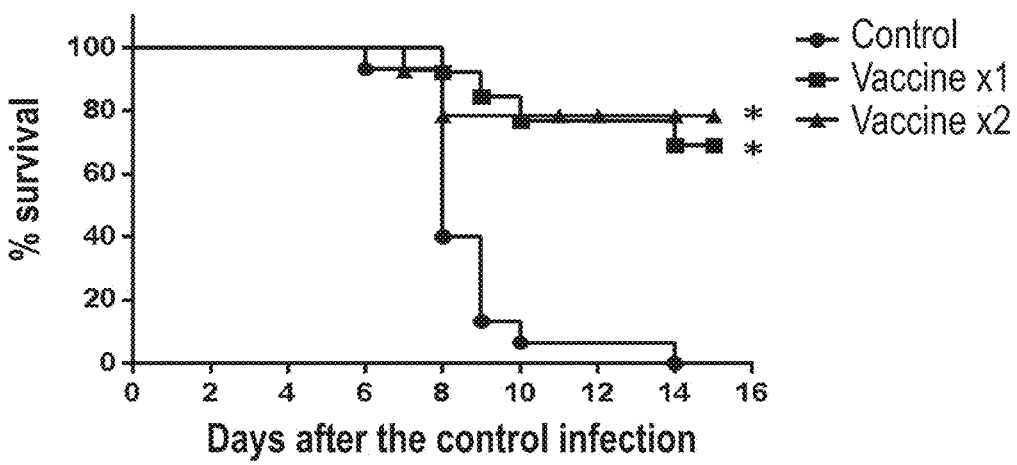

FIG. 9 (cont.)
(C)
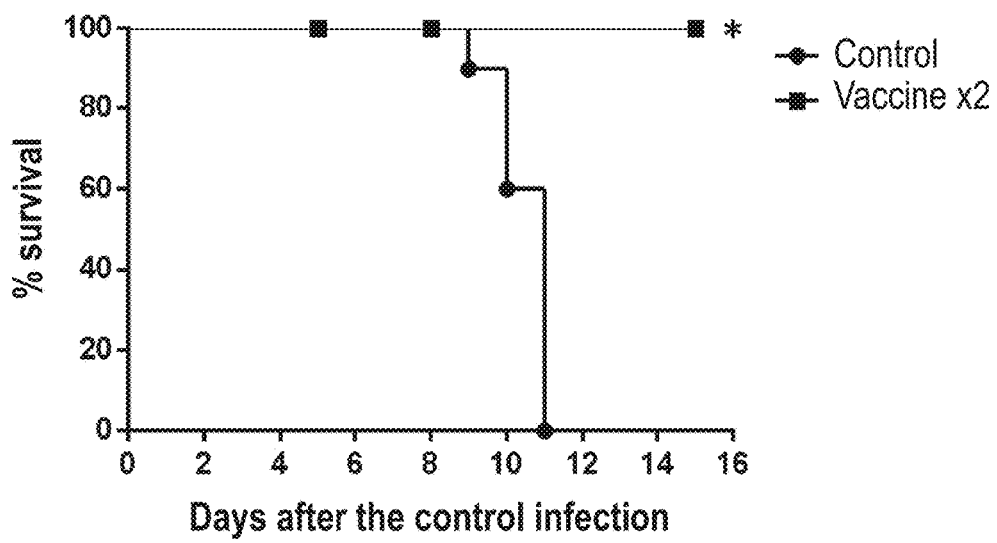
A/Mississippi/85/1 (H3N2)
(D)
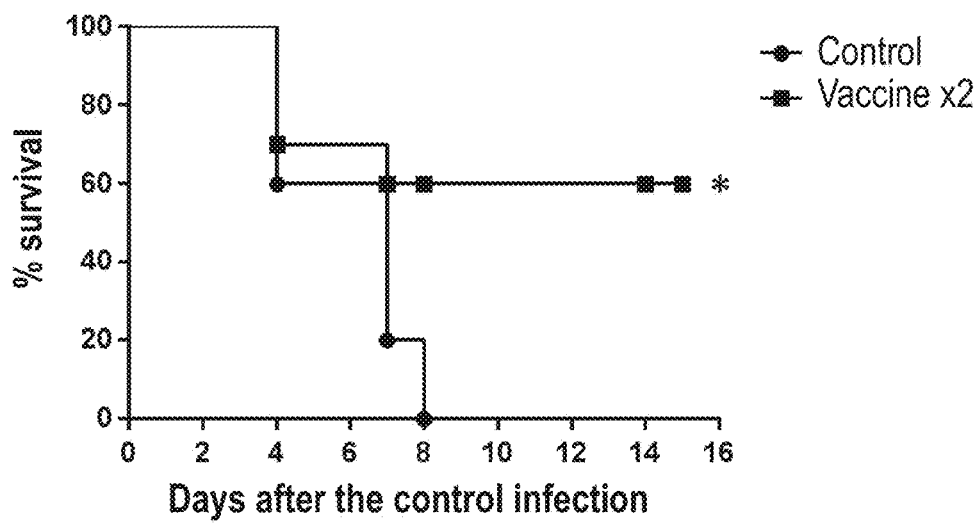
B/Lee/40

FIG. 10
(A)
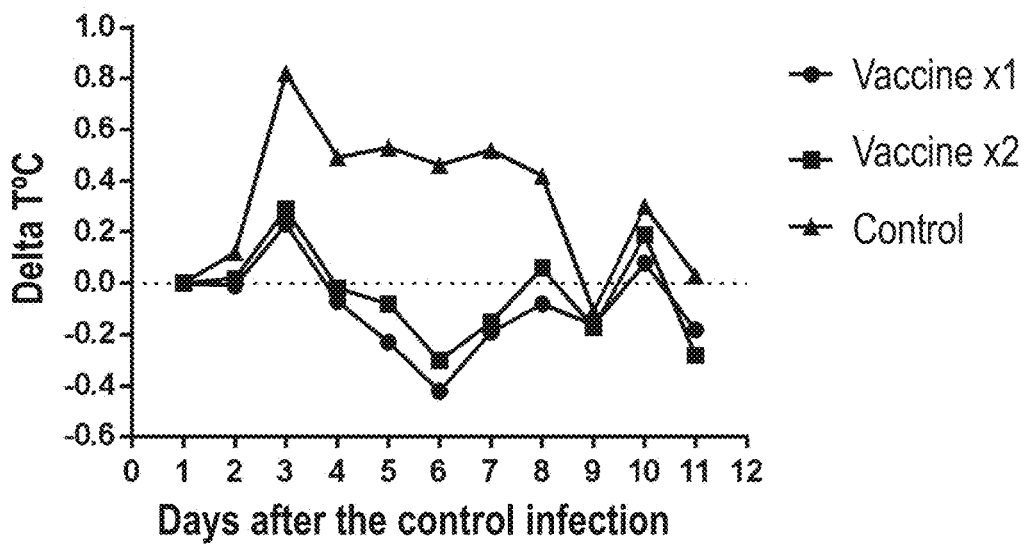
(B)
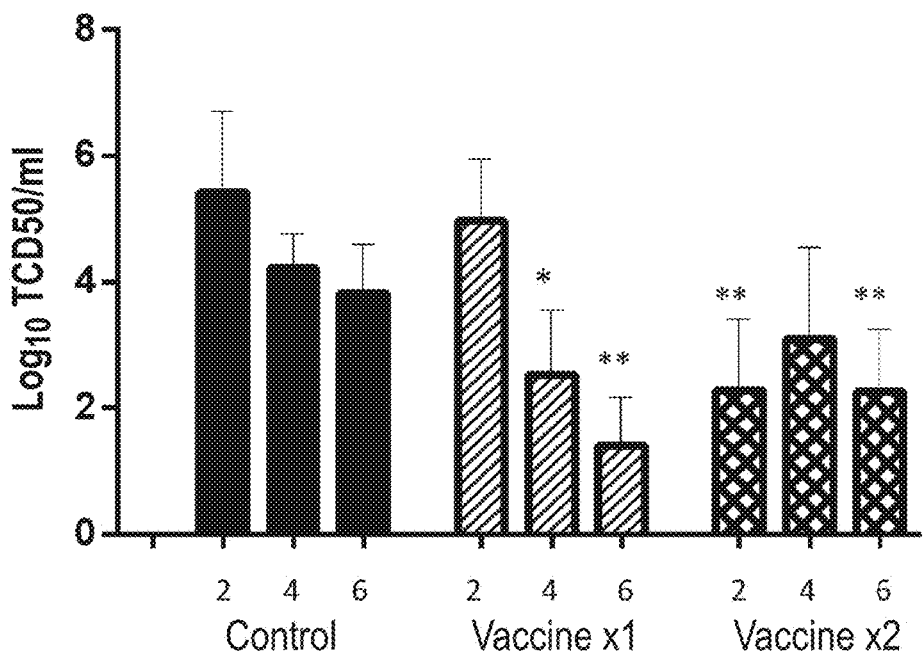

ATTENUATED INFLUENZA VECTORS FOR THE PREVENTION AND/OR TREATMENT OF INFECTIOUS DISEASES AND FOR THE TREATMENT OF ONCOLOGICAL DISEASES

CROSS REFERENCE TO RELATED APPLICATIONS

This application is a national stage application under 35 USC 371 of International Application No. PCT/RU2016/050066, filed Nov. 3, 2016, which claims priority to Russian Patent Application No. 2015147703, filed Nov. 6, 2015, the entire contents of each of which are incorporated herein by reference.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 726932000700SEQLIST.txt, date recorded: Sep. 19, 2017, size: 42 KB).

FIELD OF THE INVENTION

The present invention relates to the field of medicine and virology, in particular, to an attenuated chimeric A virus, an attenuated influenza vector based thereon, and their use for the prevention and/or treatment of infectious diseases and for the treatment of oncological diseases.

BACKGROUND

Today, the most important protective measure against a viral infection and for limiting its spread is preventive vaccination. Modern vaccines, as a rule, induce the formation of antibodies to surface viral antigens. Vaccine effectiveness directly depends on the degree of matching between the antigenic structure of the virus strains containing in a vaccine and the strains circulating in the population. Surface proteins of the majority of viruses undergo constant antigenic variation (antigenic drift), necessitating constant updating of vaccine strain composition. The development of highly immunogenic and safe vaccines inducing the immune response of a broad spectrum of action is currently one of the major problems encountered in efficient influenza prevention.

Of all the viral respiratory diseases, influenza causes the most severe pathology and leads to the greatest damage to the population health and economy. The lack of population immunity to the periodically emerging new pandemic influenza strains makes influenza infection especially dangerous. It is known that the Spanish flu caused the death of 30 to 50 million people in 1918. Currently, according to the World Health Organization (WHO) data, each year approximately 20% of the population worldwide, including 5-10% of adults and 20-30% of children, become ill with influenza during seasonal epidemics (World Health Organization) at the website www.who.int under the directory biologicals/vaccines/influenza/en/ (accessed date: 28.03.2016)). Severe disease forms are recorded for 3-5 million cases, and 250,000 to 500,000 cases are lethal. Economic losses caused by influenza and other acute respiratory viral infections (ARVI) account for approximately 77% of the total damage from all infectious diseases. Significant losses are related both to the direct costs of patients' treatment and rehabilitation, as well as to the indirect losses caused by a decrease in productivity and reduction in corporate profits. Influenza and acute respiratory viral infections account for 12-14% of the total number of temporary disability cases.

The existing vaccines can be subdivided into two types: the attenuated (live, containing whole and active viruses exhibiting low pathogenicity) and inactivated (containing fragments of viral particles or whole inactive viruses) types. Live viruses that can replicate in an infected host elicit a strong and long-lasting immune response against the expressed antigens of these viruses. They effectively induce both humoral and cellular immune responses, and stimulate cytokine- and chemokine-mediated immune responses. Therefore, live attenuated viruses have certain advantages over vaccine compositions based on either inactivated immunogens or separate subunits of an immunogen, which generally stimulate only the humoral part of the immune system.

For vaccination of animals and humans from various infectious diseases, viruses of different families can be used as vectors expressing foreign genomic sequences. Vectors can be used in the cases where traditional killed or live vaccines cannot be produced or their effectiveness does not allow control of a disease. Among the existing antigen delivery systems, viral vectors occupy a special place because of the following properties: they have a natural mechanism of interaction with a cell and penetration into it, transfer foreign genetic material to the cytoplasm or nucleus of a cell, and are able to provide long-lasting expression of an antigen, and the viral envelope protects the nucleic acid encoding an introduced transgene.

Not all viruses have the properties necessary to construct vectors for the production of effective attenuated recombinant vaccines. Currently, for the development of viral vector-based vaccines, most widely used viruses are poxviruses (Poxviridae) [J. Gen. Virol. 2005. V. 86. No. 11. P. 2925-2936], Newcastle disease virus (NDV) [Virol. 2001. V. 75. No. 23. P. 11868-11873] and adenoviruses (Adenoviridae) [Biotechnology. 2007. V. 5, P. 38-44]. Among the poxviruses used as a viral vector, the most popular virus is vaccinia virus having advantages, such as simplicity and low cost of production, as well as a high packing capacity (up to 25 kbp) [J. Gen. Virol. 2005. V. 86. No. 11. P. 2925-2936]. A serious disadvantage of vaccinia virus-based vectors is pre-existing immunity to this virus, which is present in a part of the human population as a result of immunization against smallpox. Therefore, it is advisable to use vectors based on poxviruses, such as canarypox (Canarypox) and poultry poxvirus (Flowpox). However, Canarypox and Flowpox induce weaker immune response to target antigens than the vaccinia virus and require repeated administration or use of adjuvants [Vaccine. 1991. V. 9. No. 5, P. 303-308]. A significant disadvantage of a NDV vaccine vector is that the effects of the administration of recombinant NDVs have not been sufficiently studied, and it is not clear whether NDV-based vaccines are safe for humans. In addition, NDV is characterized by a low packing capacity and difficulty in producing vectors carrying several target antigens [Chem. Biodivers. 2010. V. 7. No. 3. P. 677-689]. Adenoviruses also have a number of disadvantages limiting their use as vectors for gene transfer. The major disadvantages of adenoviral vectors are the following: (1) heterogeneous distribution of the viral receptors on the surface of cells in the body, which makes many cells insensitive to adenovirus infection; (2) the presence of a powerful protective immunity of the population to known adenoviral vectors; and (3) a theoretical possibility of integration of the adenovirus DNA genome into human chromosomes (Stephen S L, Montini E, Sivanandam V G, Al-Dhalimy M, Kestler H A, Finegold M, Grompe M, Kochanek S. Chromosomal integration of adenoviral vector DNA in vivo. J Virol. 2010 October; 84(19):9987-94. doi: 10.1128/JVI.00751-10. Epub 2010 Aug. 4).

Vectors constructed based on influenza virus have several advantages over other viral vectors, because:
- influenza viruses do not have a DNA phase in their replication cycle and cannot be inserted into the human or animal genome;
- influenza virus elicits systemic and mucosal B- and T-cell responses to its antigens upon infection of human respiratory tract cells;
- there are available multiple different influenza virus subtypes. Since antibodies to said various subtypes do not have cross-reactivity, it is possible to avoid pre-existing immunity to a viral vector in a host, which is often a problem with other live vectors. Effective booster immunizations are also possible with various influenza virus subtypes that express the same antigens;
- there are several types of live influenza vaccines for intranasal administration (LIVE allantoic INFLUENZA VACCINE ULTRAVAC® (RF) and Flumist® (USA)) and industrial technology of their production by using 10-day-old chicken embryos (Guideline on Influenza Vaccines—Quality Module, European Medicines Acency, 25 Apr. 2014 [electronic resource] at the website www.ema.europa.eu under the directory docs/en_GB/document library/Scientific_guideline/2014/06/WC500167817.pdf (accessed date: 11, Jan. 2015)).

The influenza virus belongs to the family of Orthomyxoviridae, which includes genera: influenza A, B, and C viruses. Genomes of influenza A and B viruses are structurally similar, and consist of eight RNA genome segments of negative polarity: PB2, PB1, PA, HA, NA, NP, M and NS (Chou Y Y, Vafabakhsh R, Doğanay S, Gao Q, Ha T, Palese P. One influenza virus particle packages eight unique viral RNAs as shown by FISH analysis. Proc Natl Acad Sci USA. 2012 Jun. 5; 109(23):9101-6. doi: 10.1073/pnas.1206069109. Epub 2012 Apr. 30). The polymerase complex PB2, PB1, and PA transcribes one mRNA from each genomic fragment, which is translated to the protein of the same name. Messenger RNAs of genomic segments M and NS may be alternatively spliced to form mRNAs encoding M2 and NEP proteins, respectively. All proteins except NS1 and PB1-F2 (are available not in all strains) are structural components of a virus particle. Nonstructural protein NS1 accumulates in the cytoplasm of infected cells and acts as an interferon inhibitor (Krug R M. Functions of the influenza A virus NS1 protein in antiviral defense. Curr Opin Virol. 2015 June; 12:1-6. doi: 10.1016/j.coviro.2015.01.007. Epub 2015 Jan. 29. Review).

The segmented structure of the influenza virus genome is an source of new different strains that are the result of the reassortment process. This is one of the mechanisms for the natural antigenic diversity of influenza viruses and the occurrence of influenza pandemics.

The antigenic properties of influenza virus are determined by the surface glycoproteins—hemagglutinin (HA) and neuraminidase (NA) that form spikes on the virion surface. The HA molecule is responsible for the mechanisms of binding the virus to sialic acid receptors on a cell and fusing the viral and cell membranes for penetration of the genome into the cytoplasm and nucleus of the cell. In the process of viral replication, the HA is cleaved (HA activation) by cellular proteases into two subunits—HA1 and HA2—that remain connected by a disulfide bond (Bullough P A, Hughson F M, Skehel J J, Wiley DC. Structure of influenza haemagglutinin at the pH of membrane fusion. Nature 1994; 371, 37-43). The HA molecule consists of two parts: a globular part comprising HA1 subunit and the stem region, which is formed mainly by HA2 and partially by the HA1 subunit. The globular part includes a receptor-binding site and five antigenic sites, and serves as the main target for the formation of antibodies. Antibodies that block virus binding to the cell receptor are neutralizing. The HA1 subunit is characterized by high variability. The HA stem that is located in close proximity to the viral membrane is highly conservative and characterized by low immunogenicity. The main function of the HA2 subunit is to ensure the fusion of the viral and the endosomal membranes; this subunit is highly conserved. According to the antigenic specificity, 18 subtypes of HA and 11 subtypes of NA are known to date for the influenza A virus. The subtypes H1, H2, H5, H6, H8, H9, H11, H12, H13, H16, H17, and H18 belong to the first group, and the subtypes H3, H4, H7, H10, H14, and H15 belong to the second group. At the same time, only the subtypes H1, H2, and H3 of influenza virus A and different antigenic variants of influenza virus B, which are circulating in the human population, are causing the pandemics and seasonal influenza epidemics.

The specific immunity generated after the disease or after vaccination by one influenza A virus subtype poorly protects from infection by the other virus subtypes. The immunity to any influenza virus A subtype does not protect from the infection by influenza virus B, and vice versa—immunization against the influenza virus B is not effective in regard to influenza virus A. In this regard, there is an urgent need for the development of a universal influenza vaccine effective against all known antigenic varieties of influenza A and B viruses.

Two mechanisms enable the extremely high variability of the influenza virus and, therefore, its ability to escape from the neutralizing antibodies: 1) accumulation of the point mutations leading to the change in the antigenic structure of the surface glycoproteins (antigenic drift) and 2) reassortment of the genomic segments. They lead to the emergence of new subtypes of viruses (antigenic shift) that can cause pandemics.

All of the existing influenza vaccines have low efficiency in elderly and infants (Jefferson T, Rivetti A, Di Pietrantonj C, Demicheli V, Ferroni E. Vaccines for preventing influenza in healthy children. Cochrane Database Syst Rev 2012; 8, CD004879; Osterholm M T, Kelley N S, Sommer A, Belongia E A. Efficacy and effectiveness of influenza vaccines: a systematic review and meta-analysis. Lancet Infect Dis 2011; 12, 36-44; Pfleiderer M, Trouvin J H, Brasseur D, Granstrom M, Shivji R, Mura M, Cavaleri M. Summary of knowledge gaps related to quality and efficacy of current influenza vaccines. Vaccine 2014; 32, 4586-91). Furthermore, these vaccines can protect against the circulating virus only if the vaccine virus has the same antigenic properties as the epidemic strain. It is the high variability of the surface antigens of influenza virus—HA and NA—that necessitates annual vaccination and the updating of vaccine composition. It should be mentioned that seasonal vaccines that are developed according to the WHO recommendations are not effective in the case of the occurrence of a new influenza pandemic virus strain that is fundamentally different from all of the circulating strains, as it happened in 2009 when the pandemic virus A/California/7/2009 (H1N1pdm09) emerged. One more example could be the low efficiency of the H3N2 component of the seasonal vaccine 2014 due to the emergence of the new antigenic variant of this virus subtype as a result of antigenic drift (Skowronski D M, Chambers C, Sabaiduc S, De Serres G, Dickinson J A, Winter A L, Drews S J, Fonseca K, Charest H, Gubbay J B, Petric M, Krajden M, Kwindt T L, Martineau C, Eshaghi A, Bastien N, Li Y. Interim estimates of 2014/15 vaccine effectiveness against influenza A(H3N2) from Canada's Sentinel Physician Surveillance Network, January 2015. Euro Surveill 2015; 20). During the last 60 years, a lot of vaccines were developed that have certain advantages and shortcomings; however, none of the existing vaccines can solve the problem of influenza morbidity control because of their incapability of inducing cross-protective immunity to constantly evolving influenza viruses. In this regard, there is an urgent need for the development of an effective universal influenza vaccine that provides a long-lasting broad cross-protective immunity and is able to protect against the influenza A and B viruses of all known subtypes.

The function of all the known influenza vaccines inactivated (whole virion, split, or subunit) or live (attenuated cold adapted)—is to generate the immunity to the globular part of HA. In contrast to the variable globular part, the HA stem part of influenza A (groups I and II) and B viruses is much more conservative. There are known several mechanisms of direct and indirect neutralization for the antibodies induced to this part of HA. One of the mechanisms of direct neutralization contributes to the prevention of the HA conformational change that is necessary for the fusion peptide release and the subsequent fusion of the endosomal and viral membranes in order to deliver the viral genome into the cell. The second mechanism of the direct neutralization contributes to the prevention of HA cleavage to HA1 and HA2 subunits by antibodies interacting with the HA part that is located in the vicinity of the cleavage site. The antibody-dependent and complement-dependent cytotoxicity are involved in the mechanisms of indirect neutralization (Terajima M, Cruz J, Co M D, Lee J H, Kaur K, Wrammert J, Wilson P C, Ennis F A. Complement-dependent lysis of influenza a virus-infected cells by broadly cross-reactive human monoclonal antibodies. J Virol 2011; 85, 13463-7; Jegaskanda S, Weinfurter J T, Friedrich T C, Kent S J. Antibody-dependent cellular cytotoxicity is associated with control of pandemic H1N1 influenza virus infection of macaques. J Virol 2013; 87, 5512-22).

Vaccination practically does not induce the antibodies to the HA stem region, while after the natural infection a small quantity of these antibodies could be detected (Moody M A, Zhang R, Walter E B, Woods C W, Ginsburg G S, McClain M T, Denny T N, Chen X, Munshaw S, Marshall D J, Whitesides J F, Drinker M S, Amos J D, Gurley T C, Eudailey J A, Foulger A, DeRosa K R, Parks R, Meyerhoff R R, Yu J S, Kozink D M, Barefoot B E, Ramsburg E A, Khurana S, Golding H, Vandergrift N A, Alam S M, Tomaras G D, Kepler T B, Kelsoe G, Liao H X, Haynes B F. H3N2 influenza infection elicits more cross-reactive and less clonally expanded anti-hemagglutinin antibodies than influenza vaccination. PLoS ONE 2011; 6, e25797).

The majority of the currently being developed approaches to the generation of the universal vaccine are targeting the conservative regions of the influenza virus proteins. The antibodies directed to the conservative proteins PB2, PB1, PA, NP, and M1 do not have neutralizing activity but could play an important role in virus elimination by means of antibody-dependent cytotoxicity (ADCC).

Several examples of generating a universal vaccine are based on HA2 subunit. The triple immunization of mice with peptides representing the ectodomain HA2 (23-185 amino acid residues) or the fusion peptide (1-38 amino acid residues) conjugated to the (keyhole limpet hemocyanin) (KLH) and Freund adjuvants induced the cross-reactive immunity leading to a decrease in the animal mortality when challenged with a lethal dose of heterologous virus strain (Stanekova Z, Kiraly J, Stropkovska A, Mikuskova T, Mucha V, Kostolansky F, Vareckova E. Heterosubtypic protective immunity against influenza A virus induced by fusion peptide of the hemagglutinin in comparison to ectodomain of M2 protein. Acta Virol 2011; 55, 61-7). More effective protection was developed in the case of vaccination with chimeric HA constructs. Krammer et al. showed that heterosubtypic humoral immunity is induced in mice immunized with chimeric proteins, containing the HA globular parts from the viruses of different subtypes in combination with the HA stem region of the same virus (Krammer F, Palese P, Steel J. Advances in universal influenza virus vaccine design and antibody mediated therapies based on conserved regions of the hemagglutinin. Curr Top Microbiol Immunol 2014; 386, 301-21; Krammer F, Hai R, Yondola M, Tan G S, Leyva-Grado V H, Ryder A B, Miller M S, Rose J K, Palese P, Garcia-Sastre A, Albrecht R A. Assessment of influenza virus hemagglutinin stalk-based immunity in ferrets. J Virol 2014; 88, 3432-42). The complicated immunization scheme that includes the animals electroporation using DNA, and double intramuscular and intranasal immunization with the protein constructs supplemented with the adjuvant poly (I:C) are the shortcomings of this approach.

The use of stabilized structures (mini-HA) generated by means of gene engineering, based on the amino acid sequence of the HA stem region of the H1N1 virus, serves as an example of a different approach to the generation of the universal influenza vaccine. Only the structures with the highest affinity to the antibodies that have a broad range of neutralizing activity were selected from the large library. The immunization of mice with these structures also protected the animals from death when challenged with highly pathogenic avian influenza virus of H5N1 subtype (Impagliazzo A, Milder F, Kuipers H, Wagner M V, Zhu X, Hoffman R M, van Meersbergen R, Huizingh J, Wanningen P, Verspuij J, de Man M, Ding Z, Apetri A, Kukrer B, Sneekes-Vriese E, Tomkiewicz D, Laursen N S, Lee P S, Zakrzewska A, Dekking L, Tolboom J, Tettero L, van Meerten S, Yu W, Koudstaal W, Goudsmit J, Ward A B, Meijberg W, Wilson I A, Radosevic K. A stable trimeric influenza hemagglutinin stem as a broadly protective immunogen. Science 2015; 349, 1301-6). The complete protection of mice from death was achieved by the double intramuscular immunization with 30 µg of the purified mini-HA protein supplemented with the Matrix-M adjuvant produced by Novavax.

The other prospective direction in the development of the universal influenza vaccine is based on the design of the self-assembling nanoparticles that significantly enhance the immunogenic properties of HA (Kanekiyo M, Wei C J, Yassine H M, McTamney P M, Boyington J C, Whittle J R, Rao S S, Kong W P, Wang L, Nabel G J. Self-assembling influenza nanoparticle vaccines elicit broadly neutralizing H1N1 antibodies. Nature 2013; 499, 102-6). The animals were immunized 2 or 3 times intramuscularly with nanoparticles supplemented with the new adjuvant SAS (Sigma Adjuvant System). In spite of the lack of the neutralizing antibodies after immunization with nanoparticles, the mice as well as ferrets turned out to be completely protected from death when infected with a highly pathogenic H5N1 avian virus.

One of the modern technologies for the generation of live vaccine is based on the construction of vaccine vectors that enable to express the antigens of one virus by the other virus. Different DNA-containing viruses, namely: adenovirus, herpesvirus, baculovirus, or poxvirus, are used as the vectors for the expression of influenza antigens (Dudek T, Knipe D M. Replication-defective viruses as vaccines and vaccine vectors. Virology 2006; 344, 230-9; He F, Madhan S, Kwang J. Baculovirus vector as a delivery vehicle for influenza vaccines. Expert Rev Vaccines 2009; 8, 455-67; Draper S J, Cottingham M G, Gilbert S C. Utilizing poxviral vectored vaccines for antibody induction-progress and prospects. Vaccine 2013; 31, 4223-30. Price G E, Soboleski M R, Lo C Y, Misplon J A, Pappas C, Houser K V, Tumpey T M, Epstein S L. Vaccination focusing immunity on conserved antigens protects mice and ferrets against virulent H1N1 and H5N1 influenza A viruses. Vaccine 2009; 27, 6512-21). Thus, the experiments with the adenovirus vector showed that the triple immunization with plasmid (50 µg) containing the sequences of the influenza A virus conservative proteins NP and M2, followed by intranasal infection with the two adenovirus vectors that express the same proteins, led to the complete protection of the mice and ferrets infected with the virus A/FM/1/47 (H1N1) or with the highly pathogenic avian influenza virus H5N1 subtype, from death and weight loss.

Thus, all of the discussed approaches of targeting an immune response to the conservative regions of influenza virus antigens prove the possibility of the generation of a vaccine that will protect from infection with different variants of influenza A virus. However, complex schemes of multiple vaccinations of animals by using immunological adjuvants of different nature were used to achieve this goal. In addition, none of the known experimental preparations of a universal influenza vaccine provided protection against influenza B virus. It should be added to this that the above experimental preparations require complex technological processes for the production of multicomponent vaccines, associated with an unacceptably high cost of the final product.

Expression of antigens in cells of the nasal cavity is known to induce systemic and local mucosal B- and T-cell immune responses. Numerous attempts have been made to use influenza viruses as vectors for delivery and expression of foreign genomic sequences in cells of the respiratory tract of animals. Among 8 genomic fragments of influenza A or B viruses, only NS genomic fragment was capable of stably holding genomic insertions of more than 800 nucleotides in the reading frame of NS1 nonstructural protein, without disrupting the structure of the resulting virions (Kittel C, Sereinig S, Ferko B, Stasakova J, Romanova J, Wolkerstorfer A, Katinger H, Egorov A. Rescue of influenza virus expressing GFP from the NS1 reading frame. Virology. 2004 Jun. 20; 324(1):67-73. PubMed PMID: 15183054). Moreover, among all influenza virus proteins, only NS1 protein normally containing 230-237 amino acid residues can be truncated to 50% at the carboxyl end, without significantly affecting the reproductive activity of the virus in cell cultures, chicken embryos or in the respiratory tract of animals (Egorov A, Brandt S, Sereinig S, Romanova J, Ferko B, Katinger D, Grassauer A, Alexandrova G, Katinger H, Muster T. Transfectant influenza A viruses with long deletions in the NS1 protein grow efficiently in Vero cells. J Virol. 1998 August; 72(8):6437-41. PubMed PMID: 9658085; PubMed Central PMCID: PMC109801). This truncation of the NS1 protein provides a space for introduction of long insertions of foreign genomic sequences without disrupting the morphology and basic functions of the virus, thus making it possible to construct genetically stable vectors. In this regard, influenza virus vectors based on influenza A virus were produced that encoded a truncated reading frame of from 80 to 126 amino acid residues of the NS1 protein, wherein the truncated reading frame could be elongated by insertions of antigen sequences of various bacterial and viral pathogens, for example by the protein sequences of *mycobacterium tuberculosis, brucella abortus* or human immunodeficiency virus (Tabynov K, Sansyzbay A, Kydyrbayev Z, Yespembetov B, Ryskeldinova S, Zinina N, Assanzhanova N, Sultankulova K, Sandybayev N, Khairullin B, Kuznetsova I, Ferko B, Egorov A. Influenza viral vectors expressing the *Brucella* OMP16 or L7/L12 proteins as vaccines against *B. abortus* infection. Virol J. 2014 Apr. 10; 11:69. doi: 10.1186/1743-422X-11-69. PubMed PMID: 24716528; PubMed Central PMCID: PMC3997475; Sereinig S, Stukova M, Zabolotnyh N, Ferko B, Kittel C, Romanova J, Vinogradova T, Katinger H, Kiselev O, Egorov A. Influenza virus NS vectors expressing the *mycobacterium tuberculosis* ESAT-6 protein induce CD4+ Th1 immune response and protect animals against tuberculosis challenge. Clin Vaccine Immunol. 2006 August; 13(8):898-904. PubMed PMID: 16893990; PubMed Central PMCID: PMC1539114; Ferko B, Stasakova J, Sereinig S, Romanova J, Katinger D, Niebler B, Katinger H, Egorov A. Hyperattenuated recombinant influenza A virus nonstructural-protein-encoding vectors induce human immunodeficiency virus type 1 Nef-specific systemic and mucosal immune responses in mice. J Virol. 2001 October; 75(19):8899-908. PubMed PMID: 11533153; PubMed Central PMCID: PMC114458). The constructs carrying NS1 protein truncated to 124 amino acid residues (hereinafter, the NS1-124 vectors) appeared to be optimal by the parameters of reproduction in chicken embryos and of immunogenicity in animals (Ferko B, Stasakova J, Romanova J, Kittel C, Sereinig S, Katinger H, Egorov A. Immunogenicity and protection efficacy of replication-deficient influenza A viruses with altered NS1 genes. J Virol. 2004 December; 78(23):13037-45. PubMed PMID: 15542655; PubMed Central PMCID: PMC524997).

Constructs with a more truncated NS1 protein had a reduced ability to grow in interferon-competent cells (MDCK cells, A549), including a 10-day-old chicken embryos, and were suitable for the production only in interferon-deficient Vero cells. On the other hand, vectors with an NS1 protein consisting of 124-126 amino acid residues varied in attenuation and were not safe enough in animals. For example, the reproduction level of viral vectors carrying ESAT-6 mycobacterial protein at a specified position could reach in mouse lungs the values close to those of pathogenic influenza viruses ($10^4$ and more of virus particles per gram lung tissue). Moreover, NS1-124 vectors, at an infective dose of >5.0 log/mouse, could cause a significant reproduction of the virus in the lung tissue of infected mice and the formation of visible lung pathology (Egorov A, Brandt S, Sereinig S, Romanova J, Ferko B, Katinger D, Grassauer A, Alexandrova G, Katinger H, Muster T. Transfectant influenza A viruses with long deletions in the NS1 protein grow efficiently in Vero cells. J Virol. 1998 August; 72(8):6437-41. PubMed PMID: 9658085; PubMed Central PMCID: PMC109801; Stukova M A, Sereinig S, Zabolotnyh N V, Ferko B, Kittel C, Romanova J, Vinogradova T I, Katinger H, Kiselev O I, Egorov A. Vaccine potential of influenza vectors expressing *Mycobacterium tuberculosis* ESAT-6 protein. Tuberculosis (Edinb). 2006 May-July; 86(3-4):236-46. PubMed PMID: 16677861). Thus, influenza vectors with the NS1 reading frame truncated to 124 amino acid residues cannot be used for vaccination of humans because they do not correspond to the safety parameters developed for live influenza vaccines, where the essential condition is temperature sensitivity of the virus (a reduced reproductive ability at 39° C.) and the lack of active replication of the virus in the lower respiratory tract of animals (Maassab H F, Bryant M L. The development of live attenuated cold-adapted influenza virus vaccine for humans. Rev Med Virol. 1999 October-December; 9(4):237-44. Review. PubMed PMID: 10578119; Gendon IuZ. [Live cold-adapted influenza vaccine: state-of-the-art]. Vopr Virusol. 2011 January-February; 56(1):4-17. Review. Russian. PubMed PMID: 21427948; Aleksandrova G I, Gushchina M I, Klimov A I, Iotov V V. [Genetic basis for construction of the life influenza type A vaccine using temperature-sensitive mutants]. Mol Gen Mikrobiol Virusol. 1990 March; (3):3-8. Review. Russian. PubMed PMID: 2194119; Kendal A P. Cold-adapted live attenuated influenza vaccines developed in Russia: can they contribute to meeting the needs for influenza control in other countries? Eur J Epidemiol. 1997 July; 13(5):591-609. Review. PubMed PMID: 9258574).

Unlike licensed live influenza vaccines (LIVE allantoic INFLUENZA VACCINE ULTRAVAC® (RF) or Flumist® (USA)), known influenza vectors NS1-124 and constructions close to them did not possess the phenotypic temperature-sensitivity marker (ts phenotype) and had levels of reproduction in mouse lungs, close to the level of the wild-type virus with the full-length NS1 protein.

In 50-60$^{th}$ years of the 20$^{th}$ century, attempts were made to use influenza viruses as an oncolytic agent, which were based on the physician's observations of individual cases of cancer remission after recovering from influenza infection (Lindenmann J, Klein P A. Viral oncolysis: increased immunogenicity of host cellantigen associated with influenza virus. J Exp Med. 1967 Jul. 1; 126(1):93-108).

Since the development of genetic engineering techniques for influenza virus in the late 90s, this created a possibility of producing oncolytic influenza vectors with a modified NS1 protein. It was shown that truncation of the NS1 protein could lead to an enhancement in the oncolytic effect when introducing a recombinant virus into a tumor, due to stimulation of the innate immune system to which the NS1 protein is an antagonist (Sturlan S, Stremitzer S, Bauman S, Sachet M, Wolschek M, Ruthsatz T, Egorov A, Bergmann M. Endogenous expression of proteases in colon cancer cells facilitate influenza A viruses mediated oncolysis. Cancer Biol Ther. 2010 Sep. 15; 10(6):592-9; Ogbomo H, Michaelis M, Geiler J, van Rikxoort M, Muster T, Egorov A, Doerr H W, Cinatl J Jr. Tumor cells infected with oncolytic influenza A virus prime natural killer cells for lysis of resistant tumor cells. Med Microbiol Immunol. 2010 May; 199(2):93-101. doi: 10.1007/s00430-009-0139-0. Epub 2009 Dec. 15. PubMed PMID: 20012989; Efferson C L, Tsuda N, Kawano K, Nistal-Villán E, Sellappan S, Yu D, Murray J L, García-Sastre A, Ioannides C G. Prostate tumor cells infected with a recombinant influenza virus expressing a truncated NS1 protein activate cytolytic CD8+ cells to recognize noninfected tumor cells. J Virol. 2006 January; 80(1):383-94).

Moreover, the possibility of genetic engineering manipulations with the length of the influenza virus NS1 protein allowed the development of vectors whose effectiveness enhanced by the presence of the expression of an immunopotentiating agent, for example interleukin-15 (van Rikxoort M, Michaelis M, Wolschek M, Muster T, Egorov A, Seipelt J, Doerr H W, Cinatl J Jr. Oncolytic effects of a novel influenza A virus expressing interleukin-15 from the NS reading frame. PLoS One. 2012; 7(5):e36506).

These works unfortunately used influenza viruses capable of limited reproduction in some cell cultures that do not possess a necessary genetic stability of the transgene for large-scale production in chicken embryos, which are a substrate optimal for the production of influenza vaccine preparations.

Thus, there remains a need for new effective viral vectors, in particular attenuated influenza vectors, that are characterized by the lack of active reproduction of the virus in animal organisms and have temperature-sensitivity phenotype, and that can be used for the prevention and/or treatment of infectious diseases, as well as for the treatment of oncological diseases.

SUMMARY OF THE INVENTION

The present invention relates to an attenuated influenza A virus inducing a cross-protective response against influenza A and B viruses, comprising a chimeric NS fragment including a truncated reading frame of an NS1 protein and a Nep gene heterologous sequence derived from influenza A subtype that differs from the subtype of said attenuated influenza A virus.

In particular, the present invention relates to an attenuated influenza A virus, wherein said truncated reading frame encodes an NS1 protein consisting of 80 to 130 amino acid residues, more preferably, wherein said truncated reading frame encodes an NS1 protein consisting of 124 amino acid residues.

One embodiment of the present invention relates to an attenuated influenza A virus, wherein said truncated reading frame of an NS1 protein is derived from H1N1 influenza virus subtype, and the Nep gene heterologous sequence is derived from H2N2 influenza virus subtype.

According to yet another embodiment of the present invention, an attenuated influenza A virus containing a chimeric NS fragment including a truncated reading frame of an NS1 protein and a Nep gene heterologous sequence, wherein said truncated reading frame of an NS1 protein is derived from H1N1 influenza virus subtype, and the Nep gene heterologous sequence is derived from H2N2 influenza virus subtype and wherein said truncated reading frame encodes an NS1 protein consisting of 124 amino acid residues.

The invention also relates to an attenuated influenza virus vector expressing a protein or a fragment thereof selected from the group consisting of proteins or fragments thereof from bacteria, viruses, and protozoa, wherein the vector is an attenuated influenza A virus according to the invention, in which a truncated reading frame of an NS1 protein gene is elongated by an insertion of a sequence of at least one transgene encoding a protein or a fragment thereof from bacteria, viruses, and protozoa.

One embodiment of the invention relates to an attenuated influenza virus vector expressing a protein or a fragment thereof that is selected from the group consisting of proteins of an influenza A virus, influenza B virus, *mycobacterium tuberculosis*, herpes virus, respiratory syncytial virus, human immunodeficiency virus, hepatitis C virus, malaria parasite, *Trichomonas, Trypanosoma, Leishmania, Chlamydia*, brucellosis causative agent, or a combination thereof.

Another embodiment of the invention relates to an attenuated influenza virus vector expressing a protein or a fragment thereof from pathogenic bacteria, viruses, or protozoa, wherein said protein or a fragment thereof consists of 10 to 400 amino acids.

According to yet another embodiment of the invention, an attenuated influenza virus vector, wherein an insertion encodes an HA protein region from influenza virus, preferably where the HA protein region is an HA2 subunit region selected from the group consisting of 1-185 amino acids (aa) from influenza A virus, 1-186 aa from influenza B virus, 23-185 aa from influenza A virus, or 65-222 aa from influenza A virus.

The next embodiment of the invention is an attenuated influenza virus vector, wherein an insertion encodes a sequence of an influenza A or B virus HA2 subunit region of from 1 to 21 aa and a sequence of an influenza A virus NP protein region of from 243 to 251 aa.

Another embodiment of the present invention relates to an attenuated influenza virus vector, wherein an insertion encodes protein ESAT-6, Ag85A, Ag85B, Mpt64, HspX, Mtb8.4, or 10.4 of *mycobacterium tuberculosis*, or a fragment thereof, in particular, wherein the viral genome sequence further comprises a sequence encoding a self-cleaving 2A peptide between sequences encoding NS1-124 and ESAT6.

The invention also relates to an attenuated influenza virus vector expressing a protein or a fragment thereof, wherein said vector is an attenuated influenza A virus comprising a chimeric NS fragment including a truncated reading frame of an NS1 protein and a Nep gene heterologous sequence, wherein said truncated reading frame of an NS1 protein is derived from H1N1 influenza virus subtype, and the Nep gene heterologous sequence is derived from H2N2 influenza virus subtype and wherein said truncated reading frame encodes an NS1 protein consisting of 124 amino acid residues, wherein the truncated reading frame of an NS1 protein gene is elongated by an insertion of a sequence encoding 1-21 aa of an influenza B HA2 protein and 243-251 aa of an influenza A NP protein.

The invention further relates to an attenuated influenza virus vector having oncolytic activity, wherein said vector is an attenuated influenza A virus according to the invention, wherein the truncated reading frame of an NS1 protein gene is elongated by an insertion of a sequence of at least one transgene encoding a protein or a fragment thereof from a bacterium, virus, or protozoan.

One embodiment of the invention is an attenuated influenza virus vector having oncolytic activity, wherein an insertion encodes a protein or a fragment thereof selected from the group consisting of proteins or fragments thereof from an influenza A virus, influenza B virus, *mycobacterium tuberculosis*, herpes virus, respiratory syncytial virus, human immunodeficiency virus, hepatitis C virus, malaria parasite, *Trichomonas, Trypanosoma, Leishmania, Chlamydia*, or a combination thereof.

The next embodiment of the invention is an attenuated influenza virus having oncolytic activity, wherein said protein or a fragment thereof consists of 10 to 400 amino acids.

A preferred embodiment of the invention is an attenuated influenza virus vector having oncolytic activity, wherein an insertion encodes protein ESAT-6, Ag85A, Ag85B, Mpt64, HspX, Mtb8.4, or 10.4 of *mycobacterium tuberculosis*, or a fragment thereof, in particular, wherein the truncated reading frame of an NS1 protein gene is elongated by an insertion of a sequence encoding *mycobacterium tuberculosis* protein ESAT-6, more preferably wherein the truncated reading frame of an NS1 protein gene is elongated by an insertion of a sequence encoding self-cleaving 2A peptide and a sequence encoding *mycobacterium tuberculosis* protein ESAT-6.

The invention also relates to an attenuated influenza virus vector inducing a cross-protective response against influenza A and B viruses, comprising:

a nucleotide sequence of a PB2 protein gene derived from influenza A/PR/8/34 (H1N1) virus or a nucleotide sequence having at least 95% sequence identity to said nucleotide sequence of the PB2 protein gene;

a nucleotide sequence of a PB1 protein gene derived from influenza A/PR/8/34 (H1N1) virus or a nucleotide sequence having at least 95% sequence identity to said nucleotide sequence of the PB1 protein gene;

a nucleotide sequence of a PA protein gene derived from influenza A/PR/8/34 (H1N1) virus or a nucleotide sequence having at least 95% sequence identity to said nucleotide sequence of the PA protein gene;

a nucleotide sequence of an NP protein gene derived from influenza A/PR/8/34 (H1N1) virus or a nucleotide sequence having at least 95% sequence identity to said nucleotide sequence of the NP protein gene;

a nucleotide sequence of an M protein gene derived from influenza A/PR/8/34 (H1N1) virus or a nucleotide sequence having at least 95% sequence identity to said nucleotide sequence of the M protein gene;

a nucleotide sequence of an HA protein gene derived from influenza A/California/7/09-like (H1N1pdm) virus or a nucleotide sequence having at least 95% sequence identity to said nucleotide sequence of the HA protein gene;

a nucleotide sequence of an NA protein gene derived from influenza A/California/7/09-like (H1N1pdm) virus or a nucleotide sequence having at least 95% sequence identity to said nucleotide sequence of the NA protein gene; and a nucleotide sequence of an NS protein chimeric gene including:

an NS1 protein reading frame derived from influenza A/PR/8/34 (H1N1), wherein said reading frame is truncated and encodes an NS1 protein consisting of 124 amino acid residues, and a Nep gene sequence derived from influenza A/Singapore/1/57-like (H2N2) virus, or a nucleotide sequence having at least 95% sequence identity to said sequence of the NS chimeric gene;

wherein said NS1 protein truncated reading frame is elongated by an insertion of a nucleotide sequence encoding a fusion peptide of an influenza B virus HA2 subunit region and a nucleotide sequence encoding a conservative B-cell epitope of influenza A virus nucleoprotein (NP). In a specific embodiment, the nucleotide sequence of an NS protein chimeric gene is set forth in SEQ ID NO:21.

The present invention also relates to a pharmaceutical composition for the treatment and/or prevention of an infectious disease in a subject, comprising an effective amount of an attenuated influenza A virus according to the invention or an attenuated influenza virus vector according to the invention, and a pharmaceutically acceptable carrier.

The invention also provides a pharmaceutical composition for the prevention of influenza, comprising in an effective amount of an attenuated influenza virus vector according to the invention and a pharmaceutically acceptable carrier.

In particular, the pharmaceutical composition according to the invention comprises from 6.5 to 10.5 log EID50/ml of an attenuated influenza A virus and a buffer solution comprising from 0 to 1.5 wt. % of a monovalent salt, from 0 to 5 wt. % of an imidazole-containing compound, from 0 to 5 wt. % of a carbohydrate component, from 0 to 2 wt. % of a protein component, from 0 to 2 wt. % of an amino acid component, and from 0 to 10 wt. % of hydroxyethylated starch.

A preferred embodiment of the invention is a pharmaceutical composition, wherein a buffer solution comprises from 0.5 to 1.5 wt. % of a monovalent salt, from 0.01 to 5 wt. % of an imidazole-containing compound, from 1 to 5 wt. % of a carbohydrate component, from 0.1 to 2 wt. % of a protein component, from 0.01 to 2 wt. % of an amino acid component, and from 1 to 10 wt. % of hydroxyethylated starch, preferably the monovalent salt is sodium chloride, the carbohydrate component is sucrose, trehalose, or lactose, the protein component is a human recombinant albumin, casitone, lactalbumin hydrolysate, or gelatin, the amino acid component is arginine, glycine, or sodium glutamate, and the imidazole-containing compound is L-carnosine or N,N'-bis[2-(1H-imidazol-5yl)ethyl]propanediamide.

Another embodiment of the invention is a pharmaceutical composition for the treatment and/or prevention of an infectious disease, wherein the infectious disease is caused by a pathogen selected from the group consisting of an influenza A virus, influenza B virus, *mycobacterium tuberculosis*, herpes simplex virus types I and II, respiratory syncytial virus, human immunodeficiency virus, hepatitis C virus, malaria parasite, *Trichomonas, Chlamydia, Trypanosoma, Leishmania*, or a brucellosis causative agent. In a preferred embodiment of the invention, a subject is a mammal or a bird; in particular, the subject is a human subject.

The invention also relates to a vaccine against an infectious disease, comprising an effective amount of an attenuated influenza A virus according to the invention or an attenuated influenza virus vector according to the invention, and a pharmaceutically acceptable carrier.

The invention also provides a vaccine against influenza, comprising in an effective amount of an attenuated influenza virus vector according to the invention and a pharmaceutically acceptable carrier.

In particular, the vaccine according to the invention comprises from 6.5 to 10.5 log EID50/ml of an attenuated influenza virus vector and a buffer solution comprising from 0 to 1.5 wt. % of a monovalent salt, from 0 to 5 wt. % of an imidazole-containing compound, from 0 to 5 wt. % of a carbohydrate component, from 0 to 2 wt. % of a protein component, from 0 to 2 wt. % of an amino acid component, and from 0 to 10 wt. % of hydroxyethylated starch.

Another embodiment of the invention is a vaccine in which a buffer solution comprises from 0.5 to 1.5 wt. % of a monovalent salt, from 0.01 to 5 wt. % of an imidazole-containing compound, from 1 to 5 wt. % of a carbohydrate component, from 0.1 to 2 wt. % of a protein component, from 0.01 to 2 wt. % of an amino acid component, and from 1 to 10 wt. % of hydroxyethylated starch. In a preferred embodiment, the monovalent salt in said buffer solution is sodium chloride, the carbohydrate component is sucrose, trehalose, or lactose, the protein component is a human recombinant albumin, casitone, lactalbumin hydrolysate, or gelatin, the amino acid component is arginine, glycine, or sodium glutamate, and the imidazole-containing compound is L-carnosine or N,N'-bis[2-(1H-imidazol-5yl)ethyl]propanediamide.

One embodiment of the invention is a vaccine against an infectious disease, wherein the infectious disease is caused by a pathogen selected from the group consisting of an influenza A virus, influenza B virus, *mycobacterium tuberculosis*, herpes simplex virus types I and II, respiratory syncytial virus, human immunodeficiency virus, hepatitis C virus, malaria parasite, *Trichomonas, Chlamydia, Trypanosoma, Leishmania*, or a brucellosis causative agent.

The invention also relates to use of an attenuated influenza A virus according to the invention, an attenuated influenza virus vector according to the invention or a pharmaceutical composition according to the invention for the treatment and/or prevention of an infectious disease in a subject, in particular for the treatment and/or prevention of a disease caused by a pathogen selected from the group consisting of an influenza A virus, influenza B virus, *mycobacterium tuberculosis*, herpes simplex virus types I and II, respiratory syncytial virus, human immunodeficiency virus, hepatitis C virus, malaria parasite, *Trichomonas, Chlamydia, Trypanosoma, Leishmania*, or a brucellosis causative agent. In a preferred embodiment of the invention, the subject is a mammal or a bird; in particular, the subject is a human subject.

The present invention also relates to use of an attenuated influenza virus vector or a pharmaceutical composition according to the invention for the prevention of influenza in a subject.

The invention also relates to a method for treating and/or preventing an infectious disease in a subject in need thereof, the method comprising administering to said subject an effective amount of an attenuated influenza A virus according to the invention, an attenuated influenza virus vector according to the invention, or a pharmaceutical composition according to the invention, preferably, to a method of treating a disease caused by a pathogen selected from the group consisting of an influenza A virus, influenza B virus, *mycobacterium tuberculosis*, herpes simplex virus types I and II, respiratory syncytial virus, human immunodeficiency virus, hepatitis C virus, malaria parasite, *Trichomonas, Chlamydia, Trypanosoma, Leishmania*, or a brucellosis causative agent. In a preferred embodiment of the invention, the subject is a mammal or a bird; in particular, the subject is a human subject.

The invention also provides a pharmaceutical composition for the treatment of an oncological disease in a subject, the comprising an attenuated influenza A virus according to the invention or an attenuated vector according to the invention in an effective amount, and a pharmaceutically acceptable carrier.

One embodiment of the invention is a pharmaceutical composition comprising from 8.5 to 10.5 log EID50/ml of an attenuated influenza A virus according to the invention or an attenuated influenza A virus vector according to the invention and a buffer solution comprising from 0 to 1.5 wt. % of a monovalent salt, from 0 to 5 wt. % of an imidazole-containing compound, from 0 to 5 wt. % of a carbohydrate component, 0 to 2 wt. % of a protein component, from 0 to 2 wt. % of an amino acid component, and from 0 to 10 wt. % of hydroxyethylated starch, wherein in a preferred embodiment of the invention, a buffer solution comprises from 0.5 to 1.5 wt. % of a monovalent salt, from 0.01 to 5 wt. % of an imidazole-containing compound, from 1 to 5 wt. % of a carbohydrate component, from 0.1 to 2 wt. % of a protein component, from 0.01 to 2 wt. % of an amino acid component, and from 1 to 10 wt. % of hydroxyethylated starch.

Another embodiment of the invention is a pharmaceutical composition, wherein in the buffer solution, the monovalent salt is sodium chloride, the carbohydrate component is starch, the protein component is a human albumin, the amino acid component is arginine, and the an imidazole-containing compound is L-carnosine or N,N'-bis[2-(1H-imidazol-5yl)ethyl]propanediamide.

The present invention also relates to use of an attenuated virus vector according to the invention, an attenuated influenza virus vector according to the invention or a pharmaceutical composition according to the invention for the treatment of an oncological disease in a subject, in particular, a disease selected from the group consisting of colorectal cancer, cardioesophageal cancer, pancreatic cancer, cholangiocellular cancer, glioma, glioblastoma, and melanoma. In a preferred embodiment of the invention, the subject is a human subject.

The present invention also relates a method for the treatment of an oncological disease in a subject in need thereof, comprising administering an effective amount of an attenuated influenza A virus according to the invention, an attenuated influenza virus vector according to the invention, or a pharmaceutical composition according to the invention, preferably, to a method for treating an oncological disease selected from the group consisting of colorectal cancer, cardioesophageal cancer, pancreatic cancer, cholangiocellular cancer, glioma, glioblastoma, and melanoma.

In one embodiment of the invention, said administration is intratumor administration, administration to a cavity formed after surgical removal of a tumor, or intravenous administration.

The technical result of the present invention is to produce influenza viruses comprising a chimeric NS genomic fragment and corresponding influenza vectors with a high degree of safety in humans and animals, in particular, vectors that are characterized by the lack of active viral reproduction in the animal organism, have temperature-sensitivity phenotype and that may be used for the prevention and/or treatment of infectious diseases. Another technical result of the invention is to produce influenza viruses comprising a chimeric NS genomic fragment, possessing properties of a universal influenza vaccine in mucosal administration in the absence of adjuvants. In addition, the technical result is a high potential of the growth of the produced influenza viruses and influenza vectors in 10-day-old chicken embryos. Another technical result is to produce influenza vectors that have properties of a universal influenza vaccine. The technical result also is to produce influenza viruses and influenza vectors having oncolytic activity. Another technical result is to reduce the cost required for the production of an influenza vaccine, due to non-use of an adjuvant.

BRIEF DESCRIPTION OF DRAWINGS

FIG. 1 shows the principle of designing an attenuated influenza vector. FIG. 1A shows a scheme of the NS genomic fragment of influenza A/PR/8/34 (H1N1) virus. FIG. 1B shows a scheme of a genetically modified chimeric NS genomic fragment in which the NS1 reading frame is truncated and can be elongated by an insertion of a foreign sequence. The sequence encoding the Nep protein is replaced with a heterologous sequence derived from another influenza A virus subtype.

FIG. 2 shows the nucleotide sequences of NS genomic fragments of the wild-type virus and examples of two chimeric genetic constructs. FIG. 2A shows the NS fragment of influenza A/PR/8/34 (H1N1) virus. FIG. 2B shows a chimeric NS fragment of influenza A virus in which the reading frame of the NS1 protein is truncated, and the Nep sequence (marked in bold) is derived from A/Singapore/1/57 (H2N2) virus.

FIG. 2C shows a chimeric NS fragment of influenza A virus, wherein the reading frame of the NS1 protein is truncated, and the Nep sequence (marked in bold type) is derived from A/Leningrad/134/47/57 (H2N2) virus.

FIG. 3 shows the amino acid sequences of proteins translated in the reading frame of NS1 chimeric influenza vectors containing heterologous Nep from virus A/Leningrad/134/47/57 (H2N2) virus.

FIG. 4 shows data demonstrating the pathogenicity and ts-phenotype of viruses with a heterologous Nep gene. FIG. 4A shows data of reproduction of viruses at an optimal temperature of 34° C. and at an elevated temperature of 39° C. temperature in Vero cells. FIG. 4B shows data of reproduction of viruses in mouse lungs on Day 2 after infection.

FIG. 5 shows graphs demonstrating a protective effect of a single immunization of mice with vectors expressing HA2 subunit regions from the NS1 reading frame in the control infection with heterologous pathogenic influenza strains. FIG. 5A shows the lethality in the control infection with A/Mississippi/85/1 (H3N2) virus, and FIG. 5B shows the lethality with the control infection with B/Lee/40 virus.

FIG. 6 presents data on the oncolytic effect of recombinant influenza viruses on melanoma induced in mice by the introduction of $1 \times 10^6$ B16 cells into the foot of a hind paw. The therapy was carried out by intra-tumor administration of the virus on day 5 after the tumor implantation. FIG. 6A shows the average foot size on Day 20 after the tumor implantation and four-time treatment with oncolytic vectors; and FIG. 6B shows the survival of mice after four-time treatment with oncolytic vectors.

FIG. 7 shows the structure of an attenuated influenza vector. There are shown eight fragments of the virus genome and their peculiarities.

It is shown that genome fragments PB2, PB1, PA, Np and M are derived from the A/PR/8/34 (H1N1) virus; the surface HA and NA glycoprotein genes are derived from the A/California/7/09-like (H1N1pdm) virus; the NS genomic fragment has a chimeric structure encoding two proteins: 1) NS1 protein truncated to 124 amino acid residues, elongated by an insertion of a sequence of the N-terminal region of influenza B HA2 protein and by an insertion of a conservative B-cell epitope of influenza A NP protein; and 2) Nep protein having a sequence derived from a heterologous influenza A strain, H2N2 A/Singapore/1/57-like serological subtype.

FIG. 8 shows the nucleotide sequences of genomic fragments of a vaccine vector: PB2, PB1, PA, NP, and M from A/PR/8/34 (H1N1) virus; HA and NA from A/California/7/09-like (H1N1pdm) virus; and a chimeric NS (an insertion in the NS1 reading frame is marked in bold).

FIG. 9 shows results reflecting the protective properties of a vaccine vector after intranasal immunization of mice against various variants of influenza A virus and influenza B virus. The diagrams show mortality (in %) in vaccinated mice after the control infection with the indicated serotypes of influenza A virus or influenza B virus in comparison with the control animals. The vaccine was administered once—1× or twice—2×.

FIG. 10 shows data demonstrating the protective properties of a vaccine vector after intranasal immunization of ferrets. Diagram A shows the dynamics of the mean value of temperature fluctuations after the control infection with A/St.Petersburg/224/2015 (H3N2) virus in vaccinated and control animals. Diagram B shows the inoculation results of the control virus from the ferret nasal washings on Days 2, 4 and 6 after infection. The titers are expressed as the virus mean concentration in nasal washings, expressed as 50% cytopathic dose/ml after titration on MDCK cells. The vaccine was administered once—1× or twice—2×.

DETAILED DESCRIPTION OF THE INVENTION

The present invention relates to attenuated influenza A viruses that are produced by genetically engineered methods and that can be used for the treatment and/or prevention of infectious diseases, as well as for the treatment of oncological diseases.

In particular, the present invention relates to an attenuated influenza A virus inducing a cross-protective response against influenza A and B viruses, comprising a chimeric NS fragment including an NS1 truncated reading frame and a heterologous sequence of the Nep gene derived from influenza A subtype that differs from the subtype of said attenuated influenza A virus. Thus, the influenza A virus subtype for the sequence encoding a truncated NS1 protein differs from the virus subtype from which the Nep protein sequence was derived. In particular, one embodiment of the present invention relates to an attenuated influenza A virus, wherein said NS1 truncated reading frame is derived from influenza H1N1 subtype, and the heterologous sequence of Nep gene is derived from a human or animal influenza subtype of from H2 to H18 subtype.

Said truncated reading frame encodes an NS1 protein comprising from 80 to 130 amino acid residues, more preferably said truncated reading frame encodes an NS1 protein comprising 124 amino acid residues.

The present invention is particularly based on the fact that the inventors have found that the problem of insufficient attenuation (the absence of temperature sensitivity and a high reproduction level in mouse lungs) of influenza vectors, in particular the vector NS1-124, may be solved by modification of the second spliced protein product of an NS genomic fragment of influenza virus—Nep protein (NS2). A replacement of the Nep genomic sequence of influenza A virus, in particular A/PR/8/34 (H1N1) influenza virus, with the Nep sequence derived from heterologous influenza strains, for example from A/Singapore/1/57 (H2N2) or A/Leningrad/134/47/57 (H2N2) virus, leads to the appearance of temperature-sensitivity phenotype and attenuation in influenza A virus, in particular A/PR/8/34 (H1N1) virus. Based on this phenomenon, chimeric NS fragments of influenza virus were constructed that encode a truncated reading frame, NS1-124, of A/PR/8/34 (H1N1) virus in combination with the Nep protein reading frame derived from H2N2 serological subtype. Reassortant influenza viruses based on A/PR/8/34 virus, regardless of the origin of surface antigens H1N1, H5N1 or H1N1pdm, carrying a chimeric NS genomic fragment were unable to provide active reproduction at 39° C. and in the mouse lungs (attenuation phenotype), but still provided reproduction to high titers in 10-day-old chicken embryos.

The present invention also relates to an attenuated influenza virus vector expressing an antigen or a fragment thereof selected from the group consisting of antigens or fragments thereof from bacteria, viruses, and protozoa, wherein the vector is an attenuated influenza A virus according to the present invention, in which a truncated reading frame of an NS1 protein gene is elongated by an insertion of a sequence of at least one transgene encoding the antigen or a fragment thereof from bacteria, viruses, and protozoa. In general, the attenuated virus can be inserted into a transgene encoding a protein or a fragment thereof from any bacteria, virus or protozoa, pathogenic or non-pathogenic for animals and humans, in particular, the protein may be selected from the group consisting of proteins or their fragments from an influenza A virus, influenza B virus, *mycobacterium tuberculosis, Brucella abortus*, herpes virus, respiratory syncytial virus, human immunodeficiency virus, hepatitis C virus, malaria parasite, *Trichomonas, Trypanosoma, Leishmania, Chlamydia*, brucellosis causative agent, or a combination thereof. In particular, the sequence of an insertion can encode an HA protein fragment of influenza virus, *mycobacterium tuberculosis* protein ESAT-6, Ag85A, Ag85B, Mpt64, HspX, Mtb8.4 or 10.4, or fragments thereof. The genomic sequence of an attenuated vector according to the present invention may further comprise a sequence encoding a self-cleaving 2A peptide between sequences encoding NS1-124 and ESAT6.

The antigen or fragment thereof encoded by the sequence of an insertion may have any size that is limited only by the ability of the genomic fragment to "receive" the nucleotide sequence encoding the antigen or fragment thereof. Preferably, the size of the antigen is from 10 to 400 amino acids. For example, the insertion may encode an HA protein fragment representing an HA2 subunit region selected from the group consisting of 1 to 185 amino acids of influenza A virus, 1 to 186 amino acids of influenza B virus, 23 to 185 amino acids of influenza A virus, or 65 to 222 amino acids of influenza A virus. The numbering of amino acids is given in accordance with the positions of the amino acids in HA2 subunit region of influenza virus from which the transgene is originated.

Another specific embodiment of an attenuated influenza virus vector according to the present invention is a vector in which an insertion encodes a sequence of an influenza A or B virus HA2 subunit region of from 1 to 21 amino acids and a sequence of an influenza A virus NP protein region of from 243 to 251 amino acids. These vector variants, despite a short insertion therein, have been surprisingly found to exhibit the best protective effectiveness against influenza B virus and heterologous antigenic subtypes of influenza A virus after a single immunization of mice, i.e. they exhibit the properties of a universal influenza vaccine.

The inventors found that insertions of foreign antigenic sequences into the NS1 reading frame, for example, after amino acid position 124, did not significantly affect the attenuation phenotype of a chimeric virus produced according to the present invention. Thus, various influenza vectors were obtained that possessed required production characteristics and manifested phenotypic and genotypic markers of attenuation in accordance with the requirements for live influenza vaccines. Regardless of the nature of insertions, the viruses showed their harmlessness for laboratory animals and the similarity of the manifested phenotypic marker of attenuation—the presence of is phenotype. The similarity in their genetic markers of attenuation was determined by the presence of a truncated reading frame of NS1 protein and by the presence of a heterologous sequence of Nep gene derived from another influenza A subtype. Depending on an insertion, the resulting vectors exhibited the properties of a universal influenza vaccine, a vaccine against tuberculosis, etc.

In particular, the present invention relates to an influenza A virus vaccine vector obtained by the genetic engineering method, which can be used to prevent influenza caused by all known strains, including influenza A and B viruses. In particular, the present invention relates to an attenuated influenza A virus inducing a cross-protective response against influenza A and B viruses, comprising a chimeric NS fragment including a truncated reading frame of an NS1 protein and a Nep gene heterologous sequence derived from H2N2 influenza A virus subtype. Thus, the influenza A virus subtype of the sequence encoding a truncated NS1 protein differs from the virus subtype from which the sequence encoding Nep protein was derived. In particular, in the vaccine vector, the NS1 truncated reading frame is from influenza H1N1 subtype, and the Nep heterologous sequence is from H2N2 influenza subtype.

In one embodiment, the present invention relates to an attenuated influenza vector inducing a cross-protective response against influenza A and B viruses, comprising:

a nucleotide sequence of a PB2 protein gene derived from influenza A/PR/8/34 (H1N1) virus or a nucleotide sequence having at least 95% or more (for example, 96, 97, 98, or 99%) sequence identity to said nucleotide sequence of the PB2 protein gene;

a nucleotide sequence of a PB1 protein gene derived from influenza A/PR/8/34 (H1N1) virus or a nucleotide sequence having at least 95% or more (for example, 96, 97, 98, or 99%) sequence identity to said nucleotide sequence of the PB1 protein gene;

a nucleotide sequence of a PA protein gene derived from influenza A/PR/8/34 (H1N1) virus or a nucleotide sequence having at least 95% or more (for example, 96, 97, 98, or 99%) sequence identity to said nucleotide sequence of the PA protein gene;

a nucleotide sequence of an NP protein gene derived from influenza A/PR/8/34 (H1N1) virus or a nucleotide sequence having at least 95% or more (for example, 96, 97, 98, or 99%) sequence identity to said nucleotide sequence of the NP protein gene;

a nucleotide sequence of an M protein gene derived from influenza A/PR/8/34 (H1N1) virus or a nucleotide sequence having at least 95% or more (for example, 96, 97, 98, or 99%) sequence identity to said nucleotide sequence of the M protein gene;

a nucleotide sequence of an HA protein gene derived from influenza A/California/7/09-like (H1N1pdm) virus or a nucleotide sequence having at least 95% or more (for example, 96, 97, 98, or 99%) sequence identity to said nucleotide sequence of the HA protein gene;

a nucleotide sequence of an NA protein gene derived from influenza A/California/7/09-like (H1N1pdm) virus or a nucleotide sequence having at least 95% or more (for example, 96, 97, 98, or 99%) sequence identity to said nucleotide sequence of the NA protein gene; and a nucleotide sequence of an NS protein chimeric gene comprising an NS1 protein reading frame derived from influenza A/PR/8/34 (H1N1) virus, wherein said reading frame is truncated and encodes an NS1 protein consisting of 124 amino acid residues, and a Nep gene sequence derived from influenza A/Singapore/1/57-like (H2N2) virus, or a nucleotide sequence having at least 95% or more (for example, 96, 97, 98, or 99%) sequence identity to said nucleotide sequence of the NS chimeric gene;

wherein said NS1 protein truncated reading frame is elongated by an insertion of a nucleotide sequence encoding a fusion peptide of an influenza B virus HA2 subunit region and a nucleotide sequence encoding a conservative B-cell epitope of influenza A virus nucleoprotein (NP).

This truncated reading frame encodes an NS1 protein having 124 amino acid residues that is elongated by two glycines, an insertion of the N-terminal region of the second hemagglutinin subunit HA2 of influenza B virus (23 amino acid residues) and an insertion of a sequence of the conservative B-cell epitope of influenza A virus (7 amino acid residues).

Surface glycoprotein genes of this vector are derived from influenza A/California/7/09 (H1N1pdm) virus. The genes of internal proteins PB2, PB1, RA, NP and M are derived from influenza A/PR/8/34 (H1N1) virus. Thus, the influenza vector according to the invention is a complex genetic construct consisting of genomic sequences of various influenza strains, namely: 1) genes encoding PB2, PB1, PA, NP, and M are from A/PR/8/34 (H1N1) virus (PB2 (Genbank accession number: AB671295), PB1 (Genbank accession number: CY033583), PA (Genbank accession number: AF389117), NP (Genbank accession number: AF389119), M (Genbank accession number: AF389121)), 2) genes encoding HA and NA are from the A/California/7/09-like H1N1pdm virus (HA (GenBank: KM408964.1) and (NA GenBank: KM408965.1)), 3) NS gene is chimeric, wherein the NS protein reading frame of A/PR/8/34 (H1N1) virus is truncated to 124 amino acid residues and is elongated by an insertion of a sequence encoding a fusion peptide of an influenza B virus HA2 subunit region and a sequence encoding a conservative B-cell epitope of influenza A virus nucleoprotein (NP), and the NEP protein reading frame is from H2N2 influenza virus subtype.

The present invention is based, in particular, on the fact that the inventors have unexpectedly found that in intranasal immunization of mice and ferrets with a vector having said structure, without adjuvants, protects the animals against the control infection not only with influenza A (H1N1) viruses but also with influenza A (H3N2) viruses, and influenza B viruses. Therefore, the vaccine vector has the properties of a universal influenza vaccine.

The term "universal vaccine" in the context of the present invention means a vaccine capable of protecting against all known and unknown variants of influenza virus. The usual "seasonal vaccines" protect only against viruses similar to those that are included in the vaccine composition.

The term "mucosal vaccine" means that the vaccine can be administered into the cavities of the respiratory and digestive tracts and applied to the mucous membranes of the mouth and nose, i.e. applied intranasally, orally, or sublingually.

An influenza vector based on A/PR/8/34 virus carrying a chimeric NS genomic fragment were unable to provide active reproduction at 39° C. and in the mouse lungs (attenuation phenotype), but still provided reproduction to high titers in 10-day-old chicken embryos.

The present invention also relates to an attenuated influenza virus vector having oncolytic activity, comprising an attenuated influenza A virus according to the present invention, in which a truncated reading frame of an NS1 protein gene is elongated by an insertion of a sequence of at least one transgene encoding an antigen or a fragment thereof of pathogenic bacteria, viruses, and protozoa. Said antigen can be derived from any bacteria, viruses or protozoa that are pathogenic for animals, in particular the antigen can be selected from the group consisting of antigens of an influenza A virus, influenza B virus, *mycobacterium tuberculosis*, herpes virus, respiratory syncytial virus, human immunodeficiency virus, hepatitis C virus, malaria parasite, *Trichomonas, Trypanosoma, Leishmania, Chlamydia*, or a combination thereof. In particular, the inserted transgene can encode *mycobacterium tuberculosis* protein ESAT-6, Ag85A, Ag85B, Mpt64, HspX, Mtb8.4 or 10.4 or fragments thereof; in addition, the truncated reading frame of an NS1 protein gene can be elongated by an insertion of a sequence encoding *mycobacterium tuberculosis* protein ESAT-6.

The antigen or fragment thereof encoded by the sequence of an insertion may have any size that is limited only by the ability of an NS genomic fragment to "receive" the nucleotide sequence encoding the antigen or fragment thereof. Preferably, the size of the antigen is from 10 to 400 amino acids.

The inventors unexpectedly found that attenuated influenza vectors carrying a chimeric NS genomic fragment possess an enhanced oncolytic activity due to incorporation of a heterologous Nep gene, provided that the pathogenic antigen, in particular a bacterial antigen from the NS1 protein reading frame, is expressed. For example, a viral vector encoding *mycobacterium tuberculosis* protein Esat6 had higher activity than the known recombinant virus having a truncated NS1 protein but without an insertion. Without being bound to any theory, it can be assumed that a strong antituberculous immunity in a mammal contributes to the immune attack of a tumor infected with a virus expressing a tubercular protein.

The present invention also relates to pharmaceutical compositions that contain an effective amount of an attenuated influenza A virus according to the present invention or an attenuated influenza vector according to the present invention and a pharmaceutically acceptable carrier. The pharmaceutical compositions according to the present invention can be used in the treatment and/or prevention of an infectious disease in a subject, in particular an infectious disease caused by a pathogen selected from the group consisting of an influenza A virus, influenza B virus, *mycobacterium tuberculosis*, herpes simplex virus types I and II, respiratory syncytial virus, human immunodeficiency virus, hepatitis C virus, malaria parasite, *Trichomonas, Chlamydia, Trypanosoma*, or *Leishmania*.

In addition, the pharmaceutical compositions according to the present invention can be used in the treatment of oncological diseases of various etiologies; in particular, an oncological disease can be selected from the group consisting of colorectal cancer, cardioesophageal cancer, pancreatic cancer, cholangiocellular cancer, glioma, glioblastoma, and melanoma.

A pharmaceutical composition according to the present invention can be formulated as a vaccine containing an effective amount of an attenuated influenza A virus according to the present invention or an attenuated influenza vector according to the present invention and a pharmaceutically acceptable carrier.

The term "subject" or "animal" as used herein means vertebrates that are prone to infection caused by pathogenic bacteria, viruses or protozoa, including birds (waterfowl, chickens, etc.) and representatives of various mammalian species such as dogs, felines, wolves, ferrets, rodents (rats, mice, etc.), horses, cows, sheep, goats, pigs and primates. In one embodiment of the invention, the subject is a human subject.

The term "effective amount" means the amount of a virus or vector that, when administered to a subject in a single dose or as a part of a treatment cycle, is effective for the treatment and/or prevention with a therapeutic result. This amount can vary depending on the health status and physical condition of a patient, its age, taxonomic group of the subject being treated, a formulation, the estimation of medical situation by a treating physician and other important factors. It is believed that the amount can vary within a relatively wide range, which a skilled person can determine by standard methods. The pharmaceutical composition may contain from 6 to 10.5 log EID50/ml, more particularly from 6.5 to 10.5 log EID50/ml, in particular from 6 to 9.5 log EID50/ml, more particularly from 6.5 to 8.5 log EID50/ml of a chimeric influenza A virus according to the invention or influenza vector according to the invention.

The term "pharmaceutically acceptable carrier", as used herein, means any carrier used in the field, in particular water, physiological saline, a buffer solution and the like. In one embodiment, the pharmaceutically acceptable carrier is a buffer solution containing from 0 to 1.5 wt. % of a monovalent salt, from 0 to 5 wt. % of an imidazole-containing compound, from 0 to 5 wt. % of a carbohydrate component, from 0 to 2 wt. % of a protein component, from 0 to 2 wt. % of an amino acid component and from 0 to 10 wt. % of hydroxyethyl starch, preferably said buffer solution contains from 0.5 to 1.5 wt. % of a monovalent salt, from 0.01 to 5 wt. % of an imidazole compound, from 1 to 5 wt. % of a carbohydrate component, from 0.1 to 2 wt. % of a protein component, from 0.01 to 2 wt. % of an amino acid component and from 1 to 10 wt. % of hydroxyethyl starch, most preferably the monovalent salt is sodium chloride, the carbohydrate component is sucrose, trehalose or lactose, the protein component is human albumin, casitone, lactalbumin hydrolyzate or gelatin, the amino acid component is arginine, glycine or sodium glutamate.

The imidazole-containing compound is L-carnosine or N,N'-bis[2-(1H-imidazol-5-yl)ethyl]-propandiamide having formula:

$$\text{structure}$$

Human albumin can be a recombinant albumin or donor albumin.

The present invention also relates to use of an attenuated influenza A virus, attenuated influenza virus vector or pharmaceutical composition according to the present invention for the treatment and/or prevention of an infectious disease in a subject, in particular an infectious disease caused by a pathogen selected from the group consisting of an influenza A virus, influenza B virus, *mycobacterium tuberculosis*, herpes simplex virus types I and II, respiratory syncytial virus, human immunodeficiency virus, hepatitis C virus, malaria parasite, *Trichomonas, Chlamydia, Trypanosoma*, or *Leishmania*.

The present invention also relates to the use of an attenuated influenza vector or pharmaceutical composition according to the present invention for the prevention of influenza.

Additionally, the present invention also relates to methods of treatment, comprising administering to a subject an attenuated influenza A virus, attenuated influenza vector or pharmaceutical composition according to the present invention. The methods are intended for the treatment and/or prevention of an infectious disease caused by a pathogen viruses, bacteria, or protozoa, in particular infectious diseases caused by a pathogen selected from the group consisting of an influenza A virus, influenza B virus, *mycobacterium tuberculosis*, herpes simplex virus types I and II, respiratory syncytial virus, human immunodeficiency virus, hepatitis C virus, malaria parasite, *Trichomonas, Chlamydia, Trypanosoma*, or *Leishmania*. In addition, the methods are intended for the treatment of oncological diseases in a subject, in particular, an oncological disease can be selected from the group consisting of colorectal cancer, cardioesophageal cancer, pancreatic cancer, cholangiocellular cancer, glioma, glioblastoma, and melanoma.

The administration to a subject can be made by any standard methods, in particular intramuscularly, intravenously, orally, sublingually, inhalationally or intranasally. The influenza vector or pharmaceutical composition can be administered to a subject one, two or more times; a single administration is preferred.

Additionally, in the case of treating cancer, the administration may be intratumor administration, administration to a cavity formed after surgical removal of a tumor, or intravenous administration.

The invention is illustrated below by its embodiments that are not intended to limit the scope of the invention.

EXAMPLES

Example 1

Production of Influenza Vectors with a Modified NS Genomic Fragment

Recombinant viruses were assembled in several steps. At the first step, complementary DNA (cDNA) copies of all eight genomic fragments of influenza virus A/PR/8/34 (H1N1) were synthetically produced by using data from a genetic bank: pHbank-PR8-HA (Genbank accession number: EF467821.1), pHW-PR8-NA (Genbank accession number: AF389120.1), pHW-PR8-PB2 (Genbank accession number: AB671295), pHW-PR8-PB1 (Genbank accession number: CY033583), pHW-PR8-PA (Genbank accession number: AF389117), pHW-PR8-NP (Genbank accession number: AF389119), pHW-PR8-M (Genbank accession number: AF389121), pHW-PR8-NS (Genbank accession number: J02150.1)). At the second step, the synthesized sequences were cloned into a bidirectional plasmid pHW2000-based vector (Hoffmann E, Neumann G, Kawaoka Y, Hobom G, Webster R G, A DNA from eight plasmids, Proc Natl Acad Sci USA. 2000; 97 (11): 6108-13). This plasmid vector, due to the presence of Pol I and Pol II promoters, provided simultaneous intracellular transcription of viral and corresponding messenger RNAs upon transfection of mammalian cells.

There were produced 7 plasmid clones encoding PB1, PB2, PA, HA, NA, NP, and M without modifications, and a set of variants of an NS genomic fragment with modifications, the principle of which is presented in FIG. 1.

FIG. 1A shows schemes of the NS genomic fragment of influenza A/PR/8/34 (H1N1) virus. The full-length genomic fragment of negative-polarity viral RNA (vRNA) has a length of 230 nucleotides (nt). The transcription of the NS fragment by the influenza virus polymerase complex leads to the formation of 2 types of messenger RNA: 1. A direct transcript, which is mRNA of an NS1 protein encoding an NS1 protein having 230 amino acid residues (aa), and spliced mRNA of a Nep protein encoding a protein having 121 aa. FIG. 1B shows a scheme of a genetically modified chimeric NS genomic fragment, where the reading frame of an NS1 protein comprises up to 398 nt and can be elongated by an insertion of a foreign sequence terminated with a triple stop-codon. The sequence encoding a Nep protein is replaced with a heterologous sequence derived from another influenza A virus subtype. As a result of modification, the chimeric NS genomic fragment has a length depending on the length of an insertion of a foreign sequence into the NS1 reading frame.

The nucleotide sequence of influenza A/PR/8/34 (H1N1) virus, including the encoding region and the 5'- and 3'-terminal non-coding regions (sequence number J02150 in the GenBank database), was used as the basis for the development of a chimeric construct of an NS genomic segment. Depending on the purpose, various variants of chimeric constructs of an NS genomic fragment were constructed, with the following common features: 1) replacement of the sequence encoding the Nep protein of A/PR/8/34 (H1N1) virus with a sequence derived from H2N2 influenza virus subtype (strains: A/Singapore/1/57 and A/Leningrad/134/47/57) (FIGS. 2B and 2C); 2) deletion of a sequence consisting of 30 nucleotides (positions 499-428 nt) from the NS1-encoding region, up to the Nep splicing site; 3) limitation of the reading frame of NS1 protein to 124 amino acid residues by inserting a cassette of three consecutive stop codons (TGATAATAA) after nucleotide position 399 (FIG. 2A and FIG. 2B); 4) the presence or absence of a foreign genetic sequence inserted into the NS1 reading frame after nucleotide position 398, just prior to the stop codon cassette.

FIG. 2A shows the sequence of SEQ ID NO:1 of an NS fragment of influenza A/PR/8/34 (H1N1) virus, in which the sequence consisting of 30 nt to be deleted to produce the constructs of B and C is highlighted and underlined. The sequence of Nep gene to be replaced by a heterologous analogue from another influenza A virus subtype is marked in bold. FIG. 2B shows the sequence of SEQ ID NO: 2 of a recombinant NS fragment of influenza A virus in which the reading frame of an NS1 protein is truncated to 398 nt by means of an insertion consisting of three consecutive stop codons (underlined), and the Nep sequence (marked in bold) is borrowed from A/Singapore/1/57 (H2N2) virus. FIG. 2C shows the sequence of SEQ ID NO: 3 of a recombinant NS fragment of influenza A virus in which the reading frame of an NS1 protein is truncated to 398 nt by means of an insertion consisting of three consecutive stop codons (underlined), and the Nep sequence (marked in bold) is borrowed from A/Leningrad/134/47/57 (H2N2) virus.

(SEQ ID NO: 1)
AGCAAAAGCAGGGTGACAAAGACATAATGGATCCAAACACTGTGTCAAG

CTTTCAGGTAGATTGCTTTCTTTGGCATGTCCGCAAACGAGTTGCAGAC

CAAGAACTAGGTGATGCCCCATTCCTTGATCGGCTTCGCCGAGATCAGA

AATCCCTAAGAGGAAGGGGCAGCACTCTTGGTCTGGACATCGAGACAGC

CACACGTGCTGGAAAGCAGATAGTGGAGCGGATTCTGAAAGAAGAATCC

GATGAGGCACTTAAAATGACCATGGCCTCTGTACCTGCGTCGCGTTACC

TAACCGACATGACTCTTGAGGAAATGTCAAGGGAATGGTCCATGCTCAT

ACCCAAGCAGAAAGTGGCAGGCCCTCTTTGTATCAGAATGGACCAGGCG

ATCATG<u>GATAAAAACATCATACTGAAAGCGAACTTC</u>AGTGTGATTTTTG

ACCGGCTGGAGACTCTAATATTGCTAAGGGCTTTCACCGAAGAGGGAGC

AATTGTTGGCGAAATTTCACCATTGCCTTCTCTTCCAGGACATACTGCT

GAGGATGTCAAAAATGCAGTTGGAGTCCTCATCGGAGGACTTGAATGGA

ATGATAACACAGTTCGAGTCTCTGAAACTCTACAGAGATTCGCTTGGAG

AAGCAGTAATGAGAATGGGAGACCTCCACTCACTCCAAAACAGAAACGA

GAAATGGCGGGAACAATTAGGTCAGAAGTTTGAAGAAATAAGATGGTTG

ATTGAAGAAGTGAGACACAAACTGAAGGTAACAGAGAATAGTTTTGAGC

AAATAACATTTATGCAAGCCTTACATCTATTGCTTGAAGTGGAGCAAGA

GATAAGAACTTTCTCATTTCAGCTTATTTAATAATAAAAAACACCCTTG

TTTCTACT (SEQ ID NO: 2)
AGCAAAAGCAGGGTGACAAAGACATAATGGATCCAAACACTGTGTCAAG

CTTTCAGGTAGATTGCTTTCTTTGGCATGTCCGCAAACGAGTTGCAGAC

-continued
```
CAAGAACTAGGTGATGCCCCATTCCTTGATCGGCTTCGCCGAGATCAGA

AATCCCTAAGAGGAAGGGGCAGCACTCTTGGTCTGGACATCGAGACAGC

CACACGTGCTGGAAAGCAGATAGTGGAGCGGATTCTGAAAGAAGAATCC

GATGAGGCACTTAAAATGACCATGGCCTCTGTACCTGCGTCGCGTTACC

TAACCGACATGACTCTTGAGGAAATGTCAAGGGAATGGTCCATGCTCAT

ACCCAAGCAGAAAGTGGCAGGCCCTCTTTGTATCAGAATGGACCAGGCG

ATCATGTGATAATAAAGTGTGATTTTTGACCGGCTGGAGACTCTAATAT

TGCTAAGGGCTTTCACCGAAGAGGGAGCAATTGTTGGCGAAATTTCACC

ATTGCCTTCTCTTCCAGGACATACTAATGAGGATGTCAAAAATGCAATT

GGGGTCCTCATCGGAGGACTTGAATGGAATGATAACACAGTTCGAGTCT

CTAAAACTCTACAGAGATTCGCTTGGTGAAACAGTAATGAGAATGGGAG

ACCTCCACTCACTCCAAAACAGAAACGGAAAATGGCGAGAACAATTAGG

TCAAAAGTTCGAAGAAATAAGATGGCTGATTGAAGAAGTGAGACACAAA

TTGAAGATAACAGAGAATAGTTTTGAGCAAATAACATTTATGCAAGCCT

TACAGCTACTATTTGAAGTGGAACAAGAGATAAGAACTTTCTCGTTTCA

GCTTATTTAATAATAAAAAACACCCTTGTTTCTACT (SEQ ID NO: 3)
AGCAAAAGCAGGGTGACAAAGACATAATGGATCCAAACACTGTGTCAAG

CTTTCAGGTAGATTGCTTTCTTTGGCATGTCCGCAAACGAGTTGCAGAC

CAAGAACTAGGTGATGCCCCATTCCTTGATCGGCTTCGCCGAGATCAGA

AATCCCTAAGAGGAAGGGGCAGCACTCTTGGTCTGGACATCGAGACAGC

CACACGTGCTGGAAAGCAGATAGTGGAGCGGATTCTGAAAGAAGAATCC

GATGAGGCACTTAAAATGACCATGGCCTCTGTACCTGCGTCGCGTTACC

TAACCGACATGACTCTTGAGGAAATGTCAAGGGAATGGTCCATGCTCAT

ACCCAAGCAGAAAGTGGCAGGCCCTCTTTGTATCAGAATGGACCAGGCG

ATCATGTGATAATAAAGTGTGATTTTTGACCGGCTGGAGACTCTAATAT

TGCTAAGGGCTTTCACCGAAGAGGGAGCAATTGTTGGCGAAATTTCACC

ATTGCCTTCTCTTCCAGGACATACTAATGAGGATGTCAAAAATGCAATT

GGGGTCCTCATCGGAGGACTTGAATGGAATGATAACACAGTTCGAGTCT

CTAAAACTCTACAGAGATTCGCTTGGAGAAGCAGTAATGAGAATGGGAG

ACCTCCACTCACTCCAAAACAGAAACGGAAAATGGCGAGAACAATTAGG

TCAAAAGTTCGAAGAAATAAGATGGCTGATTGAAGAAGTGAGACACAAA

TTGAAGATAACAGAGAATAGTTTTGAGCAAATAACATTTATACAAGCCT

TACAGCTACTATTTGAAGTGGAACAAGAGATAAGAACTTTCTCGTTTCA

GCTTATTTAATAATAAAAAACACCCTTGTTTCTACT
```

Thus, the constructed chimeric NS genomic fragments, when transcribed by the polymerase influenza virus complex, formed two types of messenger RNA: 1) NS1 mRNA translated in the form of an NS1 protein truncated to 124 amino acid residues and limited by stop codons or elongated by an insertion of sequences transgenes of different origin, the translation of which is limited by the stop codon cassette; 2) heterologous Nep mRNA derived from influenza A virus of another antigenic subtype. The translation variants of the recombinant NS1 protein with insertions are shown in FIG. 3 and in Table 1 below.

TABLE 1

Amino acid sequences of proteins translated in the NS1 reading frame, recombinant viruses having a heterologous Nep from A/Leningrad/134/47/57 (H2N2) virus

| Designation | Amino acid sequence | Description |
| --- | --- | --- |
| NS124/Nep-Len | MDPNTVSSFQVDCFLWHVRKRVADQELGDAPFLDRL RRDQKSLRGRGSTLGLDIETATRAGKQIVERILKEE SDEALKMTMASVPASRYLTDMTLEEMSREWSMLIPK QKVAGPLCIRMDQAIM (SEQ ID NO: 4) | Virus with the reading frame of an NS1 protein, truncated to 124 aa, without an insertion of a foreign sequence |
| NS124-HA2(A)-185 | MDPNTVSSFQVDCFLWHVRKRVADQELGDAPFLDRL RRDQKSLRGRGSTLGLDIETATRAGKQIVERILKEE SDEALKMTMASVPASRYLTDMTLEEMSREWSMLIPK QKVAGPLCIRMDQAIM-GG-GLFGAIAGFIEGGWTGMIDGWYGYHHQNEQGSGYAA DQKSTQNAINGITNKVNTVIEKMNIQFTAVGKEFNK LEKRMENLNKKVDDGFLDIWTYNAELLVLLENERTL DFHDSNVKNLYEKVKSQLKNNAKEIGNGCFEFYHKC DNECMESVRNGTYDYPKYSEESKLNREKVDGVKLES MGIYQ (SEQ ID NO: 5) | Virus with the reading frame of an NS1 protein, truncated to 124 aa, elongated by the translated sequence of influenza A virus HA2 subunit (shown in bold), from 1 to 185 aa |
| NS124-HA2(A)-65-222 | MDPNTVSSFQVDCFLWHVRKRVADQELGDAPFLDRL RRDQKSLRGRGSTLGLDIETATRAGKQIVERILKEE SDEALKMTMASVPASRYLTDMTLEEMSREWSMLIPK QKVAGPLCIRMDQAIM-*GG*-AVGKEFNKLEKRMENLNKKVDDGFLDIWTYNAELLV LLENERTLDFHDSNVKNLYEKVKSQLKNNAKEIGNG CFEFYHKCDNECMESVRNGTYDYPKYSEESKLNREK VDGVKLESMGIYQILAIYSTVASSLVLLVSLGAISF WMCSNGSLQCRICI (SEQ ID NO: 6) | Virus with the reading frame of an NS1 protein, truncated to 124 aa, elongated by the translated sequence of influenza A virus HA2 subunit (shown in bold), from 65 to 222 aa |

TABLE 1-continued

Amino acid sequences of proteins translated in the NS1 reading
frame, recombinant viruses having a heterologous Nep from
A/Leningrad/134/47/57 (H2N2) virus

| Designation | Amino acid sequence | Description |
|---|---|---|
| NS124-HA2(A)-23-185 | MDPNTVSSFQVDCFLWHVRKRVADQELGDAPFLDRL RRDQKSLRGRGSTLGLDIETATRAGKQIVERILKEE SDEALKMTMASVPASRYLTDMTLEEMSREWSMLIPK QKVAGPLCIRMDQAIM-GG-<br>GYHHQNEQGSGYAADQKSTQNAINGITNKVNTVIEK MNIQFTAVGKEFNKLEKRMENLNKKVDDGFLDIWTY NAELLVLLENERTLDFHDSNVKNLYEKVKSQLKNNA KEIGNGCFEFYHKCDNECMESVRNGTYDYPKYSEES KLNREKVDGVKLESMGIYQ<br>(SEQ ID NO: 7) | Virus with the reading frame of an NS1 protein, truncated to 124 aa, elongated by the translated sequence of influenza A virus HA2 subunit (shown in bold), from 23 to 185 aa |
| NS124-HA2(B)-186 | MDPNTVSSFQVDCFLWHVRKRVADQELGDAPFLDRL RRDQKSLRGRGSTLGLDIETATRAGKQIVERILKEE SDEALKMTMASVPASRYLTDMTLEEMSREWSMLIPK QKVAGPLCIRMDQAIM-GG-<br>GFFGAIAGFLEGGWEGMIAGWHGYTSHGAHGVAVAA DLKSTQEAINKITKNLNSLSELEVKNLQRLSGAMNG LHDEILELDEKVDDLRADTISSQIELAVLLSNEGII NSEDEHLLALERKLKKMLGPSAVEIGNGCFETKHKC NQTCLDRIAAGTFNAGDFSLPTFD<br>(SEQ ID NO: 8) | Virus with the reading frame of an NS1 protein, truncated to 124 aa, elongated by the translated sequence of influenza B virus HA2 subunit (shown in bold), from 1 to 186 aa |
| NS124-Fus(A)-NP | MDPNTVSSFQVDCFLWHVRKRVADQELGDAPFLDRL RRDQKSLRGRGSTLGLDIETATRAGKQIVERILKEE SDEALKMTMASVPASRYLTDMTLEEMSREWSMLIPK QKVAGPLCIRMDQAIM-*GG*-<br>GLFGAIAGFIEGGWTGMIDGW-*GG*-<u>RESRNPGNA</u><br>(SEQ ID NO: 9) | Virus with the reading frame of an NS1 protein, truncated to 124 aa, elongated by the translated sequence of influenza A virus HA2 subunit (shown in bold), from 1 to 186 aa, and with the sequence of a conservative B-cell epitope of influenza A virus NP protein. GG means glycine insertions separating the construct components |
| NS124-Fus(B)-NP | MDPNTVSSFQVDCFLWHVRKRVADQELGDAPFLDRL RRDQKSLRGRGSTLGLDIETATRAGKQIVERILKEE SDEALKMTMASVPASRYLTDMTLEEMSREWSMLIPK QKVAGPLCIRMDQAIM-*GG*-<br>GFFGAIAGFLEGGWEGMIAGW-*GG*-<u>RESRNPGNA</u><br>(SEQ ID NO: 10) | Virus with the reading frame of an NS1 protein, truncated to 124 aa, elongated by the translated sequence of influenza B virus HA2 subunit (shown in bold), from 1 to 21 aa, and with the sequence of a conservative B-cell epitope of influenza A virus NP protein. GG means glycine insertions separating the construct components |
| NS124-Esat6 | MDPNTVSSFQVDCFLWHVRKRVADQELGDAPFLDRL RRDQKSLRGRGSTLGLDIETATRAGKQIVERILKEE SDEALKMTMASVPASRYLTDMTLEEMSREWSMLIPK QKVAGPLCIRMDQAIM-*GG*-<br>MTEQQWNFAGIEAAASAIQGNVTSIHSLLDEGKQSL TKLAAAWGGSGSEAYQGVQQKWDATATELNNALQNL ARTISEAGQAMASTEGNVTGMFA<br>(SEQ ID NO: 11) | Virus with the reading frame of an NS1 protein, truncated to 124 aa, elongated by the translated sequence of mycobacterium tuberculosis protein Esat6 (shown in bold) |

TABLE 1-continued

Amino acid sequences of proteins translated in the NS1 reading frame, recombinant viruses having a heterologous Nep from A/Leningrad/134/47/57 (H2N2) virus

| Designation | Amino acid sequence | Description |
|---|---|---|
| NS24-2A-Esat6 | MDPNTVSSFQVDCFLWHVRKRVADQELGDAPFLDRL RRDQKSLRGRGSTLGLDIETATRAGKQIVERILKEE SDEALKMTMASVPASRYLTDMTLEEMSREWSMLIPK QKVAGPLCIRMDQAIM-*GG*-NFDLLKLAGDVESNPGP-MTEQQWNFAGIEAAASAIQGNVTSIHSLLDEGKQSL TKLAAAWGGSGSEAYQGVQQKWDATATELNNALQNL ARTISEAGQAMASTEGNVTGMFA (SEQ ID NO: 12) | Virus with the reading frame of an NS1 protein, truncated to 124 aa, elongated by the translated sequence of a self-cleaving 2A peptide (from picornavirus) and with the sequence of mycobacterium tuberculosis protein Esat6 |
| NS124-HSV-2ASY | MDPNTVSSFQVDCFLWHVRKRVADQELGDAPFLDRL RRDQKSLRGRGSTLGLDIETATRAGKQIVERILKEE SDEALKMTMASVPASRYLTDMTLEEMSREWSMLIPK QKVAGPLCIRMDQAIM-AAA-NLLTTPKFT-AAA-RMLGDVMAV-AAA-NLLTTPKFT-AAA-RMLGDVMAV (SEQ ID NO: 13) | Virus with the reading frame of an NS1 protein, truncated to 124 aa, elongated by the translated sequences (in bold) of a T-cell epitopes of herpes simplex virus (HSV) 1 and 2 types. Epitope insertions are done with repetition |

Recombinant viruses were assembled by transfection of VERO cells with seven plasmids encoding genomic unmodified fragments of influenza virus, and with one of variants of a chimeric NS genomic fragment by the plasmid DNA electroporation method (Cell Line Nucleofector® Kit V (Lonza)) according to the instruction for use. After transfection, the cells were incubated in Optipro medium (Invitrogen) for 96 hours at 34° C. with the addition of 1 μg/ml trypsin to ensure post-translational cleavage of the hemagglutinin precursor into HA1 and HA2 subunits. The viral harvest from Vero cells was used to infect 10-day-old chicken embryos (SPF). Embryos were incubated for 48 hours at 34° C., after which allantoic fluids having a positive titer in the haemagglutination reaction were used for the second passage on chicken embryos. Allantoic liquids of the second passage were aliquoted and stored at −80° C. The second passage material was used to control the genetic structure of the chimeric NS fragment and the presence of the transgene by producing the RT-PCR product and its sequencing. In addition, the second passage material was used to determine the phenotypic markers of recombinant viral strains and vectors and to determine the genetic stability of the transgene for 5 passages in chicken embryos.

Example 2

Determination of Temperature-Sensitivity Phenotype and Attenuation of Heterologous Nep-Carrying Recombinant Viruses The temperature sensitivity of viruses was determined by comparative titration of the infectious activity of viruses on Vero cells at an optimal temperature of 34° C. and an elevated temperature of 39° C., in 96-well plates. The virus titers were counted by the Reed-Muench method after incubation for 96 hours, taking into account the development of the cytopathic effect in the plate wells (Reed, L J, Muench, H. (1938). "The A simple method of estimating fifty percent endpoints." The American Journal of Hygiene 27: 493-497.). FIG. 4A shows virus titers at these temperatures, expressed in 50% tissue cytopathic doses (Log TCD50/ml). Both viruses carrying heterologous Nep from A/Singapore/1/57 (H2N2) or A/Leningrad/134/47/57 (H2N2) strains surprisingly showed a significant decrease of more than 4 log in infectious titers at 39° C., compared with the optimal temperature of 34° C. Control strains—wild-type A/PR/8/34 (H1N1) virus, and recombinant NS124/Nep PR8 virus with a truncated NS1 protein and a homologous Nep protein did not show temperature sensitivity, replicating effectively at a high temperature. Thus, the replacement of Nep resulted in the appearance of is phenotype in viruses.

Moreover, in intranasal infection of mice under mild anesthesia with said viruses in a dose of 6 log/mouse, viruses—carriers of a heterologous Nep gene had a decreased reproduction ability in the lung tissues (p<0.002), compared with the wild-type virus or NS124/Nep PR8 virus having a homologous Nep (FIG. 4B). Virus titers in the lungs were assessed 2 days after infection of the animals by titration of clarified lung homogenates, in Vero cells. Pulmonary titers were expressed in log TCD50/g lung tissue. Thus, the introduction of the chimeric NS genomic fragment into influenza A/PR/8/34 (H1N1) strain led to the attenuation of the virus, manifested in a decrease in its reproduction ability in the lower respiratory tract of animals.

Example 3

Determination of the ts Phenotype and Attenuation of Vectors Carrying a Chimeric NS Genomic Fragment and Various Insertions in the Reading Frame of an NS1 Protein A wide set of vectors encoding insertions of different nature was produced to determine the effect of insertions of foreign sequences into the reading frame of an NS1 protein on the ts phenotype of viruses comprising a chimeric Nep gene. The viruses with insertions shown in FIG. 3 were studied. The ts-phenotype was studied by titration of the virus infectious activity at temperatures of 34 and 39° C. in 10-day-old chicken embryos (ChE), by determining the haemagglutinating activity of allantoic fluids collected 48 hours after incubation. The titer was calculated by the Reed-Muench method and expressed in log of 50% embryonic infectious doses (log EID50/ml). As can be seen from the data presented in Table 2, all vectors, contrary to the wild-type A/PR/8/34 (H1N1) virus, had a significantly reduced reproduction ability at a high temperature and corresponded in the ts phenotypic marker to the prototype chimeric strains that did not have insertions but carried a heterologous Nep.

TABLE 3

Mouse-lethal dose of the virus

| Virus/vector | 50% lethal virus dose (LD50/ml) | Att-phenotype* |
|---|---|---|
| A/PR/8/34 | 3.2 | No |
| NS124/Nep-Len | >7.5 | Yes |
| NS124/Nep-Sing | >7.5 | Yes |
| NS124-HA2(A)-185 | >7.5 | Yes |
| NS124-HA2(A)-65-222 | >7.5 | Yes |
| NS124-HA2(A)-23-185 | >7.5 | Yes |
| NS124-HA2(B)-186 | >8.0 | Yes |
| NS124-Fus(A)-NP | >8.0 | Yes |
| NS124-Fus(B)-NP | >8.0 | Yes |
| NS124-Esat6 | >7.5 | Yes |
| NS124-2A-Esat6 | >7.5 | Yes |
| NS124-HSV-2ASY | >7.5 | Yes |

*attenuation phenotype is determined by the absence of lethal activity in protective dose exceeding 7.0 log EID50/mouse

TABLE 2

| | NS fragment composition* | | | | |
|---|---|---|---|---|---|
| | NS1 length | Nep origin from | Yield in ChE (Log EID50/ml) at T: | | ts |
| Virus/vector | (aa) | strain** | 34° C. | 39° C. | phenotype*** |
| A/PR/8/34 | 230 | A/PR/8/34 (H1N1) | 9.8 | 9.5 | no |
| NS124/Nep-Len | 124 | Len | 8.8 | 2.8 | yes |
| NS124/Nep-Sing | 124 | Sing | 8.8 | 3.3 | yes |
| NS124-HA2(A)-185 | 124 | Len | 8.3 | 2.8 | yes |
| NS124-HA2(A)-65-222 | 124 | Len | 8.5 | 3.0 | yes |
| NS124-HA2(A)-23-185 | 124 | Len | 8.3 | 3.5 | yes |
| NS124-HA2(B)-186 | 124 | Len | 8.8 | 3.5 | yes |
| NS124-Fus(A)-NP | 124 | Len | 8.0 | 2.8 | yes |
| NS124-Fus(B)-NP | 124 | Len | 8.5 | 2.5 | yes |
| NS124-Esat6 | 124 | Len | 9.5 | 3.8 | yes |
| NS124-2A-Esat6 | 124 | Len | 9.8 | 4.0 | yes |
| NS124-HSV-2ASY | 124 | Len | 8.0 | 2.5 | yes |

Designation:
*Length (in amino acid residues) of the natural NS1 protein sequence before an insertion;
**Origin of the Nep gene from a strain: A/PR/8/34 (H1N1) or A/Singapore/1/57(H2N2), or A/Leningrad/134/47/57 (H2N2);
***ts-phenotype is considered positive if a difference in the virus growth at 34 and 39° C. exceeds 2 log To determine the effect of insertions on the attenuation (att) of vector strains for animals, the mice were challenged intranasally, under mild anesthesia, with virus-containing allantoic fluids of chicken embryos infected with the viruses or vectors represented in FIG. 3. Allantoic fluids were preliminarily characterized by the level infectious virus titers contained therein. The titers were expressed in log EID50/ml. Mice were injected with 0.05 ml of each virus sample. Each group of mice contained 8 animals. The lethal activity of viruses was assessed for 12 days. It was found that, unlike the wild-type A/PR/8/34 (H1N1) virus that caused a 50% lethal effect when using a material with a titer of 3.2 log EID50/ml, none of the vectors showed 50% lethal activity in mice at an infective dose of more than 7.5 log. Thus, all vectors carrying a chimeric NS genomic fragment, regardless of an insertion, were highly attenuated for mice (Table 3).

Example 4

Protective Response to Heterologous Strains of Influenza A and B Viruses in Control Infection of Mice The protective activity to heterologous antigen variants of influenza virus was determined by using viruses with surface antigens from A/PR/8/34 (H1N1) virus carrying a chimeric NS genomic fragment with a Nep sequence from virus A/Leningrad/134/47/57 (H2N2). The following recombinant viruses were used that encoded hemagglutinin HA2 subunit regions in the NS1 reading frame: 1) vector NS124-HA2(A)-185 expressing the full-length influenza A virus HA2 ectodomain of 185 amino acid residues (FIG. 3, SEQ ID NO: 5), 2) vector NS124-HA2(A)-185 expressing the full-length influenza B virus HA2 ectodomain of 186 amino acid residues (FIG. 3, SEQ ID NO: 8) 3) vector NS124-Fus(A)-NP expressing a sequence consisting of the N-terminal 21 amino acid residues of HA2 (fusion domain) in combination with the sequence of a conserved B-cell epitope from influenza A virus NP protein (FIG. 3, SEQ ID NO: 9), and 4) NS124/Nep-Len virus having a stop codon cassette at position 399 of the nucleotide sequence of an NS genomic fragment, limiting translation of the NS1 protein to 124 amino acid residues (FIG. 3, SEQ ID NO: 4). The control groups included mice infected with the wild-type A/PR/8/34 (H1N1) virus without genetic modifications, or mice received a phosphate buffer solution containing no active ingredient. The mice were immunized intranasally under mild anesthesia, with a single viral dose of 6.5 log/mouse. After 28 days, the animals were subjected to a control infection with mouse-pathogenic heterologous influenza strains: A/Mississippi/85/1(H3N2) or B/Lee/40 in a dose corresponding to 3-5 LD50, respectively.

As can be seen in FIG. 5A, the control infection of non-immune mice with the virus (H3N2) resulted in their death in 80% of cases. At the same time, mice immunized with viral preparations were fully protected from death caused by infection with a heterologous influenza A (H3N2) virus strain. Immunization with the wild-type virus also resulted in a statistically significant level of protection against infection by a heterologous strain. When control infection was performed by using influenza B/Lee/40 virus, the immunization of mice with the wild-type A/PR/8/34 (H1N1) virus did not protect animals from death, as well as the mice received in immunization a phosphate buffer solution (FIG. 5B). It was surprisingly found that recombinant viruses carrying insertions in the reading frame of an NS1 protein was protective against influenza B virus. The vector NS124-Fus(A)-NP showed the best protective level. Thus, in single intranasal immunization of mice, the vector strains carrying a chimeric NS genomic fragment, showed the properties of a universal influenza vaccine effective against heterologous antigenic subtypes of both influenza A virus and influenza B virus.

Example 5

Production of an Influenza Vector with a Modified NS Genomic Fragment Encoding a Sequence of Influenza B Virus HA2 Region and H1N1pdm Virus Surface Glycoproteins A recombinant virus was assembled in several steps. At the first step, complementary DNA (cDNA) copies of 5 genomic fragments (PB2, PB1, PA, NP, M) of influenza A/PR/8/34 (H1N1) virus (PB2 (Genbank accession number: AB671295), PB1 (Genbank accession number: CY033583), PA (Genbank accession number: AF389117), NP (Genbank accession number: AF389119), M (Genbank accession number: AF389121)) and 2 genomic fragments (HA, NA) of A/California/7/09-like virus (HA (GenBank: KM408964.1) and (NA GenBank: KM408965.1)) were produced, and a chimeric NS genomic fragment composed of the sequences related to H1N1 virus (NS1 gene), H2N2 virus (Nep gene) and the sequences of two peptides from an influenza B virus HA2 region and an influenza A virus NP region was synthesized.

At the second step, the synthesized sequences were cloned into a bidirectional plasmid pHW2000-based vector (Hoffmann E, Neumann G, Kawaoka Y, Hobom G, Webster R G, A DNA from eight plasmids, Proc Natl Acad Sci USA. 2000; 97 (11):6108-13.). This plasmid vector, due to the presence of Pol I and Pol II promoters, provides simultaneous intracellular transcription of viral and corresponding messenger RNAs upon transfection of mammalian cells. FIG. 7 shows a genetic diagram of the influenza virus. FIG. 8 shows the nucleotide sequences of all eight genomic fragments of the vaccine vector.

```
Nucleotide sequene of genomic PB2
                                                       (SEQ ID NO: 14)
   1 agcgaaagca ggtcaattat attcaatatg gaaagaataa aagaactacg aaatctaatg 61 tcgcagtctc gcacccgcga gatactcaca aaaaccaccg tggaccatat ggccataatc 121 aagaagtaca catcaggaag acaggagaag aacccagcac ttaggatgaa atggatgatg 181 gcaatgaaat atccaattac agcagacaag aggataacgg aaatgattcc tgagagaaat 241 gagcaaggac aaactttatg gagtaaaatg aatgatgccg gatcagaccg agtgatggta 301 tcacctctgg ctgtgacatg gtggaatagg aatggaccaa taacaaatac agttcattat 361 ccaaaaatct acaaaactta ttttgaaaga gtcgaaaggc taaagcatgg aacctttggc 421 cctgtccatt ttagaaacca agtcaaaata cgtcggagag ttgacataaa tcctggtcat 481 gcagatctca gtgccaagga ggcacaggat gtaatcatgg aagttgtttt ccctaacgaa 541 gtgggagcca ggatactaac atcggaatcg caactaacga taaccaaaga gaagaaagaa 601 gaactccagg attgcaaaat ttctccttg atggttgcat acatgttgga gagagaactg 661 gtccgcaaaa cgagattcct cccagtggct ggtggaacaa gcagtgtgta cattgaagtg 721 ttgcatttga ctcaaggaac atgctgggaa cagatgtata ctccaggagg ggaagtgagg 781 aatgatgatg ttgatcaaag cttgattatt gctgctagga acatagtgag aagagctgca 841 gtatcagcag atccactagc atctttattg gagatgtgcc acagcacaca gattggtgga 901 attaggatgg tagacatcct taggcagaac ccaacagaag agcaagccgt ggatatatgc 961 aaggctgcaa tgggactgag aattagctca tccttcagtt ttggtggatt cacatttaag
```

```
1021 agaacaagcg gatcatcagt caagagagag gaagaggtgc ttacgggcaa tcttcaaaca 1081 ttgaagataa gagtgcatga gggatatgaa gagttcacaa tggttgggaa agagcaaca 1141 gccatactca gaaaagcaac caggagattg attcagctga tagtgagtgg gagagacgaa 1201 cagtcgattg ccgaagcaat aattgtggcc atggtatttt cacaagagga ttgtatgata 1261 aaagcagtca gaggtgatct gaatttcgtc aatagggcga atcaacgatt gaatcctatg 1321 catcaacttt taagacattt tcagaaggat gcgaaagtgc ttttcaaaa ttggggagtt 1381 gaacctatcg acaatgtgat gggaatgatt gggatattgc ccgacatgac tccaagcatc 1441 gagatgtcaa tgagaggagt gagaatcagc aaaatgggtg tagatgagta ctccagcacg 1501 gagagggtag tggtgagcat tgaccgtttt ttgagaatcc gggaccaacg aggaaatgta 1561 ctactgtctc ccgaggaggt cagtgaaaca cagggaacag agaaactgac aataacttac 1621 tcatcgtcaa tgatgtggga gattaatggt cctgaatcag tgttggtcaa tacctatcaa 1681 tggatcatca gaaactggga aactgttaaa attcagtggt cccagaaccc tacaatgcta 1741 tacaataaaa tggaatttga accatttcag tctttagtac ctaaggccat tagaggccaa 1801 tacagtgggt ttgtaagaac tctgttccaa caaatgaggg atgtgcttgg acatttgat 1861 accgcacaga taataaaact tcttcccttc gcagccgctc caccaaagca agtagaatg 1921 cagttctcct catttactgt gaatgtgagg ggatcaggaa tgagaatact tgtaaggggc 1981 aattctcctg tattcaacta taacaaggcc acgaagagac tcacagttct cggaaaggat 2041 gctggcactt taactgaaga cccagatgaa ggcacagctg agtggagtc cgctgttctg 2101 aggggattcc tcattctggg caaagaagac aagagatatg gccagcact aagcatcaat 2161 gaactgagca accttgcgaa aggagagaag gctaatgtgc taattgggca aggagacgtg 2221 gtgttggtaa tgaaacggaa acgggactct agcatactta ctgacagcca gacagcgacc 2281 aaaagaattc ggatggccat caattagtgt cgaatagttt aaaaacgacc ttgtttctac 2341 t
```

Nucleotide sequence of genomic PB1
(SEQ ID NO: 15)
```
   1 atggatgtca atccgacctt acttttctta aaagtgccag cacaaaatgc tataagcaca 61 actttccctt atactggaga ccctccttac agccatggga caggaacagg atacaccatg 121 gatactgtca acaggacaca tcagtactca gaaaagggaa gatggacaac aaacaccgaa 181 actggagcac cgcaactcaa cccgattgat gggccactgc agaagacaa tgaaccaagt 241 ggttatgccc aaacagattg tgtattggag gcgatggctt ccttgaggga tcccatcct 301 ggtatttttg aaaactcgtg tattgaaacg atggaggttg ttcagcaaac acgagtagac 361 aagctgacac aaggccgaca gacctatgac tggactctaa atagaaacca acctgctgca 421 acagcattgg ccaacacaat agaagtgttc agatcaaatg gcctcacggc caatgagtct 481 ggaaggctca tagacttcct taaggatgta atggagtcaa tgaacaaaga agaaatgggg 541 atcacaactc attttcagag aaagagacgg gtgagagaca tatgactaa gaaaatgata 601 acacagagaa caatgggtaa aagaagcag agattgaaca aaggagtta tctaattaga 661 gcattgaccc tgaacacaat gaccaaagat gctgagagag gaagctaaa acggagagca 721 attgcaaccc cagggatgca ataaggggg tttgtatact tgttgagac actggcaagg 781 agtatatgtg agaaacttga acaatcaggg ttgccagttg gaggcaatga aagaaagca 841 aagttggcaa atgttgtaag gaagatgatg accaattctc aggacaccga actttctttc 901 accatcactg agataacac caaatggaac gaaaatcaga atcctcggat gttttttggcc 961 atgatcacat atatgaccag aaatcagccc gaatggttca gaaatgttct aagtattgct
```

-continued

```
1021 ccaataatgt tctcaaacaa aatggcgaga ctgggaaaag ggtatatgtt tgagagcaag
1081 agtatgaaac ttagaactca aatacctgca gaaatgctag caagcatcga tttgaaatat
1141 ttcaatgatt caacaagaaa gaagattgaa aaaatccgac cgctcttaat agaggggact
1201 gcatcattga gccctggaat gatgatgggc atgttcaata tgttaagcac tgtattaggc
1261 gtctccatcc tgaatcttgg acaaaagaga tacaccaaga ctacttactg gtgggatggt
1321 cttcaatcct ctgacgattt tgctctgatt gtgaatgcac ccaatcatga agggattcaa
1381 gccggagtcg acaggtttta tcgaacctgt aagctacttg gaatcaatat gagcaagaaa
1441 aagtcttaca taaacagaac aggtacattt gaattcacaa gtttttttcta tcgttatggg
1501 tttgttgcca atttcagcat ggagcttccc agttttgggg tgtctgggat caacgagtca
1561 gcggacatga gtattggagt tactgtcatc aaaaacaata tgataaacaa tgatcttggt
1621 ccagcaacag ctcaaatggc ccttcagttg ttcatcaaag attacaggta cacgtaccga
1681 tgccatagag gtgacacaca aatacaaacc cgaagatcat ttgaaataaa gaaactgtgg
1741 gagcaaaccc gttccaaagc tggactgctg gtctccgacg gaggcccaaa tttatacaac
1801 attagaaatc tccacattcc tgaagtctgc ctaaaatggg aattgatgga tgaggattac
1861 caggggcgtt tatgcaaccc actgaaccca tttgtcagcc ataaagaaat tgaatcaatg
1921 aacaatgcag tgatgatgcc agcacatggt ccagccaaaa acatggagta tgatgctgtt
1981 gcaacaacac actcctggat ccccaaaaga aatcgatcca tcttgaatac aagtcaaaga
2041 ggagtacttg aggatgaaca aatgtaccaa aggtgctgca atttatttga aaaattcttc
2101 cccagcagtt catacagaag accagtcggg atatccagta tggtggaggc tatggtttcc
2161 agagcccgaa ttgatgcacg gattgatttc gaatctggaa ggataaagaa agaagagttc
2221 actgagatca tgaagatctg ttccaccatt gaagagctca gacggcaaaa atagtgaatt
2281 tagcttgt
```

Nucleotide sequence of genomic PA (SEQ ID NO: 16)

```
   1 agcgaaagca ggtactgatc caaaatggaa gattttgtgc gacaatgctt caatccgatg
  61 attgtcgagc ttgcggaaaa aacaatgaaa gagtatgggg aggacctgaa aatcgaaaca
 121 aacaaatttg cagcaatatg cactcacttg gaagtatgct tcatgtattc agattttcac
 181 ttcatcaatg agcaaggcga gtcaataatc gtagaacttg gtgatccaaa tgcacttttg
 241 aagcacagat ttgaaataat cgagggaaga gatcgcacaa tggcctggac agtagtaaac
 301 agtatttgca acactacagg ggctgagaaa ccaaagtttc taccagattt gtatgattac
 361 aaggagaata gattcatcga aattggagta acaaggagag aagttcacat atactatctg
 421 gaaaaggcca ataaaattaa atctgagaaa acacacatcc acattttctc gttcactggg
 481 gaagaaatgg ccacaaaggc agactacact ctcgatgaag aaagcagggc taggatcaaa
 541 accagactat tcaccataag acaagaaatg gccagcagag gcctctggga ttcctttcgt
 601 cagtccgaga gaggagaaga gacaattgaa gaaaggtttg aaatcacagg aacaatgcgc
 661 aagcttgccg accaaagtct cccgccgaac ttctccagcc ttgaaaattt tagagcctat
 721 gtggatggat tcgaaccgaa cggctacatt gagggcaagc tgtctcaaat gtccaaagaa
 781 gtaaatgcta gaattgaacc ttttttgaaa acaacaccac gaccacttag acttccgaat
 841 gggcctccct gttctcagcg gtccaaattc ctgctgatgg atgccttaaa attaagcatt
 901 gaggacccaa gtcatgaagg agagggaata ccgctatatg atgcaatcaa atgcatgaga
 961 acattctttg gatggaagga acccaatgtt gttaaaccac acgaaaaggg aataaatcca
1021 aattatcttc tgtcatggaa gcaagtactg gcagaactgc aggacattga gaatgaggag

-continued

```
1081 aaaattccaa agactaaaaa tatgaagaaa acaagtcagc taaagtgggc acttggtgag 1141 aacatggcac cagaaaaggt agactttgac gactgtaaag atgtaggtga tttgaagcaa 1201 tatgatagtg atgaaccaga attgaggtcg ctagcaagtt ggattcagaa tgagtttaac 1261 aaggcatgcg aactgacaga ttcaagctgg atagagctcg atgagattgg agaagatgtg 1321 gctccaattg aacacattgc aagcatgaga aggaattatt tcacatcaga ggtgtctcac 1381 tgcagagcca cagaatacat aatgaagggg gtgtacatca atactgcctt gcttaatgca 1441 tcttgtgcag caatggatga tttccaatta attccaatga taagcaagtg tagaactaag 1501 gagggaaggc gaaagaccaa cttgtatggt ttcatcataa aaggaagatc ccacttaagg 1561 aatgacaccg acgtggtaaa ctttgtgagc atggagtttt ctctcactga cccaagactt 1621 gaaccacata aatgggagaa gtactgtgtt cttgagatag agatatgct tataagaagt 1681 gccataggcc aggtttcaag gcccatgttc ttgtatgtga aacaaatgg aacctcaaaa 1741 attaaaatga aatggggaat ggagatgagg cgttgcctcc tccagtcact tcaacaaatt 1801 gagagtatga ttgaagctga gtcctctgtc aaagagaaag acatgaccaa agagttcttt 1861 gagaacaaat cagaaacatg gcccattgga gagtccccca aaggagtgga ggaaagttcc 1921 attgggaagg tctgcaggac tttattagca aagtcggtat tcaacagctt gtatgcatct 1981 ccacaactag aaggatttc agctgaatca agaaaactgc ttcttatcgt tcaggctctt 2041 agggacaacc ttgaacctgg gacctttgat cttggggggc tatatgaagc aattgaggag 2101 tgcctgatta atgatccctg ggttttgctt aatgcttctt ggttcaactc cttccttaca 2161 catgcattga gttagttgtg gcagtgctac tatttgctat ccatactgtc caaaaaagta 2221 ccttgtttct act
```

Nucleotide sequence of genomic NP
(SEQ ID NO: 17)

```
  1 agcgaaagca ggtagatatt gaaagatgag tcttctaacc gaggtcgaaa cgtacgtact 61 ctctatcatc ccgtcaggcc ccctcaaagc cgagatcgca cagagacttg aagatgtctt 121 tgcagggaag aacactgatc ttgaggttct catggaatgg ctaaagacaa gaccaatcct 181 gtcacctctg actaagggga ttttaggatt tgtgttcacg ctcaccgtgc ccagtgagcg 241 aggactgcag cgtagacgct ttgtccaaaa tgcccttaat gggaacgggg atccaaataa 301 catggacaaa gcagttaaac tgtataggaa gctcaagagg gagataacat tccatgggc 361 caaagaaatc tcactcagtt attctgctgg tgcacttgcc agttgtatgg cctcatata 421 caacaggatg ggggctgtga ccactgaagt ggcatttggc ctggtatgtg caacctgtga 481 acagattgct gactcccagc atcggtctca taggcaaatg gtgacaacaa ccaatccact 541 aatcagacat gagaacagaa tggttttagc cagcactaca gctaaggcta tggagcaaat 601 ggctggatcg agtgagcaag cagcagaggc catggaggtt gctagtcagg ctagacaaat 661 ggtgcaagcg atgagaacca ttgggactca tcctagctcc agtgctggtc tgaaaaatga 721 tcttcttgaa aatttgcagg cctatcagaa acgaatgggg gtgcagatgc aacggttcaa 781 gtgatcctct cgctattgcc gcaaatatca ttgggatctt gcacttgaca ttgtggattc 841 ttgatcgtct ttttttcaaa tgcatttacc gtcgctttaa atacggactg aaaggagggc 901 cttctacgga aggagtgcca agtctatga gggaagaata tcgaaggaa cagcagagtg 961 ctgtggatgc tgacgatggt catttttgtca gcatagagct ggagtaaaaa actaccttgt 1021 ttctact
```

-continued

Nucleotide sequence of genomic M (SEQ ID NO: 18)

```
   1 agcgaaagca ggtagatatt gaaagatgag tcttctaacc gaggtcgaaa cgtacgtact
  61 ctctatcatc ccgtcaggcc ccctcaaagc cgagatcgca cagagacttg aagatgtctt
 121 tgcagggaag aacactgatc ttgaggttct catggaatgg ctaaagacaa gaccaatcct
 181 gtcacctctg actaagggga ttttaggatt tgtgttcacg ctcaccgtgc ccagtgagcg
 241 aggactgcag cgtagacgct tgtccaaaa tgcccttaat gggaacgggg atccaaataa
 301 catggacaaa gcagttaaac tgtataggaa gctcaagagg gagataacat tccatgggc
 361 caaagaaatc tcactcagtt attctgctgg tgcacttgcc agttgtatgg gcctcatata
 421 caacaggatg ggggctgtga ccactgaagt ggcatttggc ctggtatgtg caacctgtga
 481 acagattgct gactcccagc atcggtctca taggcaaatg gtgacaacaa ccaatccact
 541 aatcagacat gagaacagaa tggttttagc cagcactaca gctaaggcta tggagcaaat
 601 ggctggatcg agtgagcaag cagcagaggc catggaggtt gctagtcagg ctagacaaat
 661 ggtgcaagcg atgagaacca ttgggactca tcctagctcc agtgctggtc tgaaaaatga
 721 tcttcttgaa aatttgcagg cctatcagaa acgaatgggg gtgcagatgc aacggttcaa
 781 gtgatcctct cgctattgcc gcaaatatca ttgggatctt gcacttgaca ttgtggattc
 841 ttgatcgtct ttttttcaaa tgcatttacc gtcgctttaa atacggactg aaaggagggc
 901 cttctacgga aggagtgcca aagtctatga gggaagaata tcgaaaggaa cagcagagtg
 961 ctgtggatgc tgacgatggt cattttgtca gcatagagct ggagtaaaaa actaccttgt
1021 ttctact
```

Nucleotide sequence of genomic HA (SEQ ID NO: 19)

```
   1 atgaaggcaa tactagtagt tctgctatat acatttgcaa ccgcaaatgc agacacatta
  61 tgtataggtt atcatgcaaa caattcaaca gacactgtag acacagtact agaaaagaat
 121 gtaacagtaa cacactctgt taaccttcta agagacaagc ataacgggaa actatgcaaa
 181 ctaagagggg tagccccatt gcatttgggt aaatgtaaca ttgctggctg gatcctggga
 241 aatccagagt gtgaatcact ctccacagca agttcatggt cctacattgt ggaaacatct
 301 agttcagaca atggaacgtg ttacccagga gatttcatca attatgagga gctaagagag
 361 caattgagct cagtgtcatc atttgaaagg tttgagatat tccccaaaac aagttcatgg
 421 cccaatcatg actcgaacaa aggtgtaacg gcagcatgtc ctcacgctgg agcaaaaagc
 481 ttctacaaaa atttaatatg gctagttaaa aaaggaaatt cataccccaa gctcagccaa
 541 tcctacatta tgataaagg gaaagaagtc ctcgtgctgt ggggcattca ccatccatct
 601 actactgctg accaacaaag tctctatcag aatgcagatg catatgtttt tgtggggaca
 661 tcaagataca gcaagaagtt caagccggaa atagcaataa gacccaaagt gagggatcaa
 721 gaagggagaa tgaactatta ctggacacta gtagagccgg agacaaaat aacattcgaa
 781 gcaactggaa atctagtggt accgagatat gcattcacaa tggaaagaaa tgctggatct
 841 ggtattatca tttcagatac accagtccac gattgcaata caacttgtca gacacccgag
 901 ggtgctataa acaccagcct cccatttcag aatatacatc cgatcacaat tggaaaatgt
 961 ccaaagtatg taaaaagcac aaaattgaga ctggccacag gattgaggaa tgtcccgtct
1021 attcaatcta gaggcctatt cggggccatt gccggcttca ttgaagggg gtggacaggg
1081 atggtagatg gatggtacgg ttatcaccat caaaatgagc agggtcagg atatgcagcc
1141 gacctgaaga gcacacaaaa tgccattgac aagattacta acaaagtaaa ctctgttatt
1201 gaaaagatga atacacagtt cacagcagtg gtaaagagt tcaaccacct ggaaaaaaga
```

```
-continued
1261 atagagaatt taaataaaaa agttgatgat ggtttcctgg acatttggac ttacaatgcc 1321 gaactgttgg ttctattgga aaatgaaaga actttggact accatgattc aaatgtgaag 1381 aacttgtatg aaaaggtaag aaaccagtta aaaacaatg ccaaggaaat tggaaacggc 1441 tgctttgaat tttaccacaa atgcgataac acgtgcatgg aaagtgtcaa aatgggact 1501 tatgactacc caaatactc agaggaagca aaattaaaca gagaaaaaat agatggggta 1561 aagctggaat caacaaggat ttaccagatt ttggcgatct attcaactgt cgccagttca 1621 ttggtgctgg tagtctccct gggggcaatc agcttctgga tgtgctctaa tgggtctcta 1681 cagtgtagaa tatgtattta a
```

Nucleotide sequence of genomic NA (SEQ ID NO: 20)

```
  1 atgaatccaa accaaaagat aataaccatt ggttcggtct gtatgacaat tggaatggct 61 aacttaatat tacaaattgg aaacataatc tcaatatgga ttagccactc aattcaagtt 121 gggaatcaaa gtcagatcga acatgcaat caaagcgtca ttacttatga aacaacact 181 tgggtaaatc agacatatgt taacatcagc acaccaact tgctgctgg cagccagtg 241 gtttccgtga aattagcggg caattcctct ctctgccctg ttagtggatg ggctatatac 301 agtaaagaca acagtgtaag agtcggttcc aaggggatg tgtttgtcat aagggaacca 361 ttcatatcat gctcccctt ggaatgcaga accttcttct tgactcaagg ggccttgcta 421 aatgacaaac attccaatgg aaccattaaa gacaggagcc atatcgaac cttaatgagc 481 tgtcctattg gtgaagttcc ctctccatac aactcaagat tgagtcagt cgcttggtca 541 gcaagtgctt gtcatgatgg catcaattgg ctaacaattg gaatttctgg cccagacagt 601 ggggcagtgg ctgtgttaaa gtacaacggc ataataacag acactatcaa gagttggaga 661 aacgatatat tgagaacaca agagtctgaa tgtgcatgtg taaatggttc ttgctttacc 721 ataatgaccg atggaccaag tgatggacag gcctcataca agatcttcag aatagaaaag 781 ggaaagatag tcaaatcagt cgaaatgaat gcccctaatt atcactatga ggaatgctcc 841 tgttatcctg attctagtga aatcacatgt gtgtgcaggg ataactggca tggctcgaat 901 cgaccgtggg tgtctttcaa ccagaatctg gaatatcaga taggatacat atgcagtggg 961 atttcggag acaatccacg ccctaatgat aagacaggca gttgtggtcc agtatcgtct 1021 aatggagcaa atggagtaaa aggattttca ttcaaatacg gcaatggtgt ttggataggg 1081 agaactaaaa gcattagttc aagaaaaggt tttgagatga tttgggatcc aaatggatgg 1141 actgggacag acaataactt ctcaataaag caagatatcg taggaataaa tgagtggtca 1201 ggatatagcg ggagttttgt tcagcatcca gaactaacag gctggattg tataagacct 1261 tgcttctggg ttgaactaat cagagggcga cccaaagaga acacaatctg gactagtggg 1321 agcagcatat ccttttgtgg tgtaaacagt gacactgtgg gttggtcttg gccagacggt 1381 gctgagttgc catttaccat tgacaagtaa
```

Nucleotide sequence of a chimeric NS fragment gene
(insertion is shown in bold type)

(SEQ ID NO: 21)

AGCAAAA

```
-continued
GAGCTATTGCTGGTTTCTTGGAAGGAGGATGGGAAGGAATGATTGCAGGTTGGGGAGGAAGAGAGAGCC

GGAACCCAGGGAATGCTTGATAATAAGCGGCCGCAGTGTGATTTTTGACCGGCTGGAGACTCTAATATT

GCTAAGGGCTTTCACCGAAGAGGGAGCAATTGTTGGCGAAATTTCACCATTGCCTTCTCTTCCAGGACA

TACTAATGAGGATGTCAAAAATGCAATTGGGGTCCTCATCGGAGGACTTGAATGGAATGATAACACAGT

TCGAGTCTCTAAAACTCTACAGAGATTCGCTTGGAGAAGCAGTAATGAGAATGGGAGACCTCCACTCAC

TCCAAAACAGAAACGGAAAATGGCGAGAACAATTAGGTCAAAAGTTCGAAGAAATAAGATGGCTGATTG

AAGAAGTGAGACACAAATTGAAGATAACAGAGAATAGTTTTGAGCAAATAACATTTATACAAGCCTTAC

AGCTACTATTTGAAGTGGAACAAGAGATAAGAACTTTCTCGTTTCAGCTTATTTAATAATAAAAAACAC

CCTTGTTTCTACT
```

Recombinant viruses were assembled by transfection of VERO cells with eight plasmids encoding genomic unmodified fragments of influenza virus, and with a chimeric NS genomic fragment by the plasmid DNA electroporation method (Cell Line Nucleofector® Kit V (Lonza)) according to the instruction for use. After transfection, the cells were incubated in Optipro medium (Invitrogen) for 96 hours at 34° C. with the addition of 1 µg/ml trypsin to ensure post-translational cleavage of the hemagglutinin precursor into HA1 and HA2 subunits. The viral harvest from Vero cells was used to infect 10-day-old chicken embryos (SPF). Embryos were incubated for 48 hours at 34° C., after which allantoic fluids having a positive titer in the haemagglutination reaction were used for next passages on chicken embryos. Allantoic fluids of 7 passages were purified with tangential flow filtration and lyophilized for storage. The animals were immunized after dissolution of the lyophilisate with an equivalent volume of distilled water.

Example 6

Protective Response to Heterologous Strains of Influenza A and B Viruses in Control Infection of Mice The protective activity to heterologous antigen variants of influenza virus was determined by intranasal immunization of mice with an influenza vector at a dose of 6.8 log EID50/mouse in a volume of 50 µl under mild anesthesia, once or twice with a 3 week period. At twenty-one days after the last immunization, the animals were subjected to the control infection with mouse-pathogenic heterologous influenza strains: homologous A/California/7/09 (H1N1pdm) or heterologous A/Aichi/2/68 (H3N2), A/Mississippi/85/1 (H3N2) or influenza B/Lee/40 virus in a dose corresponding to 3-5 LD50, respectively.

As can be seen in FIG. 9A, the control infection of non-immune mice with the H1N1pdm virus resulted in their death in 90% of cases. However, the mice immunized once or twice with the virus preparation were reliably protected from death.

As can be seen in FIG. 3B9B, the control infection of non-immune mice with A/Aichi/2/68 (H3N2) virus resulted in their death in 100% cases. However, the mice immunized once or twice with the virus preparation were reliably protected from death.

As can be seen in FIG. 9C, the control infection of non-immune mice with A/Mississippi/85/1(H3N2) virus resulted in their death in 100% cases. However, the mice immunized twice with the virus preparation had 100% protection.

As can be seen in FIG. 9D, the control infection of non-immune mice with B/Lee/40 influenza virus resulted in their death in 100% cases. However, the mice immunized twice with the virus preparation had 60% protection significantly different from the control.

Thus, the influenza vector carrying a chimeric NS genomic fragment showed the properties of a universal influenza vaccine effective against heterologous antigenic subtypes of both influenza A virus and influenza B virus.

Example 7

Protective Response to a Heterologous Influenza A (H3N2) Strain in the Control Infection of Ferrets Ferrets are an optimal, model recommended by the WHO for studying the effectiveness of influenza vaccines and drugs. The protective activity to a heterologous antigen variant of influenza virus was determined by immunization of ferrets (9 animals per group) with the influenza vector produced in Example 5 at a dose of 7.5 log EID50/ferret, administered intranasal in a volume of 500 µl under mild anesthesia, once or twice with a 3 week period. At twenty-one days after the last immunization, the animals were subjected to the control infection with the ferret-pathogenic A/St.Petersburg/224/2015 (H3N2) virus. As shown in FIG. 10A, the control infection of non-immune animals resulted in a rise of the body temperature on day 2 after infection, while the vaccinated animals did not have a temperature response.

The effect of the vaccination on the reproduction of the control virus in the respiratory tract of ferrets was studied by using nasal washings taken in animals on Days 2, 4 and 6 to determine the concentration of the infectious virus by titration of 50% cytopathic dose in the MDCK cell culture. As can be seen in FIG. 10B, the control infection of non-immune ferrets resulted in the active reproduction of the virus without a significant reduction in titers up to day 6. In a single immunization of ferrets, a significant reduction was observed in the viral titer on Days 4 and 6 after the challenge. After double immunization, a significant, more than 100-fold decrease in the viral titer was recorded already on day 2 after infection of the animals.

Thus, even a single vaccination of ferrets with the influenza vector resulted in the protection of animals from clinical manifestations in the form of a temperature reaction and facilitated the accelerated elimination of the control heterologous strain from the respiratory tract. Repeated immunization accelerated the process of viral elimination.

Example 8

Oncolytic Effect of Influenza Vector Encoding Mycobacterial Protein Esat6

The oncolytic potential of attenuated influenza vectors carrying a chimeric NS genomic fragment with a heterologous Nep gene was determined by treating with the viruses a mouse melanoma induced by the administration of $10^6$ B16 cells in a volume of 30 µl to the subcutaneous space of the right hind foot. Each group contained 10 animals. The therapy was performed on day 5 after the administration of tumor cells, by injection of 30 μl of the viral preparation or a phosphate buffer solution directly into the tumor growth zone. Injections were performed 4 times every third day, after which the rate of an increase in the volume of the affected foot and the survival rate of the animals were assessed for 85 days. The animals with tumors that reached 2000 $mm^3$ were euthanized for ethical reasons and were considered dead.

The melanoma was treated with a vector expressing mycobacterial antigen Esat6 in a design providing for 2A-mediated posttranslational cleavage of protein Esat-6 from the C-terminal region of a truncated NS1 protein of influenza NS124-2A-Esat6 virus (FIG. 3, SEQ ID NO:12). The control therapeutic agent was NS124/Nep-Len virus that did not contain insertions of a mycobacterial protein.

FIG. 6A shows the results of measuring the foot volume on day 19 after administration of the tumor cells. It was surprisingly found that the smallest average feet volume was in mice receiving therapy with a vector expressing protein Esat6. This result was found to correlate with the survival of mice over a long observation period consisting of 85 days (FIG. 6B). Three from ten animals of the NS124-2A-Esat6 group were found to be in remission of the tumor growth, while the animals in the other groups died to day 60. Thus, the obtained data demonstrate the advantage of the oncolytic vector encoding the bacterial antigen.

Example 10

Formulation of an Influenza Virus-Based Vaccine for Intranasal Immunization

A vaccine containing the influenza vector produced in Example 1 or Example 5 in an amount of 6.5 to 8.5 log 50% embryo infectious doses (EID50)/ml, and a buffer stabilizing solution containing 0.9 wt. % chloride solution, 0.5 wt. % L-carnosine, 2.5 wt. % sucrose, 1 wt. % recombinant albumin, 1 wt. % L-arginine and 3 wt. % hydroxyethyl starch 130/0.4 (molecular weight is 130 kDa, the degree of molar substitution is 0.4).

Example 11

Formulation of an Influenza Virus-Based Vaccine for Intranasal Immunization

A vaccine containing the influenza vector produced in Example 1 or Example 5 in an amount of 6.5 to 8.5 log 50% embryo infectious doses (EID50)/ml, and a buffer stabilizing solution containing 0.9 wt. % chloride solution, 0.1 wt. % L-carnosine, 2.5 wt. % sucrose, 1 wt. % recombinant albumin, 1 wt. % L-arginine and 3 wt. % hydroxyethyl starch 130/0.4 (molecular weight is 130 kDa, the degree of molar substitution is 0.4).

Example 12

The Formulation of an Influenza Virus-Based Vaccine for Oncolytic Purposes

A vaccine containing the influenza vector produced in Example 1 or Example 5 in an amount of 6.5 to 10.5 log 50% embryo infectious doses (EID50)/ml, and a buffer stabilizing solution containing 1.35 wt. % chloride solution, 0.5 wt. % L-carnosine, 1 wt. % recombinant albumin, 1 wt. % L-arginine and 3 wt. % hydroxyethyl starch 130/0.4 (molecular weight is 130 kDa, the degree of molar substitution is 0.4).

SEQUENCE LISTING

```
<160> NUMBER OF SEQ ID NOS: 21

<210> SEQ ID NO 1
<211> LENGTH: 890
<212> TYPE: DNA
<213> ORGANISM: Influenza A virus
<220> FEATURE:
<223> OTHER INFORMATION: NS fragment of influenza A/PR/8/34 (H1N1) virus

<400> SEQUENCE: 1
agcaaaagca gggtgacaaa gacataatgg atccaaacac tgtgtcaagc tttcaggtag      60
attgctttct ttggcatgtc cgcaaacgag ttgcagacca agaactaggt gatgccccat     120
tccttgatcg gcttcgccga gatcagaaat ccctaagagg aaggggcagc actcttggtc     180
tggacatcga gacagccaca cgtgctggaa agcagatagt ggagcggatt ctgaaagaag     240
aatccgatga ggcacttaaa atgaccatgg cctctgtacc tgcgtcgcgt tacctaaccg     300
acatgactct tgaggaaatg tcaagggaat ggtccatgct catacccaag cagaaagtgg     360
caggccctct ttgtatcaga atggaccagg cgatcatgga taaaaacatc atactgaaag     420
```

```
cgaacttcag tgtgattttt gaccggctgg agactctaat attgctaagg ctttcaccg      480 aagagggagc aattgttggc gaaatttcac cattgccttc tcttccagga catactgctg     540
aggatgtcaa aaatgcagtt ggagtcctca tcggaggact tgaatggaat gataacacag    600
ttcgagtctc tgaaactcta cagagattcg cttggagaag cagtaatgag aatgggagac    660
ctccactcac tccaaaacag aaacgagaaa tggcgggaac aattaggtca aagtttgaa     720 gaaataagat ggttgattga agaagtgaga cacaaactga aggtaacaga aatagttttt    780
gagcaaataa catttatgca agccttacat ctattgcttg aagtggagca agagataaga   840
actttctcat ttcagcttat ttaataataa aaacacccct tgtttctact              890
```

```
<210> SEQ ID NO 2
<211> LENGTH: 869
<212> TYPE: DNA
<213> ORGANISM: Artificial Sequence
<220> FEATURE:
<223> OTHER INFORMATION: Recombinant NS fragment of influenza A virus
      with a truncated reading frame of an NS1 protein and a Nep
      sequence derived from A/Singapore/1/57 (H2N2) virus

<400> SEQUENCE: 2
```

```
agcaaaagca gggtgacaaa gacataatgg atccaaacac tgtgtcaagc tttcaggtag     60
attgctttct ttggcatgtc cgcaaacgag ttgcagacca gaactaggt gatgccccat     120 tccttgatcg gcttcgccga gatcagaaat ccctaagagg aaggggcagc actcttggtc    180
tggacatcga dacagccaca cgtgctggaa agcagatagt ggagcggatt ctgaaagaag    240
aatccgatga ggcacttaaa atgaccatgg cctctgtacc tgcgtcgcgt tacctaaccg    300
acatgactct tgaggaaatg tcaagggaat ggtccatgct catacccaag cagaaagtgg    360
caggccctct ttgtatcaga atggaccagg cgatcatgtg ataataaagt gtgattttg    420 accggctgga gactctaata ttgctaaggg ctttcaccga gagggagca attgttggcg    480 aaatttcacc attgccttct cttccaggac atactaatga ggatgtcaaa aatgcaattg    540
gggtcctcat cggaggactt gaatggaatg ataacacagt tcgagtctct aaaactctac    600
agagattcgc ttggtgaaac agtaatgaga atggagacc tccactcact ccaaaacaga    660
aacggaaaat ggcgagaaca attaggtcaa aagttcgaag aaataagatg gctgattgaa    720
gaagtgagac acaaattgaa gataacgag aatagtttg agcaaataac atttatgcaa     780
gccttacagc tactatttga agtggaacaa gagataagaa ctttctcgtt tcagcttatt   840
taataataaa aaacacccctt gtttctact                                      869
```

```
<210> SEQ ID NO 3
<211> LENGTH: 869
<212> TYPE: DNA
<213> ORGANISM: Artificial Sequence
<220> FEATURE:
<223> OTHER INFORMATION: Recombinant NS fragment of influenza A virus
      with a truncated reading frame of an NS1 protein and a Nep
      sequence derived from A/Leningrad/134/47/57 (H2N2) virus

<400> SEQUENCE: 3
```

```
agcaaaagca gggtgacaaa gacataatgg atccaaacac tgtgtcaagc tttcaggtag     60
attgctttct ttggcatgtc cgcaaacgag ttgcagacca gaactaggt gatgccccat     120 tccttgatcg gcttcgccga gatcagaaat ccctaagagg aaggggcagc actcttggtc    180
tggacatcga dacagccaca cgtgctggaa agcagatagt ggagcggatt ctgaaagaag    240
aatccgatga ggcacttaaa atgaccatgg cctctgtacc tgcgtcgcgt tacctaaccg    300
```

```
acatgactct tgaggaaatg tcaagggaat ggtccatgct catacccaag cagaaagtgg      360
caggccctct ttgtatcaga atggaccagg cgatcatgtg ataataaagt gtgattttg       420 accggctgga gactctaata ttgctaaggg cttcaccga agagggagca attgttggcg      480
aaatttcacc attgccttct cttccaggac atactaatga ggatgtcaaa aatgcaattg     540
gggtcctcat cggaggactt gaatggaatg ataacacagt tcgagtctct aaaactctac    600
agagattcgc ttggagaagc agtaatgaga atgggagacc tccactcact ccaaaacaga    660
aacggaaaat ggcgagaaca attaggtcaa aagttcgaag aaataagatg gctgattgaa    720
gaagtgagac acaaattgaa gataacagag aatagttttg agcaaataac atttatacaa    780
gccttacagc tactatttga agtggaacaa gagataagaa cttctctgtt tcagcttatt    840
taataataaa aacacccctt gtttctact                                       869
```

```
<210> SEQ ID NO 4
<211> LENGTH: 124
<212> TYPE: PRT
<213> ORGANISM: Artificial Sequence
<220> FEATURE:
<223> OTHER INFORMATION: Truncated NS1 protein without insertion of
      a foreign sequence

<400> SEQUENCE: 4

Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Met Ala Ser Val Pro Ala Ser Arg Tyr Leu Thr Asp Met Thr Leu Glu
                85                  90                  95

Glu Met Ser Arg Glu Trp Ser Met Leu Ile Pro Lys Gln Lys Val Ala
            100                 105                 110

Gly Pro Leu Cys Ile Arg Met Asp Gln Ala Ile Met
        115                 120

<210> SEQ ID NO 5
<211> LENGTH: 311
<212> TYPE: PRT
<213> ORGANISM: Artificial Sequence
<220> FEATURE:
<223> OTHER INFORMATION: Truncated NS1 protein elongated by a sequence
      of an influenza A virus HA2 subunit fragment

<400> SEQUENCE: 5

Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
    50                  55                  60
```

Val Glu Arg Ile Leu Lys Glu Glu Ser Asp Glu Ala Leu Lys Met Thr
65                  70                  75                  80

Met Ala Ser Val Pro Ala Ser Arg Tyr Leu Thr Asp Met Thr Leu Glu
                85                  90                  95

Glu Met Ser Arg Glu Trp Ser Met Leu Ile Pro Lys Gln Lys Val Ala
            100                 105                 110

Gly Pro Leu Cys Ile Arg Met Asp Gln Ala Ile Met Gly Gly Gly Leu
        115                 120                 125

Phe Gly Ala Ile Ala Gly Phe Ile Glu Gly Gly Trp Thr Gly Met Ile
    130                 135                 140

Asp Gly Trp Tyr Gly Tyr His His Gln Asn Glu Gln Gly Ser Gly Tyr
145                 150                 155                 160

Ala Ala Asp Gln Lys Ser Thr Gln Asn Ala Ile Asn Gly Ile Thr Asn
                165                 170                 175

Lys Val Asn Thr Val Ile Glu Lys Met Asn Ile Gln Phe Thr Ala Val
                180                 185                 190

Gly Lys Glu Phe Asn Lys Leu Glu Lys Arg Met Glu Asn Leu Asn Lys
        195                 200                 205

Lys Val Asp Asp Gly Phe Leu Asp Ile Trp Thr Tyr Asn Ala Glu Leu
    210                 215                 220

Leu Val Leu Leu Glu Asn Glu Arg Thr Leu Asp Phe His Asp Ser Asn
225                 230                 235                 240

Val Lys Asn Leu Tyr Glu Lys Val Lys Ser Gln Leu Lys Asn Asn Ala
                245                 250                 255

Lys Glu Ile Gly Asn Gly Cys Phe Glu Phe Tyr His Lys Cys Asp Asn
            260                 265                 270

Glu Cys Met Glu Ser Val Arg Asn Gly Thr Tyr Asp Tyr Pro Lys Tyr
        275                 280                 285

Ser Glu Glu Ser Lys Leu Asn Arg Glu Lys Val Asp Gly Val Lys Leu
    290                 295                 300

Glu Ser Met Gly Ile Tyr Gln
305                 310

<210> SEQ ID NO 6
<211> LENGTH: 284
<212> TYPE: PRT
<213> ORGANISM: Artificial Sequence
<220> FEATURE:
<223> OTHER INFORMATION: Truncated NS1 protein elongated by a sequence
      of an influenza A virus HA2 subunit fragment

<400> SEQUENCE: 6

Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
                20                  25                  30

Leu Asp Arg Leu Arg Arg Asp Gln Lys Ser Leu Arg Gly Arg Gly Ser
            35                  40                  45

Thr Leu Gly Leu Asp Ile Glu Thr Ala Thr Arg Ala Gly Lys Gln Ile
        50                  55                  60

Val Glu Arg Ile Leu Lys Glu Glu Ser Asp Glu Ala Leu Lys Met Thr
65                  70                  75                  80

Met Ala Ser Val Pro Ala Ser Arg Tyr Leu Thr Asp Met Thr Leu Glu
                85                  90                  95

Glu Met Ser Arg Glu Trp Ser Met Leu Ile Pro Lys Gln Lys Val Ala
            100                 105                 110

```
Gly Pro Leu Cys Ile Arg Met Asp Gln Ala Ile Met Gly Gly Ala Val
            115                 120                 125

Gly Lys Glu Phe Asn Lys Leu Glu Lys Arg Met Glu Asn Leu Asn Lys
    130                 135                 140

Lys Val Asp Asp Gly Phe Leu Asp Ile Trp Thr Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asp Asn
        195                 200                 205

Glu Cys Met Glu Ser Val Arg Asn Gly Thr Tyr Asp Tyr Pro Lys Tyr
    210                 215                 220

Ser Glu Glu Ser Lys Leu Asn Arg Glu Lys Val Asp Gly Val Lys Leu
225                 230                 235                 240

Glu Ser Met Gly Ile Tyr Gln Ile Leu Ala Ile Tyr Ser Thr Val Ala
                245                 250                 255

Ser Ser Leu Val Leu Val Ser Leu Gly Ala Ile Ser Phe Trp Met
            260                 265                 270

Cys Ser Asn Gly Ser Leu Gln Cys Arg Ile Cys Ile
        275                 280

<210> SEQ ID NO 7
<211> LENGTH: 289
<212> TYPE: PRT
<213> ORGANISM: Artificial Sequence
<220> FEATURE:
<223> OTHER INFORMATION: Truncated NS1 protein elongated by a sequence
      of an influenza A virus HA2 subunit fragment

<400> SEQUENCE: 7

Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Met Ala Ser Val Pro Ala Ser Arg Tyr Leu Thr Asp Met Thr Leu Glu
                85                  90                  95

Glu Met Ser Arg Glu Trp Ser Met Leu Ile Pro Lys Gln Lys Val Ala
            100                 105                 110

Gly Pro Leu Cys Ile Arg Met Asp Gln Ala Ile Met Gly Gly Tyr
        115                 120                 125

His His Gln Asn Glu Gln Gly Ser Gly Tyr Ala Ala Asp Gln Lys Ser
    130                 135                 140

Thr Gln Asn Ala Ile Asn Gly Ile Thr Asn Lys Val Asn Thr Val Ile
145                 150                 155                 160

Glu Lys Met Asn Ile Gln Phe Thr Ala Val Gly Lys Glu Phe Asn Lys
                165                 170                 175

Leu Glu Lys Arg Met Glu Asn Leu Asn Lys Lys Val Asp Asp Gly Phe
            180                 185                 190
```

```
Leu Asp Ile Trp Thr Tyr Asn Ala Glu Leu Leu Val Leu Glu Asn
            195                 200                 205
Glu Arg Thr Leu Asp Phe His Asp Ser Asn Val Lys Asn Leu Tyr Glu
    210                 215                 220
Lys Val Lys Ser Gln Leu Lys Asn Asn Ala Lys Glu Ile Gly Asn Gly
225                 230                 235                 240
Cys Phe Glu Phe Tyr His Lys Cys Asp Asn Glu Cys Met Glu Ser Val
                245                 250                 255
Arg Asn Gly Thr Tyr Asp Tyr Pro Lys Tyr Ser Glu Glu Ser Lys Leu
            260                 265                 270
Asn Arg Glu Lys Val Asp Gly Val Lys Leu Glu Ser Met Gly Ile Tyr
        275                 280                 285
Gln

<210> SEQ ID NO 8
<211> LENGTH: 294
<212> TYPE: PRT
<213> ORGANISM: Artificial Sequence
<220> FEATURE:
<223> OTHER INFORMATION: Truncated NS1 protein elongated by a sequence
      of an influenza B virus HA2 subunit fragment

<400> SEQUENCE: 8

Met Asp Pro Asn Thr Val Ser Ser Phe Gln Val Asp Cys Phe Leu Trp
1               5                   10                  15
His Val Arg Lys Arg Val Ala Asp Gln Glu Leu Gly Asp Ala Pro Phe
            20                  25                  30
Leu Asp Arg Leu Arg Arg Asp Gln Lys Ser Leu Arg Gly Arg Gly Ser
        35                  40                  45
Thr Leu Gly Leu Asp Ile Glu Thr Ala Thr Arg Ala Gly Lys Gln Ile
    50                  55                  60
Val Glu Arg Ile Leu Lys Glu Glu Ser Asp Glu Ala Leu Lys Met Thr
65                  70                  75                  80
Met Ala Ser Val Pro Ala Ser Arg Tyr Leu Thr Asp Met Thr Leu Glu
                85                  90                  95
Glu Met Ser Arg Glu Trp Ser Met Leu Ile Pro Lys Gln Lys Val Ala
            100                 105                 110
Gly Pro Leu Cys Ile Arg Met Asp Gln Ala Ile Met Gly Gly Gly Phe
        115                 120                 125
Phe Gly Ala Ile Ala Gly Phe Leu Glu Gly Gly Trp Glu Gly Met Ile
    130                 135                 140
Ala Gly Trp His Gly Tyr Thr Ser His Gly Ala His Gly Val Ala Val
145                 150                 155                 160
Ala Ala Asp Leu Lys Ser Thr Gln Glu Ala Ile Asn Lys Ile Thr Lys
                165                 170                 175
Asn Leu Asn Ser Leu Ser Glu Leu Glu Val Lys Asn Leu Gln Arg Leu
            180                 185                 190
Ser Gly Ala Met Asn Gly Leu His Asp Glu Ile Leu Glu Leu Asp Glu
        195                 200                 205
Lys Val Asp Asp Leu Arg Ala Asp Thr Ile Ser Ser Gln Ile Glu Leu
    210                 215                 220
Ala Val Leu Leu Ser Asn Glu Gly Ile Ile Asn Ser Glu Asp Glu His
225                 230                 235                 240
Leu Leu Ala Leu Glu Arg Lys Leu Lys Lys Met Leu Gly Pro Ser Ala
                245                 250                 255
```

Val Glu Ile Gly Asn Gly Cys Phe Glu Thr Lys His Lys Cys Asn Gln
                260                 265                 270

Thr Cys Leu Asp Arg Ile Ala Ala Gly Thr Phe Asn Ala Gly Asp Phe
        275                 280                 285

Ser Leu Pro Thr Phe Asp
    290

<210> SEQ ID NO 9
<211> LENGTH: 158
<212> TYPE: PRT
<213> ORGANISM: Artificial Sequence
<220> FEATURE:
<223> OTHER INFORMATION: Truncated NS1 protein elongated by a sequence
      of an influenza A virus HA2 subunit fragment and a
      sequence of a B-cell epitope of influenza A virus
      NP protein

<400> SEQUENCE: 9

Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Met Ala Ser Val Pro Ala Ser Arg Tyr Leu Thr Asp Met Thr Leu Glu
                85                  90                  95

Glu Met Ser Arg Glu Trp Ser Met Leu Ile Pro Lys Gln Lys Val Ala
            100                 105                 110

Gly Pro Leu Cys Ile Arg Met Asp Gln Ala Ile Met Gly Gly Gly Leu
        115                 120                 125

Phe Gly Ala Ile Ala Gly Phe Ile Glu Gly Gly Trp Thr Gly Met Ile
    130                 135                 140

Asp Gly Trp Gly Gly Arg Glu Ser Arg Asn Pro Gly Asn Ala
145                 150                 155

<210> SEQ ID NO 10
<211> LENGTH: 158
<212> TYPE: PRT
<213> ORGANISM: Artificial Sequence
<220> FEATURE:
<223> OTHER INFORMATION: Truncated NS1 protein elongated by a sequence
      of an influenza A virus HA2 subunit fragment and a
      sequence of a B-cell epitope of influenza A virus
      NP protein

<400> SEQUENCE: 10

Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Met Ala Ser Val Pro Ala Ser Arg Tyr Leu Thr Asp Met Thr Leu Glu
                85                  90                  95

Glu Met Ser Arg Glu Trp Ser Met Leu Ile Pro Lys Gln Lys Val Ala
            100                 105                 110

Gly Pro Leu Cys Ile Arg Met Asp Gln Ala Ile Met Gly Gly Gly Phe
        115                 120                 125

Phe Gly Ala Ile Ala Gly Phe Leu Glu Gly Gly Trp Glu Gly Met Ile
130                 135                 140

Ala Gly Trp Gly Gly Arg Glu Ser Arg Asn Pro Gly Asn Ala
145                 150                 155

<210> SEQ ID NO 11
<211> LENGTH: 221
<212> TYPE: PRT
<213> ORGANISM: Artificial Sequence
<220> FEATURE:
<223> OTHER INFORMATION: Truncated NS1 protein elongated by a sequence
      of mycobacterium tuberculosis protein Esat6 protein

<400> SEQUENCE: 11

Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
50                  55                  60

Val Glu Arg Ile Leu Lys Glu Glu Ser Asp Glu Ala Leu Lys Met Thr
65                  70                  75                  80

Met Ala Ser Val Pro Ala Ser Arg Tyr Leu Thr Asp Met Thr Leu Glu
                85                  90                  95

Glu Met Ser Arg Glu Trp Ser Met Leu Ile Pro Lys Gln Lys Val Ala
            100                 105                 110

Gly Pro Leu Cys Ile Arg Met Asp Gln Ala Ile Met Gly Gly Met Thr
        115                 120                 125

Glu Gln Gln Trp Asn Phe Ala Gly Ile Glu Ala Ala Ala Ser Ala Ile
130                 135                 140

Gln Gly Asn Val Thr Ser Ile His Ser Leu Leu Asp Glu Gly Lys Gln
145                 150                 155                 160

Ser Leu Thr Lys Leu Ala Ala Ala Trp Gly Gly Ser Gly Ser Glu Ala
                165                 170                 175

Tyr Gln Gly Val Gln Gln Lys Trp Asp Ala Thr Ala Thr Glu Leu Asn
            180                 185                 190

Asn Ala Leu Gln Asn Leu Ala Arg Thr Ile Ser Glu Ala Gly Gln Ala
        195                 200                 205

Met Ala Ser Thr Glu Gly Asn Val Thr Gly Met Phe Ala
210                 215                 220

<210> SEQ ID NO 12
<211> LENGTH: 238
<212> TYPE: PRT
<213> ORGANISM: Artificial Sequence
<220> FEATURE:
<223> OTHER INFORMATION: Truncated NS1 protein elongated by a sequence
      of self-cleaving 2A peptide and a sequence of mycobacterium
      tuberculosis protein ESAT-6

```
<400> SEQUENCE: 12

Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Met Ala Ser Val Pro Ala Ser Arg Tyr Leu Thr Asp Met Thr Leu Glu
                85                  90                  95

Glu Met Ser Arg Glu Trp Ser Met Leu Ile Pro Lys Gln Lys Val Ala
            100                 105                 110

Gly Pro Leu Cys Ile Arg Met Asp Gln Ala Ile Met Gly Gly Asn Phe
        115                 120                 125

Asp Leu Leu Lys Leu Ala Gly Asp Val Glu Ser Asn Pro Gly Pro Met
    130                 135                 140

Thr Glu Gln Gln Trp Asn Phe Ala Gly Ile Glu Ala Ala Ala Ser Ala
145                 150                 155                 160

Ile Gln Gly Asn Val Thr Ser Ile His Ser Leu Leu Asp Glu Gly Lys
                165                 170                 175

Gln Ser Leu Thr Lys Leu Ala Ala Ala Trp Gly Gly Ser Gly Ser Glu
            180                 185                 190

Ala Tyr Gln Gly Val Gln Gln Lys Trp Asp Ala Thr Ala Thr Glu Leu
        195                 200                 205

Asn Asn Ala Leu Gln Asn Leu Ala Arg Thr Ile Ser Glu Ala Gly Gln
    210                 215                 220

Ala Met Ala Ser Thr Glu Gly Asn Val Thr Gly Met Phe Ala
225                 230                 235

<210> SEQ ID NO 13
<211> LENGTH: 172
<212> TYPE: PRT
<213> ORGANISM: Artificial Sequence
<220> FEATURE:
<223> OTHER INFORMATION: Truncated NS1 protein elongated by sequences of
      T-cell epitopes of herpes simplex virus (HSV) types I and II

<400> SEQUENCE: 13

Met Asp Pro Asn Thr Val Ser Ser Phe Gln Val

Gly Pro Leu Cys Ile Arg Met Asp Gln Ala Ile Met Ala Ala Ala Asn
            115                 120                 125

Leu Leu Thr Thr Pro Lys Phe Thr Ala Ala Ala Arg Met Leu Gly Asp
    130                 135                 140

Val Met Ala Val Ala Ala Asn Leu Leu Thr Thr Pro Lys Phe Thr
145                 150                 155                 160

Ala Ala Ala Arg Met Leu Gly Asp Val Met Ala Val
                165                 170

<210> SEQ ID NO 14
<211> LENGTH: 2341
<212> TYPE: DNA
<213> ORGANISM: Influenza A virus/PR/8/34 (H1N1)
<220> FEATURE:
<223> OTHER INFORMATION: Nucleotide sequence of PB2 genomic fragment

<400> SEQUENCE: 14

| | | | | | | |
|---|---|---|---|---|---|---|
| agcgaaagca | ggtcaattat | attcaatatg | gaaagaataa | agaactacg | aaatctaatg | 60 |
| tcgcagtctc | gcacccgcga | gatactcaca | aaaccaccg | tggaccatat | ggccataatc | 120 |
| aagaagtaca | catcaggaag | acaggagaag | aacccagcac | ttaggatgaa | atggatgatg | 180 |
| gcaatgaaat | atccaattac | agcagacaag | aggataacgg | aaatgattcc | tgagagaaat | 240 |
| gagcaaggac | aaactttatg | gagtaaaatg | aatgatgccg | gatcagaccg | agtgatggta | 300 |
| tcacctctgg | ctgtgacatg | gtggaatagg | aatggaccaa | taacaaatac | agttcattat | 360 |
| ccaaaaatct | acaaaactta | ttttgaaaga | gtcgaaaggc | taaagcatgg | aaccttggc | 420 |
| cctgtccatt | ttagaaacca | agtcaaaata | cgtcggagag | ttgacataaa | tcctggtcat | 480 |
| gcagatctca | gtgccaagga | ggcacaggat | gtaatcatgg | aagttgtttt | ccctaacgaa | 540 |
| gtgggagcca | ggatactaac | atcggaatcg | caactaacga | taaccaaaga | gaagaaagaa | 600 |
| gaactccagg | attgcaaaat | ttctcctttg | atggttgcat | acatgttgga | gagagaactg | 660 |
| gtccgcaaaa | cgagattcct | cccagtggct | ggtggaacaa | gcagtgtgta | cattgaagtg | 720 |
| ttgcatttga | ctcaaggaac | atgctgggaa | cagatgtata | ctccaggagg | ggaagtgagg | 780 |
| aatgatgatg | ttgatcaaag | cttgattatt | gctgctagga | acatagtgag | aagagctgca | 840 |
| gtatcagcag | atccactagc | atctttattg | gagatgtgcc | acagcacaca | gattggtgga | 900 |
| attaggatgg | tagacatcct | taggcagaac | ccaacagaag | agcaagccgt | ggatatatgc | 960 |
| aaggctgcaa | tgggactgag | aattagctca | tccttcagtt | ttggtggatt | cacatttaag | 1020 |
| agaacaagcg | gatcatcagt | caagagagag | gaagaggtgc | ttacgggcaa | tcttcaaaca | 1080 |
| ttgaagataa | gagtgcatga | gggatatgaa | gagttcacaa | tggttgggag | aagagcaaca | 1140 |
| gccatactca | gaaaagcaac | caggagattg | attcagctga | tagtgagtgg | gagagacgaa | 1200 |
| cagtcgattg | ccgaagcaat | aattgtggcc | atggtatttt | cacaagagga | ttgtatgata | 1260 |
| aaagcagtca | gaggtgatct | gaatttcgtc | aatagggcga | atcaacgatt | gaatcctatg | 1320 |
| catcaacttt | taagacattt | tcagaaggat | gcgaaagtgc | tttttcaaaa | ttggggagtt | 1380 |
| gaacctatcg | acaatgtgat | gggaatgatt | gggatattgc | cgacatgac | tccaagcatc | 1440 |
| gagatgtcaa | tgagaggagt | gagaatcagc | aaaatgggtg | tagatgagta | ctccagcacg | 1500 |
| gagagggtag | tggtgagcat | tgaccgtttt | ttgagaatcc | gggaccaacg | aggaaatgta | 1560 |
| ctactgtctc | ccgaggaggt | cagtgaaaca | cagggaacag | agaaactgac | aataacttac | 1620 |
| tcatcgtcaa | tgatgtggga | gattaatggt | cctgaatcag | tgttggtcaa | tacctatcaa | 1680 |
| tggatcatca | gaaactggga | aactgttaaa | attcagtggt | cccagaaccc | tacaatgcta | 1740 |

| | |
|---|---|
| tacaataaaa tggaatttga accatttcag tctttagtac ctaaggccat tagaggccaa | 1800 |
| tacagtgggt ttgtaagaac tctgttccaa caaatgaggg atgtgcttgg gacatttgat | 1860 |
| accgcacaga taataaaact tcttcccttc gcagccgctc caccaaagca aagtagaatg | 1920 |
| cagttctcct catttactgt gaatgtgagg ggatcaggaa tgagaatact tgtaaggggc | 1980 |
| aattctcctg tattcaacta taacaaggcc acgaagagac tcacagttct cggaaaggat | 2040 |
| gctggcactt taactgaaga cccagatgaa ggcacagctg gagtggagtc cgctgttctg | 2100 |
| aggggattcc tcattctggg caagaagac aagagatatg gccagcact aagcatcaat | 2160 |
| gaactgagca accttgcgaa aggagagaag gctaatgtgc taattgggca aggagacgtg | 2220 |
| gtgttggtaa tgaaacggaa acgggactct agcatactta ctgacagcca gacagcgacc | 2280 |
| aaaagaattc ggatggccat caattagtgt cgaatagttt aaaaacgacc ttgtttctac | 2340 |
| t | 2341 |

<210> SEQ ID NO 15
<211> LENGTH: 2288
<212> TYPE: DNA
<213> ORGANISM: Influenza A virus/PR/8/34 (H1N1)
<220> FEATURE:
<223> OTHER INFORMATION: Nucleotide sequence of PB1 genomic fragment

<400> SEQUENCE: 15

| | |
|---|---|
| atggatgtca atccgacctt acttttctta aaagtgccag cacaaaatgc tataagcaca | 60 |
| actttccctt atactggaga ccctccttac agccatggga caggaacagg atacaccatg | 120 |
| gatactgtca acaggacaca tcagtactca gaaaagggaa gatggacaac aaacaccgaa | 180 |
| actggagcac cgcaactcaa cccgattgat gggccactgc cagaagacaa tgaaccaagt | 240 |
| ggttatgccc aaacagattg tgtattggag gcgatggctt ccttgaggga atcccatcct | 300 |
| ggtattttg aaaactcgtg tattgaaacg atggaggttg ttcagcaaac acgagtagac | 360 |
| aagctgacac aaggccgaca gacctatgac tggactctaa atagaaacca acctgctgca | 420 |
| acagcattgg ccaacacaat agaagtgttc agatcaaatg gcctcacggc caatgagtct | 480 |
| ggaaggctca tagacttcct taaggatgta atggagtcaa tgaacaaaga agaaatgggg | 540 |
| atcacaactc attttcagag aaagagacgg gtgagagaca atatgactaa gaaaatgata | 600 |
| acacagagaa caatgggtaa aaagaagcag agattgaaca aaaggagtta tctaattaga | 660 |
| gcattgaccc tgaacacaat gaccaaagat gctgagagag gaagctaaa acggagagca | 720 |
| attgcaaccc cagggatgca ataagggggg tttgtatact tgttgagac actggcaagg | 780 |
| agtatatgtg agaaacttga caatcagggg ttgccagttg gaggcaatga agaaaagca | 840 |
| aagttggcaa atgttgtaag gaagatgatg accaattctc aggacaccga actttcttc | 900 |
| accatcactg gagataacac caaatggaac gaaaatcaga tcctcggat gttttggcc | 960 |
| atgatcacat atatgaccag aaatcagccc gaatggttca gaatgttct aagtattgct | 1020 |
| ccaataatgt tctcaaacaa aatggcgaga ctgggaaag gtatatgtt tgagagcaag | 1080 |
| agtatgaaac ttagaactca aatacctgca gaaatgctag caagcatcga tttgaaatat | 1140 |
| ttcaatgatt caacaagaaa gaagattgaa aaaatccgac cgctcttaat agaggggact | 1200 |
| gcatcattga gccctggaat gatgatgggc atgttcaata tgttaagcac tgtattaggc | 1260 |
| gtctccatcc tgaatcttgg acaaaagaga tacaccaaga ctacttactg gtgggatggt | 1320 |
| cttcaatcct ctgacgattt tgctctgatt gtgaatgcac ccaatcatga agggattcaa | 1380 |
| gccggagtcg acaggttta tcgaacctgt aagctacttg gaatcaatat gagcaagaaa | 1440 |

```
aagtcttaca taaacagaac aggtacattt gaattcacaa gttttttcta tcgttatggg   1500
tttgttgcca atttcagcat ggagcttccc agttttgggg tgtctgggat caacgagtca   1560
gcggacatga gtattggagt tactgtcatc aaaaacaata tgataaacaa tgatcttggt   1620
ccagcaacag ctcaaatggc ccttcagttg ttcatcaaag attacaggta cacgtaccga   1680
tgccatagag gtgacacaca atacaaacc cgaagatcat ttgaaataaa gaaactgtgg   1740
gagcaaaccc gttccaaagc tggactgctg gtctccgacg gagcccaaa tttatacaac   1800 attagaaatc tccacattcc tgaagtctgc ctaaaatggg aattgatgga tgaggattac   1860
caggggcgtt tatgcaaccc actgaaccca tttgtcagcc ataaagaaat tgaatcaatg   1920
aacaatgcag tgatgatgcc agcacatggt ccagccaaaa acatggagta tgatgctgtt   1980
gcaacaacac actcctggat ccccaaaaga atcgatcca tcttgaatac aagtcaaaga   2040
ggagtacttg aggatgaaca aatgtaccaa aggtgctgca atttatttga aaaattcttc   2100
cccagcagtt catacagaag accagtcggg atatccagta tggtggaggc tatggttttcc   2160 agagcccgaa ttgatgcacg gattgatttc gaatctggaa ggataaagaa agaagagttc   2220
actgagatca tgaagatctg ttccaccatt gaagagctca gacggcaaaa atagtgaatt   2280
tagcttgt                                                            2288

<210> SEQ ID NO 16
<211> LENGTH: 2233
<212> TYPE: DNA
<213> ORGANISM: Influenza A virus/PR/8/34 (H1N1)
<220> FEATURE:
<223> OTHER INFORMATION: Nucleotide sequence of PA genomic fragment

<400> SEQUENCE: 16
agcgaaagca ggtactgatc caaaatggaa gattttgtgc gacaatgctt caatccgatg     60
attgtcgagc ttgcggaaaa aacaatgaaa gagtatgggg aggacctgaa atcgaaaca    120 aacaaatttg cagcaatatg cactcacttg gaagtatgct tcatgtattc agattttcac    180
ttcatcaatg agcaaggcga gtcaataatc gtagaacttg gtgatccaaa tgcacttttg    240
aagcacagat ttgaaataat cgagggaaga gatcgcacaa tggcctggac agtagtaaac    300
agtatttgca acactacagg ggctgagaaa ccaaagtttc taccagattt gtatgattac    360
aaggagaata gattcatcga aattggagta acaaggagag aagttcacat atactatctg    420
gaaaaggcca ataaaattaa atctgagaaa acacacatcc acattttctc gttcactggg    480
gaagaaatgg ccacaaaggc agactacact ctcgatgaag aaagcagggc taggatcaaa    540
accagactat tcaccataag acaagaaatg gccagcagag gcctctggga ttcctttcgt    600
cagtccgaga gaggagaaga gacaattgaa gaaaggtttg aaatcacagg aacaatgcgc    660
aagcttgccg accaaagtct cccgccgaac ttctccagcc ttgaaaattt tagagcctat    720
gtggatggat tcgaaccgaa cggctacatt gagggcaagc tgtctcaaat gtccaaagaa    780
gtaaatgcta gaattgaacc tttttgaaa acaacaccac gaccacttag acttccgaat    840
gggcctccct gttctcagcg gtccaaattc ctgctgatgg atgccttaaa attaagcatt    900
gaggacccaa gtcatgaagg agagggaata ccgctatatg atgcaatcaa atgcatgaga    960
acattctttg gatggaagga acccaatgtt gttaaaccac acgaaagggg aataaatcca   1020
aattatcttc tgtcatggaa gcaagtactg cagaactgc aggacattga gaatgaggag   1080
aaaattccaa agactaaaaa tatgaagaaa acaagtcagc taaagtgggc acttggtgag   1140
aacatggcac cagaaaaggt agactttgac gactgtaaag atgtaggtga tttgaagcaa   1200
```

-continued

```
tatgatagtg atgaaccaga attgaggtcg ctagcaagtt ggattcagaa tgagtttaac    1260
aaggcatgcg aactgacaga ttcaagctgg atagagctcg atgagattgg agaagatgtg    1320
gctccaattg aacacattgc aagcatgaga aggaattatt tcacatcaga ggtgtctcac    1380
tgcagagcca cagaatacat aatgaagggg gtgtacatca atactgcctt gcttaatgca    1440
tcttgtgcag caatggatga tttccaatta attccaatga taagcaagtg tagaactaag    1500
gagggaaggc gaaagaccaa cttgtatggt ttcatcataa aaggaagatc ccacttaagg    1560
aatgacaccg acgtggtaaa ctttgtgagc atggagtttt ctctcactga cccaagactt    1620
gaaccacata aatgggagaa gtactgtgtt cttgagatag agatatgct tataagaagt    1680 gccataggcc aggtttcaag gcccatgttc ttgtatgtga aacaaatgg aacctcaaaa    1740 attaaaatga atggggaat ggagatgagg cgttgcctcc tccagtcact tcaacaaatt    1800
gagagtatga ttgaagctga gtcctctgtc aaagagaaag acatgaccaa agagttcttt    1860
gagaacaaat cagaaacatg gcccattgga gagtccccca aaggagtgga ggaaagttcc    1920
attgggaagg tctgcaggac tttattagca aagtcggtat tcaacagctt gtatgcatct    1980
ccacaactag aaggatttc agctgaatca agaaaactgc ttcttatcgt tcaggctctt    2040
agggacaacc ttgaacctgg gacctttgat cttgggggc tatatgaagc aattgaggag    2100
tgcctgatta atgatccctg ggttttgctt aatgcttctt ggttcaactc cttccttaca    2160
catgcattga gttagttgtg gcagtgctac tatttgctat ccatactgtc caaaaaagta    2220
ccttgtttct act                                                       2233
```

<210> SEQ ID NO 17
<211> LENGTH: 1027
<212> TYPE: DNA
<213> ORGANISM: Influenza A virus/PR/8/34 (H1N1)
<220> FEATURE:
<223> OTHER INFORMATION: Nucleotide sequence of NP genomic fragment

<400> SEQUENCE: 17

```
agcgaaagca ggtagatatt gaaagatgag tcttctaacc gaggtcgaaa cgtacgtact      60
ctctatcatc ccgtcaggcc ccctcaaagc cgagatcgca cagagacttg aagatgtctt     120
tgcagggaag aacactgatc ttgaggttct catggaatgg ctaaagacaa gaccaatcct     180
gtcacctctg actaagggga ttttaggatt tgtgttcacg ctcaccgtgc ccagtgagcg     240
aggactgcag cgtagacgct ttgtccaaaa tgcccttaat gggaacgggg atccaaataa     300
catggacaaa gcagttaaac tgtataggaa gctcaagagg gagataacat tccatggggc     360
caaagaaatc tcactcagtt attctgctgg tgcacttgcc agttgtatgg cctcatata     420 caacaggatg ggggctgtga ccactgaagt ggcatttggc ctggtatgtg caacctgtga     480
acagattgct gactcccagc atcggtctca taggcaaatg gtgacaacaa ccaatccact     540
aatcagacat gagaacagaa tggttttagc cagcactaca gctaaggcta tggagcaaat     600
ggctggatcg agtgagcaag cagcagaggc catggaggtt gctagtcagg ctagacaaat     660
ggtgcaagcg atgagaacca ttgggactca tcctagctcc agtgctggtc tgaaaaatga     720
tcttcttgaa aatttgcagg cctatcagaa acgaatgggg gtgcagatgc aacggttcaa     780
gtgatcctct cgctattgcc gcaaatatca ttgggatctt gcacttgaca ttgtggattc     840
ttgatcgtct ttttttcaaa tgcatttacc gtcgctttaa atacgactg aaaggagggc     900 cttctacgga aggagtgcca aagtctatga gggaagaata tcgaaggaa cagcagagtg     960
```

```
ctgtggatgc tgacgatggt cattttgtca gcatagagct ggagtaaaaa actaccttgt      1020
ttctact                                                                1027

<210> SEQ ID NO 18
<211> LENGTH: 1027
<212> TYPE: DNA
<213> ORGANISM: Influenza A virus/PR/8/34 (H1N1)
<220> FEATURE:
<223> OTHER INFORMATION: Nucleotide sequence of M genomic fragment

<400> SEQUENCE: 18
agcgaaagca ggtagatatt gaaagatgag tcttctaacc gaggtcgaaa cgtacgtact        60
ctctatcatc ccgtcaggcc ccctcaaagc cgagatcgca cagagacttg aagatgtctt       120
tgcagggaag aacactgatc ttgaggttct catggaatgg ctaaagacaa gaccaatcct       180
gtcacctctg actaagggga ttttaggatt tgtgttcacg ctcaccgtgc ccagtgagcg       240
aggactgcag cgtagacgct ttgtccaaaa tgcccttaat gggaacgggg atccaaataa       300
catggacaaa gcagttaaac tgtataggaa gctcaagagg gagataacat tccatggggc       360
caaagaaatc tcactcagtt attctgctgg tgcacttgcc agttgtatgg cctcatata       420 caacaggatg ggggctgtga ccactgaagt ggcatttggc ctggtatgtg caacctgtga       480
acagattgct gactcccagc atcggtctca taggcaaatg gtgacaacaa ccaatccact       540
aatcagacat gagaacagaa tggttttagc cagcactaca gctaaggcta tggagcaaat       600
ggctggatcg agtgagcaag cagcagaggc catggaggtt gctagtcagg ctagacaaat       660
ggtgcaagcg atgagaacca ttgggactca tcctagctcc agtgctggtc tgaaaaatga       720
tcttcttgaa aatttgcagg cctatcagaa acgaatgggg gtgcagatgc aacggttcaa       780
gtgatcctct cgctattgcc gcaaatatca ttgggatctt gcacttgaca ttgtggattc       840
ttgatcgtct ttttttcaaa tgcatttacc gtcgctttaa atacggactg aaaggagggc       900
cttctacgga aggagtgcca agtctatga gggaagaata tcgaaaggaa cagcagagtg       960
ctgtggatgc tgacgatggt cattttgtca gcatagagct ggagtaaaaa actaccttgt      1020
ttctact                                                                1027

<210> SEQ ID NO 19
<211> LENGTH: 1701
<212> TYPE: DNA
<213> ORGANISM: Influenza A virus/California/09-like (H1N1pdm)
<220> FEATURE:
<223> OTHER INFORMATION: Nucleotide sequence of HA genomic fragment

<400> SEQUENCE: 19
atgaaggcaa tactagtagt tctgctatat acatttgcaa ccgcaaatgc agacacatta        60
tgtataggtt atcatgcaaa caattcaaca gacactgtag acacagtact agaaaagaat       120
gtaacagtaa cacactctgt taaccttcta agacaagc ataacgggaa actatgcaaa        180
ctaagagggg tagccccatt gcatttgggt aaatgtaaca ttgctggctg gatcctggga       240
aatccagagt gtgaatcact ctccacagca agttcatggt cctacattgt ggaaacatct       300
agttcagaca atggaacgtg ttacccagga gatttcatca attatgagga gctaagagag       360
caattgagct cagtgtcatc atttgaaagg tttgagatat tcccccaaac aagttcatgg       420
cccaatcatg actcgaacaa aggtgtaacg gcagcatgtc ctcacgctgg agcaaaaagc       480
ttctacaaaa atttaatatg gctagttaaa aaaggaaatt catacccaaa gctcagccaa       540
tcctacatta atgataaagg gaaagaagtc ctcgtgctgt ggggcattca ccatccatct       600
```

```
actactgctg accaacaaag tctctatcag aatgcagatg catatgtttt tgtggggaca    660
tcaagataca gcaagaagtt caagccggaa atagcaataa gacccaaagt gagggatcaa    720
gaagggagaa tgaactatta ctggacacta gtagagccgg gagacaaaat aacattcgaa    780
gcaactggaa atctagtggt accgagatat gcattcacaa tggaaagaaa tgctggatct    840
ggtattatca tttcagatac accagtccac gattgcaata caacttgtca gacacccgag    900
ggtgctataa acaccagcct cccatttcag aatatacatc cgatcacaat ggaaaatgt    960 ccaaagtatg taaaaagcac aaaattgaga ctggccacag gattgaggaa tgtcccgtct   1020
attcaatcta gaggcctatt cggggccatt gccggcttca ttgaaggggg gtggacaggg   1080
atggtagatg gatggtacgg ttatcaccat caaaatgagc aggggtcagg atatgcagcc   1140
gacctgaaga gcacacaaaa tgccattgac aagattacta acaaagtaaa ctctgttatt   1200
gaaaagatga atacacagtt cacagcagtg gtaaagagt tcaaccacct ggaaaaaaga   1260
atagagaatt taaataaaaa agttgatgat ggtttcctgg acatttggac ttacaatgcc   1320
gaactgttgg ttctattgga aaatgaaaga actttggact accatgattc aaatgtgaag   1380
aacttgtatg aaaaggtaag aaaccagtta aaaacaatg ccaaggaaat tggaaacggc   1440
tgctttgaat tttaccacaa atgcgataac acgtgcatga aaagtgtcaa aaatgggact   1500
tatgactacc caaatactc agaggaagca aaattaaaca gagaaaaaat agatggggta   1560
aagctggaat caacaaggat ttaccagatt ttggcgatct attcaactgt cgccagttca   1620
ttggtgctgg tagtctccct gggggcaatc agcttctgga tgtgctctaa tgggtctcta   1680
cagtgtagaa tatgtattta a                                            1701

<210> SEQ ID NO 20
<211> LENGTH: 1410
<212> TYPE: DNA
<213> ORGANISM: Influenza A virus/California/09-like (H1N1pdm)
<220> FEATURE:
<223> OTHER INFORMATION: Nucleotide sequence of NA genomic fragment

<400> SEQUENCE: 20
atgaatccaa accaaaagat aataaccatt ggttcggtct gtatgacaat tggaatggct     60
aacttaatat tacaaattgg aaacataatc tcaatatgga ttagccactc aattcaagtt    120
gggaatcaaa gtcagatcga acatgcaat caaagcgtca ttacttatga aaacaacact    180
tgggtaaatc agacatatgt taacatcagc aacaccaact tgctgctgg cagccagtg    240 gtttccgtga aattagcggg caattcctct ctctgccctg ttagtggatg gctatatac    300 agtaaagaca acagtgtaag agtcggttcc aagggggatg tgtttgtcat aagggaacca    360
ttcatatcat gctccccctt ggaatgcaga accttcttct tgactcaagg ggccttgcta    420
aatgacaaac attccaatgg aaccattaaa gacaggagcc catatcgaac cttaatgagc    480
tgtcctattg gtgaagttcc ctctccatac aactcaagat tgagtcagt cgcttggtca    540 gcaagtgctt gtcatgatgg catcaattgg ctaacaattg gaatttctgg cccagacagt    600
ggggcagtgg ctgtgttaaa gtacaacggc ataataacag acactatcaa gagttggaga    660
aacgatatat tgagaacaca agagtctgaa tgtgcatgtg taaatggttc ttgctttacc    720
ataatgaccg atggaccaag tgatggacag gcctcataca agatcttcag aatagaaaag    780
ggaaagatag tcaaatcagt cgaaatgaat gcccctaatt atcactatga ggaatgctcc    840
tgttatcctg attctagtga aatcacatgt gtgtgcaggg ataactggca tggctcgaat    900
cgaccgtggg tgtctttcaa ccagaatctg gaatatcaga taggatacat atgcagtggg    960
```

```
atttcggag acaatccacg ccctaatgat aagacaggca gttgtggtcc agtatcgtct    1020
aatggagcaa atggagtaaa aggattttca ttcaaatacg gcaatggtgt ttggatagggg   1080 agaactaaaa gcattagttc aagaaaaggt tttgagatga tttgggatcc aaatggatgg    1140
actgggacag acaataactt ctcaataaag caagatatcg taggaataaa tgagtggtca    1200
ggatatagcg ggagttttgt tcagcatcca gaactaacag ggctggattg tataagacct    1260
tgcttctggg ttgaactaat cagagggcga cccaaagaga acacaatctg gactagtggg    1320
agcagcatat cctttgtgg tgtaaacagt gacactgtgg gttggtcttg gccagacggt     1380
gctgagttgc catttaccat tgacaagtaa                                    1410

<210> SEQ ID NO 21
<211> LENGTH: 979
<212> TYPE: DNA
<213> ORGANISM: Artificial Sequence
<220> FEATURE:
<223> OTHER INFORMATION: Nucleotide sequence of a chimeric NS fragment
      gene

<400> SEQUENCE: 21
agcaaaagca gggtgacaaa gacataatgg atccaaacac tgtgtcaagc tttcaggtag      60
attgctttct ttggcatgtc cgcaaacgag ttgcagacca agaactaggt gatgccccat     120
tccttgatcg gcttcgccga gatcagaaat ccctaagagg aaggggcagc actcttggtc     180
tggacatcga gacagccaca cgtgctggaa agcagatagt ggagcggatt ctgaaagaag     240
aatccgatga ggcacttaaa atgaccatgg cctctgtacc tgcgtcgcgt tacctaaccg     300
acatgactct tgaggaaatg tcaagggaat ggtccatgct catacccaag cagaaagtgg     360
caggccctct ttgtatcaga atggaccagg cgatcatggg aggaggtttc ttcggagcta     420
ttgctggttt cttggaagga ggatgggaag gaatgattgc aggttgggga ggaagagaga     480
gccggaaccc agggaatgct tgataataag cggccgcagt gtgattttg accggctgga     540 gactctaata ttgctaaggg ctttcaccga gagggagca attgttggcg aaatttcacc     600
attgccttct cttccaggac atactaatga ggatgtcaaa aatgcaattg gggtcctcat     660
cggaggactt gaatggaatg ataacacagt tcgagtctct aaaactctac agagattcgc     720
ttggagaagc agtaatgaga atgggagacc tccactcact ccaaaacaga acggaaaat     780 ggcgagaaca attaggtcaa aagttcgaag aaataagatg gctgattgaa gaagtgagac     840
acaaattgaa gataacagag aatagttttg agcaaataac atttatacaa gccttacagc     900
tactatttga agtggaacaa gagataagaa ctttctcgtt tcagcttatt taataataaa     960 aaacacccett gtttctact                                                979
```

The invention claimed is:

1. An attenuated influenza A virus inducing a cross-protective response against influenza A and B viruses, comprising a chimeric NS fragment including a truncated reading frame of an NS1 protein and a Nep gene heterologous sequence, wherein said truncated reading frame of the NS1 protein is derived from H1N1 influenza virus subtype, and the Nep gene heterologous sequence is derived from H2N2 influenza virus subtype and wherein said truncated reading frame encodes the NS1 protein consisting of 124 amino acid residues corresponding to SEQ ID NO: 4.

2. An attenuated influenza virus vector expressing a protein or a fragment thereof selected from the group consisting of proteins or fragments thereof from bacteria, viruses, and protozoa, wherein the vector is an attenuated influenza A virus according to claim 1, in which the truncated reading frame of the NS1 protein gene is elongated by an insertion of a sequence of at least one transgene encoding the protein or the fragment thereof from bacteria, viruses, and protozoa, wherein the bacteria, virus, or protozoa is pathogenic.

3. The attenuated influenza virus vector according to claim 2, wherein the protein or the fragment thereof is selected from the group consisting of proteins of an influenza A virus, influenza B virus, *mycobacterium tuberculosis*, herpes virus, respiratory syncytial virus, human immunodeficiency virus, hepatitis C virus, malaria parasite, *Trichomonas*, *Trypanosoma*, *Leishmania*, *Chlamydia*, brucellosis causative agent, or a combination thereof.

4. The attenuated influenza virus vector according to claim 2, wherein the protein or the fragment thereof consists of 10 to 400 amino acids.

5. The attenuated influenza virus vector according to claim 2, wherein the insertion encodes an HA protein region from influenza virus.

6. The attenuated influenza virus vector according to claim 5, wherein the HA protein region is an HA2 subunit region selected from the group consisting of 1-185 amino acids from influenza A virus, 1-186 amino acids from influenza B virus, 23-185 amino acids from influenza A virus, or 65-222 amino acids from influenza A virus.

7. The attenuated influenza virus vector according to claim 2, wherein the insertion encodes a sequence of an influenza A or B virus HA2 subunit region of from 1 to 21 amino acids and a sequence of an influenza A virus NP protein region of from 243 to 251 amino acids.

8. The attenuated influenza virus vector according to claim 2, wherein the insertion encodes protein ESAT-6, Ag85A, Ag85B, Mpt64, HspX, Mtb8.4, or 10.4 of *mycobacterium tuberculosis*, or a fragment thereof.

9. The attenuated influenza virus vector according to claim 8, wherein the viral genome sequence further comprises a sequence encoding a self-cleaving 2A peptide between the truncated reading frame of the NS1 protein gene and the insertion encoding protein ESAT6.

10. An attenuated influenza virus vector expressing an influenza virus protein or a fragment thereof, wherein said vector is an attenuated influenza virus according to claim 1, wherein the truncated reading frame of an NS1 protein gene is elongated by an insertion of a sequence encoding 1-21 aa of an influenza B HA2 protein and 243-251 aa of an influenza A NP protein.

11. An attenuated influenza virus vector having oncolytic activity, wherein said vector is an attenuated influenza A virus according to claim 1, wherein the truncated reading frame of an NS1 protein gene is elongated by an insertion of a sequence encoding a *mycobacterium tuberculosis* protein ESAT-6 or a fragment thereof.

12. The attenuated influenza virus vector according to claim 11, wherein the protein or a fragment thereof consists of 10 to 400 amino acids.

13. The attenuated influenza virus vector according to claim 11, wherein the truncated reading frame of an NS1 protein gene is further elongated by an insertion of a sequence encoding self-cleaving 2A peptide.

14. An attenuated influenza virus vector inducing a cross-protective response against influenza A and B viruses, comprising:
   a nucleotide sequence of a PB2 protein gene of SEQ ID NO: 14 or a nucleotide sequence having at least 95% sequence identity to SEQ ID NO: 14;
   a nucleotide sequence of a PB1 protein gene of SEQ ID NO: 15 or a nucleotide sequence having at least 95% sequence identity to SEQ ID NO: 15;
   a nucleotide sequence of a PA protein gene of SEQ ID NO: 16 or a nucleotide sequence having at least 95% sequence identity to SEQ ID NO: 16;
   a nucleotide sequence of an NP protein gene of SEQ ID NO: 17 or a nucleotide sequence having at least 95% sequence identity to SEQ ID NO: 17;
   a nucleotide sequence of an M protein gene of SEQ ID NO: 18 or a nucleotide sequence having at least 95% sequence identity to SEQ ID NO: 18;
   a nucleotide sequence of an HA protein gene of SEQ ID NO: 19 virus or a nucleotide sequence having at least 95% sequence identity to SEQ ID NO: 19;
   a nucleotide sequence of an NA protein gene of SEQ ID NO: 20 virus or a nucleotide sequence having at least 95% sequence identity to SEQ ID NO: 20;
   a nucleotide sequence of an NS protein chimeric gene of SEQ ID NO: 21 including:
      an NS1 protein reading frame derived from influenza A/PR/8/34 (H1N1), wherein said reading frame is truncated and encodes an NS1 protein consisting of 124 amino acid residues,
      and a Nep gene sequence derived from influenza A/Singapore/1/57-like (H2N2) virus, or
   a nucleotide sequence having at least 95% sequence identity to SEQ ID NO: 21;
   wherein said NS1 protein truncated reading frame is elongated by an insertion of a nucleotide sequence encoding a fusion peptide of an influenza B subunit HA2 region and a nucleotide sequence encoding a conservative B-cell epitope of influenza A virus nucleoprotein (NP).

15. The attenuated influenza virus vector according to claim 14, wherein the nucleotide sequence of the NS protein chimeric gene is set forth in SEQ ID NO:21.

16. An immunogenic composition for the induction of an immune response against an infectious pathogen in a subject, comprising an effective amount of an attenuated influenza virus vector according to claim 2, and a pharmaceutically acceptable carrier.

17. A pharmaceutical composition for the prophylaxis of influenza disease, comprising in an effective amount of an attenuated influenza virus vector according to claim 14 and a pharmaceutically acceptable carrier.

18. The immunogenic or pharmaceutical composition according to claim 16 or 17, respectively, comprising 6.5 to 10.5 log EID50/ml of the attenuated influenza A virus and a buffer solution comprising 0 to 1.5 wt. % of a monovalent salt, 0 to 5 wt. % of an imidazole-containing compound, 0 to 5 wt. % of a carbohydrate component, 0 to 2 wt. % of a protein component, 0 to 2 wt. % of an amino acid component, and 0 to 10 wt. % of hydroxyethylated starch.

19. The immunogenic composition according to claim 16, wherein the buffer solution comprises 0.5 to 1.5 wt. % of a monovalent salt, 0.01 to 5 wt. % of an imidazole-containing compound, 1 to 5 wt. % of a carbohydrate component, 0.1 to 2 wt. % of a protein component, 0.01 to 2 wt. % of an amino acid component, and 1 to 10 wt. % of hydroxyethylated starch.

20. The immunogenic composition according to claim 19, wherein the monovalent salt is sodium chloride, the carbohydrate component is sucrose, trehalose, or lactose, the protein component is a human albumin, casitone, lactalbumin hydrolysate, or gelatin, the amino acid component is arginine, glycine, or sodium glutamate, and the imidazole-containing compound is L-carnosine or N,N-bis[2-(1H-imidazol-5yl)ethyl]propanediamide.

21. The immunogenic composition according to claim 16, wherein the infectious pathogen is selected from the group consisting of an influenza A virus, influenza B virus, *mycobacterium tuberculosis*, herpes simplex virus types I and II, respiratory syncytial virus, human immunodeficiency virus, hepatitis C virus, malaria parasite, *Trichomonas, Chlamydia, Trypanosoma, Leishmania*, or a brucellosis causative agent.

22. The immunogenic composition according to claim 16, wherein the subject is a mammal or a bird.

23. The immunogenic composition according to claim 22, wherein the subject is a human subject.

24. A vaccine against an influenza, comprising an effective amount of an attenuated influenza virus vector according to claim 1, and a pharmaceutically acceptable carrier.

25. A vaccine against influenza comprising an effective amount of an attenuated influenza virus vector according to claim 14 and a pharmaceutically acceptable carrier.

26. The vaccine according to claim 24 or 25, comprising 6.5 to 10.5 log EID50/ml of the attenuated influenza virus vector and a buffer solution comprising 0 to 1.5 wt. % of a monovalent salt, 0 to 5 wt. % of an imidazole-containing compound, 0 to 5 wt. % of a carbohydrate component, 0 to 2 wt. % of a protein component, 0 to 2 wt. % of an amino acid component, and 0 to 10 wt. % of hydroxyethylated starch.

27. The vaccine according to claim 24, wherein the buffer solution comprises 0.5 to 1.5 wt. % of a monovalent salt, 0.01 to 5 wt. % of an imidazole-containing compound, 1 to 5 wt. % of a carbohydrate component, 0.1 to 2 wt. % of a protein component, 0.01 to 2 wt. % of an amino acid component, and 1 to 10 wt. % of hydroxyethylated starch.

28. The vaccine according to claim 27, wherein the monovalent salt is sodium chloride, the carbohydrate component is sucrose, trehalose, or lactose, the protein component is a human albumin, casitone, lactalbumin hydrolysate, or gelatin, the amino acid component is arginine, glycine, or sodium glutamate, and the imidazole-containing compound is L-carnosine or N,N-bis[2-(1H-imidazol-5yl)ethyl]propanediamide.

29. A method for treating and/or prophylaxis of influenza disease in a subject in need thereof, comprising administering to said subject an effective amount of an attenuated influenza virus vector according to claim 2.

30. The method according to claim 29, wherein the influenza disease is caused by a pathogen selected from the group consisting of an influenza A virus and an influenza B virus.

31. The method according to claim 30, wherein the subject is a mammal or a bird.

32. The method according to claim 31, wherein the subject is a human subject.

33. A pharmaceutical composition for the treatment of an oncological disease in a subject, comprising an attenuated influenza virus vector according to claim 11 in an effective amount, and a pharmaceutically acceptable carrier.

34. The composition according to claim 33, comprising 8.5 to 10.5 log EID50/ml of the attenuated influenza virus vector, and a buffer solution comprising 0 to 1.5 wt. % of a monovalent salt, 0 to 5 wt. % of an imidazole-containing compound, 0 to 5 wt. % of a carbohydrate component, 0 to 2 wt. % of a protein component, 0 to 2 wt. % of an amino acid component, and 0 to 10 wt. % of hydroxyethylated starch.

35. The composition according to claim 34, wherein buffer solution comprises 0.5 to 1.5 wt. % of a monovalent salt, 0.01 to 5 wt. % of an imidazole-containing compound, 1 to 5 wt. % of a carbohydrate component, 0.1 to 2 wt. % of a protein component, 0.01 to 2 wt. % of an amino acid component, and 1 to 10 wt. % of hydroxyethylated starch.

36. The composition according to claim 35, wherein the monovalent salt is sodium chloride, the carbohydrate component is starch, the protein component is a human albumin, the amino acid component is arginine, and the an imidazole-containing compound is L-carnosine or N,N'-bis[2-(1H-imidazol-5yl)ethyl]propanediamide.

37. A method for treating an oncological disease in a subject in need thereof, comprising administering to said subject an effective amount of an attenuated influenza virus vector according to claim 11.

38. The method according to claim 37, wherein the administration is intratumor administration, administration to a cavity formed after surgical removal of a tumor, or intravenous administration.

39. The method according to claim 37, wherein the oncological disease is selected from the group consisting of colorectal cancer, cardioesophageal cancer, pancreatic cancer, cholangiocellular cancer, glioma, glioblastoma, and melanoma.

* * * * *